(12) United States Patent
De Matos et al.

(10) Patent No.: US 7,968,605 B2
(45) Date of Patent: Jun. 28, 2011

(54) METHODS FOR TREATING INFLAMMATORY DISEASE BY ADMINISTERING ALDEHYDES AND DERIVATIVES THEREOF

(75) Inventors: Marta Norton De Matos, Lisbon (PT); Carlos C. Romao, Cascais (PT)

(73) Assignee: ALFAMA—Investigação e Desenvolvimento de Produtos Farmacêuticos, Lda., Porto Salvo (PT)

( * ) Notice: Subject to any disclaimer, the term of this patent is extended or adjusted under 35 U.S.C. 154(b) by 277 days.

(21) Appl. No.: 11/702,970

(22) Filed: Feb. 6, 2007

(65) Prior Publication Data

US 2007/0219120 A1   Sep. 20, 2007

Related U.S. Application Data

(60) Continuation-in-part of application No. 11/288,670, filed on Nov. 29, 2005, and a continuation-in-part of application No. 11/453,319, filed on Jun. 14, 2006, which is a division of application No. 11/288,670, filed on Nov. 29, 2005, which is a division of application No. 10/356,738, filed on Feb. 3, 2003, now Pat. No. 7,011,854.

(60) Provisional application No. 60/353,233, filed on Feb. 4, 2002, provisional application No. 60/873,155, filed on Dec. 6, 2006.

(51) Int. Cl.
*A61K 31/11* (2006.01)
*A61K 35/00* (2006.01)
*A61K 31/74* (2006.01)

(52) U.S. Cl. ...... 514/693; 514/699; 514/703; 424/78.05

(58) Field of Classification Search .................. 514/693, 514/699, 703; 424/78.08
See application file for complete search history.

(56) References Cited

U.S. PATENT DOCUMENTS

| | | | |
|---|---|---|---|
| 2,870,180 A | 1/1959 | Kozikowski et al. | |
| 3,278,570 A | 10/1966 | Wilkinson et al. | |
| 3,694,232 A | 9/1972 | Hall et al. | |
| 3,812,166 A | 5/1974 | Wiechert | |
| 3,829,504 A | 8/1974 | Hall et al. | |
| 3,980,583 A | 9/1976 | Mitchell et al. | |
| 4,189,487 A * | 2/1980 | Klosa | 514/355 |
| 4,312,989 A | 1/1982 | Spielvogel et al. | |
| 4,322,411 A | 3/1982 | Vinegar et al. | |
| 4,613,621 A | 9/1986 | Horrmann | |
| 4,649,151 A | 3/1987 | Dougherty et al. | |
| 4,657,902 A | 4/1987 | Kappas et al. | |

(Continued)

FOREIGN PATENT DOCUMENTS

DE   4014762 A1   11/1991

(Continued)

OTHER PUBLICATIONS

Shapiro, American Journal of Therapeutics, 1998, 5(5), pp. 323-353.*

(Continued)

*Primary Examiner* — Johann R Richter
*Assistant Examiner* — Abigail Fisher
(74) *Attorney, Agent, or Firm* — Wolf, Greenfield & Sacks, P.C.

(57) ABSTRACT

A method is disclosed for treating inflammatory disease in an animal in need thereof by administering to the animal a pharmaceutical composition containing an anti-inflammatory effective amount of an organic aldehyde compound or a derivative thereof in a pharmaceutically acceptable vehicle.

17 Claims, 25 Drawing Sheets

U.S. PATENT DOCUMENTS

| | | | |
|---|---|---|---|
| 4,668,670 A | 5/1987 | Rideout et al. | |
| 4,699,903 A | 10/1987 | Rideout et al. | |
| 4,709,083 A | 11/1987 | Spielvogel | |
| 4,910,211 A | 3/1990 | Imamura et al. | |
| 4,938,949 A | 7/1990 | Borch et al. | |
| 5,010,073 A | 4/1991 | Kappas et al. | |
| 5,086,060 A | 2/1992 | Haley et al. | |
| 5,102,670 A | 4/1992 | Abraham et al. | |
| 5,254,706 A | 10/1993 | Spielvogel et al. | |
| 5,312,816 A | 5/1994 | Spielvogel et al. | |
| 5,350,767 A * | 9/1994 | Hallberg et al. | 514/562 |
| 5,447,939 A | 9/1995 | Glasky et al. | |
| 5,621,000 A | 4/1997 | Arena et al. | |
| 5,631,284 A | 5/1997 | Legzdins et al. | |
| 5,659,027 A | 8/1997 | Spielvogel et al. | |
| 5,664,563 A | 9/1997 | Schroeder et al. | |
| 5,670,664 A | 9/1997 | Kao et al. | |
| 5,700,947 A | 12/1997 | Soldato | |
| 5,756,492 A | 5/1998 | Buelow et al. | |
| 5,767,157 A * | 6/1998 | Van Moerkerken | 514/562 |
| 5,801,184 A | 9/1998 | Glasky et al. | |
| 5,811,463 A | 9/1998 | Legzdins et al. | |
| 5,824,673 A | 10/1998 | Abrams et al. | |
| 5,861,426 A | 1/1999 | Del Soldato et al. | |
| 5,882,674 A | 3/1999 | Herrmann et al. | |
| 5,885,621 A | 3/1999 | Head et al. | |
| 5,888,982 A | 3/1999 | Perrella et al. | |
| 5,891,689 A | 4/1999 | Takle et al. | |
| 6,025,394 A | 2/2000 | Menander et al. | |
| 6,027,936 A | 2/2000 | Glasky | |
| 6,040,341 A | 3/2000 | Del Soldato et al. | |
| 6,051,576 A | 4/2000 | Ashton et al. | |
| 6,060,467 A | 5/2000 | Buelow et al. | |
| 6,066,333 A | 5/2000 | Willis et al. | |
| 6,177,471 B1 | 1/2001 | Menander et al. | |
| 6,203,991 B1 | 3/2001 | Nabel et al. | |
| 6,211,233 B1 | 4/2001 | Del Soldato | |
| 6,218,417 B1 | 4/2001 | Del Soldato | |
| 6,242,432 B1 | 6/2001 | del Soldato | |
| 6,251,927 B1 | 6/2001 | Lai et al. | |
| 6,284,752 B1 | 9/2001 | Abrams et al. | |
| 6,331,564 B1 * | 12/2001 | Brugnara et al. | 514/520 |
| 6,338,963 B1 | 1/2002 | Glasky et al. | |
| 6,344,178 B1 | 2/2002 | Alberto et al. | |
| 6,350,752 B1 | 2/2002 | Glasky et al. | |
| 6,417,182 B1 | 7/2002 | Abrams et al. | |
| 6,518,269 B1 | 2/2003 | Camden et al. | |
| 6,645,938 B2 | 11/2003 | Oeltgen et al. | |
| 6,673,908 B1 | 1/2004 | Stanton, Jr. | |
| 7,011,854 B2 | 3/2006 | Haas et al. | |
| 7,045,140 B2 | 5/2006 | Motterlini et al. | |
| 7,053,242 B1 | 5/2006 | Alberto et al. | |
| 2002/0043595 A1 | 4/2002 | Bridgers | |
| 2002/0155166 A1 | 10/2002 | Choi et al. | |
| 2002/0165242 A1 | 11/2002 | Glasky et al. | |
| 2002/0193363 A1 | 12/2002 | Bridger et al. | |
| 2003/0039638 A1 | 2/2003 | Bach et al. | |
| 2003/0064114 A1 | 4/2003 | Motterlini et al. | |
| 2003/0068387 A1 | 4/2003 | Buelow et al. | |
| 2003/0124157 A1 | 7/2003 | Engles et al. | |
| 2003/0157154 A1 | 8/2003 | Fuller et al. | |
| 2003/0207786 A1 | 11/2003 | Miracle et al. | |
| 2003/0219496 A1 | 11/2003 | Otterbein et al. | |
| 2003/0219497 A1 | 11/2003 | Otterbein et al. | |
| 2004/0052866 A1 | 3/2004 | Otterbein et al. | |
| 2004/0067261 A1 | 4/2004 | Haas et al. | |
| 2004/0122091 A1 * | 6/2004 | Dasseux et al. | 514/517 |
| 2004/0131602 A1 | 7/2004 | Buelow et al. | |
| 2004/0143025 A1 | 7/2004 | Buelow et al. | |
| 2004/0214900 A1 | 10/2004 | Forbes et al. | |
| 2004/0228930 A1 | 11/2004 | Billiar et al. | |
| 2004/0258772 A1 | 12/2004 | Otterbein et al. | |
| 2005/0048133 A1 | 3/2005 | Pinsky et al. | |
| 2005/0175555 A1 | 8/2005 | Stradi et al. | |
| 2006/0115542 A1 | 6/2006 | Motterlini et al. | |
| 2006/0127501 A1 | 6/2006 | Motterlini et al. | |
| 2006/0147548 A1 | 7/2006 | Motterlini et al. | |
| 2006/0148900 A1 | 7/2006 | Haas et al. | |
| 2006/0233890 A1 | 10/2006 | Haas et al. | |
| 2007/0065485 A1 | 3/2007 | Motterlini et al. | |
| 2007/0207217 A1 | 9/2007 | Haas et al. | |
| 2007/0207993 A1 | 9/2007 | Haas et al. | |
| 2008/0026984 A1 * | 1/2008 | De Matos et al. | 514/2 |
| 2010/0105770 A1 | 4/2010 | Motterlini et al. | |

FOREIGN PATENT DOCUMENTS

| | | |
|---|---|---|
| EP | 0034238 A1 | 8/1981 |
| EP | 0076493 A2 | 4/1983 |
| EP | 0181721 A1 | 5/1986 |
| EP | 0632026 A1 | 1/1995 |
| FR | 2816212 A1 | 5/2002 |
| GB | 1107510 A | 3/1968 |
| GB | 111872.8 A | 5/2001 |
| GB | 227138.5 A | 10/2002 |
| GB | 227135.1 A | 11/2002 |
| GB | 2395431 A | 5/2004 |
| GB | 2395432 A | 5/2004 |
| HU | 57595 A2 | 12/1991 |
| HU | 211084 A2 | 12/1991 |
| WO | WO-85/04326 A1 | 10/1985 |
| WO | WO-91/01128 A1 | 2/1991 |
| WO | WO-91/01301 A1 | 2/1991 |
| WO | WO-92/03402 A1 | 3/1992 |
| WO | WO-92/04905 A1 | 4/1992 |
| WO | WO-93/05795 A1 | 4/1993 |
| WO | WO-94/01413 A1 | 1/1994 |
| WO | WO-94/22482 A1 | 10/1994 |
| WO | WO-95/05814 A1 | 3/1995 |
| WO | WO-95/09831 A1 | 4/1995 |
| WO | WO-95/35105 A1 | 12/1995 |
| WO | WO-96/03125 A1 | 2/1996 |
| WO | WO-96/09038 A2 | 3/1996 |
| WO | WO-97/16405 A1 | 5/1997 |
| WO | WO-97/36615 A1 | 10/1997 |
| WO | WO-97/37644 A1 | 10/1997 |
| WO | WO-98/09618 A2 | 3/1998 |
| WO | WO-98/29115 A1 | 7/1998 |
| WO | WO-98/38179 A1 | 9/1998 |
| WO | WO-98/48848 A1 | 11/1998 |
| WO | WO-99/67231 A1 | 12/1999 |
| WO | WO-00/10613 A2 | 3/2000 |
| WO | WO-00/21965 A1 | 4/2000 |
| WO | WO-00/36113 A2 | 6/2000 |
| WO | WO-00/56145 A1 | 9/2000 |
| WO | WO-00/56743 A1 | 9/2000 |
| WO | WO-00/61537 A2 | 10/2000 |
| WO | WO-01/12584 A2 | 2/2001 |
| WO | WO-01/16359 A2 | 3/2001 |
| WO | WO-01/25243 A1 | 4/2001 |
| WO | WO-01/28545 A2 | 4/2001 |
| WO | WO-02/078684 A2 | 10/2002 |
| WO | WO-02/080923 A1 | 10/2002 |
| WO | WO-02/092072 A2 | 11/2002 |
| WO | WO-02/092075 A2 | 11/2002 |
| WO | WO-03/000114 A2 | 1/2003 |
| WO | WO-03/066067 A2 | 8/2003 |
| WO | WO-03/067598 A2 | 8/2003 |
| WO | WO-03/072024 A2 | 9/2003 |
| WO | WO-03/082850 A1 | 10/2003 |
| WO | WO-03/088923 A2 | 10/2003 |
| WO | WO-03/088981 A1 | 10/2003 |
| WO | WO-03/094932 A1 | 11/2003 |
| WO | WO-03/096977 A2 | 11/2003 |
| WO | WO-03/103585 A2 | 12/2003 |
| WO | WO-2004/029033 A1 | 4/2004 |
| WO | WO-2004/043341 A2 | 5/2004 |
| WO | WO-2004/045598 A1 | 6/2004 |
| WO | WO-2004/045599 A1 | 6/2004 |
| WO | WO-2004/080420 A2 | 9/2004 |
| WO | WO-2005/013691 A1 | 2/2005 |
| WO | WO-2005/090400 A1 | 9/2005 |
| WO | WO-2006/012215 A1 | 2/2006 |
| WO | WO-2007/073226 A1 | 6/2007 |
| WO | WO-2007/085806 A2 | 8/2007 |
| WO | WO-2008/003953 A2 | 1/2008 |

| WO | WO-2008/069688 A2 | 6/2008 |
| WO | WO-2008/130261 A1 | 10/2008 |
| WO | WO-2009/013612 A1 | 1/2009 |

OTHER PUBLICATIONS

Nathan, Nature, 2002, 420, pp. 846-852.*
Chemical Abstracts 141:270758 (2004).*
Chemical Abstracts 140:40075 (2004).*
Chemical Abstracts 142:211995 (2004).*
Chemical Abstracts 137:119662 (2002).*
"supramolecule" IUPAC compendium of chemical terminology. Retrieved from the internet at www.iupac.org/goldbook/SO6153.pdf on May 8, 2006.
Biosis Chem Abstracts Database. Accession No. PREV200600414130. 2005. Otterbein et al., Cell Mol Biol (Noisyle-grand). Oct. 3, 2005;51(5):433-40. Abstract.
Abel et al., Anionic halogenopentacarbonyls of chromium, molybdenum, and tungsten. J Chem Soc. 1963:2068-70.
Abel et al., Carbonyl halides of manganese and some related compounds. J Chem Soc. 1959;Part 2:1501-5.
Abel et al., Reaction of molybdenum carbonyl with various halides: a potassium etherate salt. Chem Indust. 1960;442.
Abraham et al., The biological significance and physiological role of heme oxygenase. Cell Physiol Biochem. 1996;6:129-68.
Adkison et al., Semicarbazone-based inhibitors of cathepsin K, are they prodrugs for aldehyde inhibitors? Bioorg Med Chem Lett. Feb. 15, 2006;16(4):978-83. Epub Nov. 15, 2005. Abstract only.
Akamatsu et al., Heme oxygenase-1-derived carbon monoxide protects hearts from transplant associated ischemia reperfusion injury. FASEB J. Apr. 2004;18(6):771-2. Epub Feb. 20, 2004.
Alberto et al., A novel organometallic aqua complex of technetium for the labeling of biomolecules: synthesis of [99mTc(OH2)3(CO)3]+ from [99mTcO4]− in aqueous solution and its reaction with a bifunctional ligand. J Am Chem Soc. 1998;120:7987-8.
Alberto et al., Synthesis and properties of boranocarbonate: a convenient in situ CO source for the aqueous preparation of [(99m)Tc(OH(2))3(CO)3]+. J Am Chem Soc. Apr. 4, 2001;123(13):3135-6.
Alessio et al., Carbonyl Derivatives of Chloride-Dimethyl Sulfoxide-Ruthenium(II) Complexes: Synthesis, Structural Characterization, and Reactivity of Ru(CO)x(DMSO)4-xC12 Complexes (x = 1-3). Inorg Chem. 1995;34(19):4722-34.
Alessio et al., Carbonyl Derivatives of Chloride-Dimethyl Sulfoxide-Ruthenium(III) Complexes: Synthesis, Crystal Structure, and Reactivity of [(DMSO)2H][trans-RuC14(DMSO-O)(C0)] and mer,cis-RuC13(DMSO-O)2(CO). Inorg Chem. 1995;34(19):4716-21.
Allanson et al., Ultraviolet A (320-400 nm) modulation of ultraviolet B (290-320 nm)-induced immune suppression is mediated by carbon monoxide. J Invest Dermatol. Mar. 2005;124(3):644-50.
Allardyce et al., Development of organometallic (organo-transition metal) pharmaceuticals. Appl Organomet Chem. 2005;19:1-10.
Amersi et al., Ex vivo exposure to carbon monoxide prevents hepatic ischemia/reperfusion injury through p. 38 MAP kinase pathway. Hepatology. Apr. 2002;35(4):815-23.
Andreadis et al., Oxidative and nitrosative events in asthma. Free Radic Biol Med. Aug. 1, 2003;35(3):213-25. Review. Abstract only.
Angelici et al., Carboxamido carbonyl complexes of manganese(I). Inorg Chim Acta. Mar. 1968;2:3-7. Abstract only.
Angelici, Preparation, characterization, and reactions of the cis-Dihalotetracarbonylmanganate(I) anions. Inorg Chem. Aug. 1964;3(8):1099-1102.
Aujard et al., Tridemethylisovelleral, a potent cytotoxic agent. Bioorg Med Chem. Nov. 15, 2005;13(22):6145-50. Epub Aug. 1, 2005. Abstract only.
Bagul et al., Carbon monoxide protects against ischemia-reperfusion injury in an experimental model of controlled nonheartbeating donor kidney. Transplantation. Feb. 27, 2008;85(4):576-81.
Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.
Bannenberg et al., Therapeutic applications of the gaseous mediators carbon monoxide and hydrogen sulfide. Expert Opin Ther Pat. May 2009;19(5):663-82. Review.
Barkoudah et al., The permissive role of endothelial NO in CO-induced cerebrovascular dilation. Am J Physiol Heart Circ Physiol. Oct. 2004;287(4):H1459-65. Epub Jun. 10, 2004.
Bauer et al., Evidence for a functional link between stress response and vascular control in hepatic portal circulation. Am J Physiol. Nov. 1996;271(5 Pt 1):G929-35.
Bauerová et al., Role of reactive oxygen and nitrogen species in etiopathogenesis of rheumatoid arthritis. Gen Physiol Biophys. Oct. 1999;18 Spec No.:15-20. Review. Abstract only.
Beal, Oxidatively modified proteins in aging and disease. Free Radic Biol Med. May 1, 2002;32(9):797-803. Review. Abstract only.
Beaty et al., An in vitro model for the in vivo mobilization of cadmium by chelating agents using 113Cd-NMR spectroscopy. Chem Res Toxicol. 1992;5:568-75. Abstract only.
Becker et al., Age-related changes in antibody-dependent cell-mediated cytotoxicity in mouse spleen. Isr J Med Sci. Feb. 1979;15(2):147-50.
Becker et al., NO-independent regulatory site of direct sGC stimulators like YC-1 and BAY 41/2272. BMC Pharmacol. 2001;1:13. Epub Dec. 28, 2001.
Berman et al., Sensitization and catalysis of light-induced decarbonylation of aldehydes. J Am Chem Soc. 1963;85(24):4010-4013.
Beutler, The effect of carbon monoxide on red cell life span in sickle cell disease. Blood. Aug. 1975;46(2):253-9.
Boissiere et al., Exercise and vasorelaxing effects of CO-releasing molecules in hypertensive rats. Med Sci Sports Exerc. Apr. 2006;38(4):652-9.
Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.
Brashears et al., Effect of meat packaging technologies on the safety and spoilage-indicating characteristics of ground beef—Phase 1: safety characteristics. 2006. National Cattleman's Beef Asscoiation. 23 pages. Available at www.fda.gov/ohrms/dockets/dockets/05p0459/05p-0459-c000009-01-vol2.pdf.
Brooks et al., The spoilage characteristics of ground beef packaged in high-oxygen and low-oxygen modified atmosphere packages. Proc. Reciprocal Meat Conference. University of Illinois at Urbana-Champaign. 2006:61-5.
Brouard et al., Carbon monoxide generated by heme oxygenase 1 suppresses endothelial cell apoptosis. J Exp Med. Oct. 2, 2000;192(7):1015-26.
Brüne et al., Inhibition of platelet aggregation by carbon monoxide is mediated by activation of guanylate cyclase. Mol Pharmacol. Oct. 1987;32(4):497-504.
Bundgaard et al., Pro-drugs as delivery systems. Pharm Int. 1981;2:136-40.
Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.
Burgmayer et al., Synthesis and structure of a 7-coordinate molybdenum carbonyl fluoride derivative—Et4n Mo(Co)2(S2cnet2)2f. Inorganic Chem. 1985;24:2224-30.
Campbell et al., Molecular targets in immune-mediated diseases: the case of tumour necrosis factor and rheumatoid arthritis. Immunol Cell Biol. Oct. 2003;81(5):354-66.
Carroll et al., Ligand abstraction in the reaction of aryldiazonium ions with some iron complexes containing coordinated cysteine, maleonitriledithiol, or triarylphosphine. Can J Chem. 1974;52:1914-22.
Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191.
Chakravortty et al., Inducible nitric oxide synthase and control of intracellular bacterial pathogens. Microbes Infect. Jun. 2003;5(7):621-7. Review. Abstract only.

Chatterjee, Water-soluble carbon monoxide-releasing molecules: helping to elucidate the vascular activity of the 'silent killer'. Br J Pharmacol. Jun. 2004;142(3):391-3. Epub May 17, 2004.

Chauveau et al., Gene transfer of heme oxygenase-1 and carbon monoxide delivery inhibit chronic rejection. Am J Transplant. Aug. 2002;2(7):581-92.

Chlopicki et al., Carbon monoxide released by CORM-3 inhibits human platelets by a mechanism independent of soluble guanylate cyclase. Cardiovasc Res. Jul. 15, 2006;71(2):393-401. Epub Mar. 22, 2006.

Cihonski et al., Crown ethers in inorganic chemistry—preparation and characterization of group 6 pentacarbonyl hydroxides and fluorides. Inorganic Chem. 1975;14:1717-20.

Clark et al., Cardioprotective actions by a water-soluble carbon monoxide-releasing molecule. Circ Res. Jul. 25, 2003;93(2):e2-8. Epub 2003 Jul. 3, 2003.

Clark et al., Heme oxygenase-1-derived bilirubin ameliorates postischemic myocardial dysfunction. Am J Physiol Heart Circ Physiol. Feb. 2000;278(2):H643-51.

Clark et al., Measuring left ventricular function in the normal, infarcted and CORM-3-preconditioned mouse heart using complex admittance-derived pressure volume loops. J Pharmacol Methods. Mar.-Apr. 2009;59(2):94-9.

Coburn et al., Endogenous carbon monoxide production in man. J Clin Invest. Jul. 1963;42:1172-8.

Coceani et al., Carbon monoxide formation in the ductus arteriosus in the lamb: implications for the regulation of muscle tone. Br J Pharmacol. Feb. 1997;120(4):599-608.

Coceani, Carbon monoxide in vasoregulation: the promise and the challenge. Circ Res. Jun. 23, 2000;86(12):1184-6. Review.

Cohen et al., Dithiobenzoatotetracarbonylmanganese(I). Inorg Chem. 1964;3(11):1641-42.

Conant et al., The action of the rignard reagent on highly branched carbonyl compounds. J Am Chem Soc. 1929;51(4):1246-55.

Cotton et al., Dimethyl- and diethyldithiocarbamate complexes of some metal carbonyl compounds. Inorg Chem. Jun. 2, 1964;3:1398-1402.

Cotton et al., X-ray molecular structures of Mn(CO)5(O2CCF3) and Mn(CO)3(C5H5N)2(O2CCF3). Inorg Chem. 1981;20(4):1287-91.

Coville et al., Steric measurement of substituted cyclopentadiene ligands and the synthesis and proton NMR spectral analysis of [(.eta.5-C5H4R)Fe(CO)(L)I] complexes with variable R. Organometallics. 1992;11(3):1082-90.

De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.

De Backer et al., Water-soluble CO-releasing molecules reduce the development of postoperative ileus via modulation of MAPK/HO-1 signalling and reduction of oxidative stress. Gut. Mar. 2009;58(3):347-56. Epub Nov. 20, 2008.

De Filippo et al., Inductive effect in dithiocarbanate decomposition mechanism. J Org Chem. 1973;38(3):560-3.

Desmard et al., A carbon monoxide-releasing molecule (CORM-3) exerts bactericidal activity against Pseudomonas aeruginosa and improves survival in an animal model of bacteraemia. FASEB J. Apr. 2009;23(4):1023-31. Epub Dec. 18, 2008.

Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.

Dharmaraj et al., Ruthenium (II) complexes containing bidentate Schiff bases and their antifungal activity. Transition Metal Chemistry. 2001; 26(1-2): 105-109.

Di Pascoli et al., Chronic CO levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.

Diamantis et al., Preparation and structure of ethylenediaminetetraacetate complexes of ruthenium(II) with dinitrogen, carbon monoxide, and other π-acceptor ligands. Inorg Chem. 1981;20:1142-50.

Douglas et al., Preparation of some group Vi fluorometal carbonyl derivatives. J Organometal Chem. 1974;65:65-9.

Drew et al., Synthesis, spectral properties, and reactions of manganese and rhenium pentacarbonyl phosphine and phosphite cation derivatives and related complexes. Inorg. Chem. 1975;14(7):1579-84.

Dröge et al., Free radicals in the physiological control of cell function. Physiol Rev. Jan. 2002;82(1):47-95. Review.

Duchêne et al., Cyclodextrins in targeting. Application to nanoparticles. Adv Drug Deliv Rev. Mar. 1, 1999;36(1):29-40.

Durante, Heme oxygenase-1 in growth control and its clinical application to vascular disease. J Cell Physiol. Jun. 2003;195(3):373-82. Review.

Egli et al., Organometallic 99mTc-aquaion labels peptide to an unprecedented high specific activity. J Nucl Med. Nov. 1999;40(11):1913-7.

El-Sayed et al., Catalysis by crown ether complexes—part III effect of cation on the catalytic activity of crown ether—alkali metal halide complexes in the liquid phase oxidation of ethylbenzene. Egypt J Chem. 1979;22(1):23-8.

Elliott et al., Nitric oxide: a regulator of mucosal defense and injury. J Gastroenterol. Dec. 1998;33(6):792-803. Review. Abstract only.

Fairlamb et al., η4-pyrone iron(0)carbonyl complexes as effective CO-releasing molecules (CO-RMs). Bioorg Med Chem Lett. Feb. 15, 2006;16(4):995-8. Epub Nov. 11, 2005.

Fang, Antimicrobial reactive oxygen and nitrogen species: concepts and controversies. Nat Rev Microbiol. Oct. 2004;2(10):820-32. Review. Abstract only.

Feldmann et al., Anti-TNF alpha therapy of rheumatoid arthritis: what have we learned? Annu Rev Immunol. 2001;19:163-96. Review.

Ferrier et al., FTIR spectrometric study of geometrical isomers of dicarbonyl ferrobiscyteinate influence of the counter cation.J Molec Struct. 1995;344(3):189-93.

Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.

Fischer et al., Methylpyridin-Chrom(O)-Tricarbonyl. Zeitschrift Fur Naturforschung Part-B-Chemie Biochemie Biophysik Biologie Und Verwandten Gebiete. 1959;14:736-7. English translation provided.

Fischer et al., Uber aromatenkomplexe von metallen .37. zur aromatenkomplexebildung des pyridins mit chromhexacarbonyl. Chemische berichte-recueil. 1960;93:1156-61. English abstract provided.

Fischer, Crystal structure of 1,4,7,10,13-pentaoxacylcopentadecane sodium bromide, C10H20BrNaO5. Zeitschrift fur kristallographie. 1996;2001:827-8. English translation provided.

Fiumana et al., Carbon monoxide mediates vasodilator effects of glutamate in isolated pressurized cerebral arterioles of newborn pigs. Am J Physiol Heart Circ Physiol. Apr. 2003;284(4):H1073-9.

Foresti et al., Reviewing the use of carbon monoxide-releasing molecules (CO-RMs) in biology: implications in endotoxin-mediated vascular dysfunction. Cell Mol Biol (Noisy-le-grand). Sep. 30, 2005;51(4):409-23.

Foresti et al., The heme oxygenase pathway and its interaction with nitric oxide in the control of cellular homeostasis. Free Radic Res. Dec. 1999;31(6):459-75. Review.

Foresti et al., Vasoactive properties of CORM-3, a novel water-soluble carbon monoxide-releasing molecule. Br J Pharmacol. Jun. 2004;142(3):453-60. Epub May 17, 2004.

Frangogiannis et al., The inflammatory response in myocardial infarction. Cardiovasc Res. Jan. 2002;53(1):31-47. Review.

Friebe et al., Sensitizing soluble guanylyl cyclase to become a highly CO-sensitive enzyme. EMBO J. Dec. 16, 1996;15(24):6863-8.

Friebe et al., YC-1 potentiates nitric oxide- and carbon monoxide-induced cyclic GMP effects in human platelets. Mol Pharmacol. Dec. 1998;54(6):962-7.

Fujita et al., Paradoxical rescue from ischemic lung injury by inhaled carbon monoxide driven by derepression of fibrinolysis. Nat Med. May 2001;7(5):598-604.

Fukuda et al., Induction of heme oxygenase-1 (HO-1) after traumatic brain injury in the rat. Neurosci Lett. Oct. 20, 1995;199(2):127-30.

Furchgott et al., Endothelium-dependent and -independent vasodilation involving cyclic GMP: relaxation induced by nitric oxide, carbon monoxide and light. Blood Vessels. 1991;28(1-3):52-61.

Giboreau et al., Procedure for the preparation of pure dithiocarbamates. J Org Chem. 1994;59:1205-7.

Gordeuk et al., Carbonyl iron therapy for iron deficiency anemia. Blood. Mar. 1986;67(3):745-52.

Greener et al., Now you're signaling, with gas: gasotransmitters open a window on biology and drug development. The Scientist. 2004;18(17):20.

Guo et al., Administration of a CO-releasing molecule at the time of reperfusion reduces infarct size in vivo. Am J Physiol Heart Circ Physiol. May 2004;286(5):H1649-53. Epub Jan. 2, 2004.

Günther et al., Carbon monoxide protects pancreatic beta-cells from apoptosis and improves islet function/survival after transplantation. Diabetes. Apr. 2002;51(4):994-9. MEDLINE Abstract.

Haag et al., Polymer therapeutics: concepts and applications. Angew Chem Int Ed Engl. Feb. 13, 2006;45(8):1198-215. Review. Abstract only.

Haddleton et al., [N-Alkyl-(2-pyridyl)methanimine]copper(I) complexes: characterisation and application as catalysts for atom-transfer polymerisation. Eur J Inorg Chem. Dec. 7, 1998;1998(11):1799-1806. Abstract only.

Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.

Hadjigogos, The role of free radicals in the pathogenesis of rheumatoid arthritis. Panminerva Med. Mar. 2003;45(1):7-13. Review. Abstract only.

Hall et al., DNA interaction with metal complexes and salts of substituted boranes and hydroborates in murine and human tumor cell lines. Anticancer Drugs. Aug. 1991;2(4):389-99.

Hall et al., The anti-inflammatory activity of boron derivatives in rodents. Met Based Drugs. 1995;2(1):1-12.

Hall et al., The anti-inflammatory activity of metal complexes and salts of amine carboxyboranes. Appl Organomett Chem. 1994;8:473-80.

Hall et al., The hypolipidemic activity of metal complexes of amine carboxyboranes in rodents. Met Based Drugs. 1994;1(4):329-36.

Hancock et al., Antibody-induced transplant arteriosclerosis is prevented by graft expression of anti-oxidant and anti-apoptotic genes. Nat Med. Dec. 1998;4(12):1392-6.

Henricks et al., Reactive oxygen species as mediators in asthma. Pulm Pharmacol Ther. 2001;14(6):409-20. Review. Abstract only.

Herrick et al., Flash photolytic investigation of photoinduced carbon monoxide dissociation from dinuclear manganese carbonyl compounds. Inorg Chem. 1984;23:4550-3.

Hieber et al., Derivate des Mangancarbonyls mit schwefelorganischen Liganden. Chemische Berichte. 1966;99(7):2312-21. English abstract provided.

Hitchon et al., Oxidation in rheumatoid arthritis. Arthritis Res Ther. 2004;6(6):265-78. Epub Oct. 13, 2004. Review.

Hogg, Free radicals in disease. Semin Reprod Endocrinol. 1998;16(4):241-8. Review. Abstract only.

Holmuhamedov et al., Mitochondrial ATP-sensitive K+ channels modulate cardiac mitochondrial function. Am J Physiol. Nov. 1998;275(5 Pt 2):H1567-76.

Hosgood et al., Application of nitric oxide and carbon monoxide in a model of renal preservation. Br J Surg. Aug. 2008;95(8):1060-7.

Huang et al., Photolysis of the histidine-heme-CO complex. J Am Chem Soc. 1991;113:9141-4.

Huebers et al., Absorption of carbonyl iron. J Lab Clin Med. Nov. 1986;108(5):473-8.

Ignat'Ev et al., Reactivity of perfluoroakyl halides towards nucleophiles. Russ J Electrochem. 1995;31(12):1235-9. Translated from Elektrokhimiya. 1995:31(12):1337-42.

Jander et al., Neutralisationenanaloge reaktionen in essigaureanhybrid. Zietschrift fur anorganische chemie. 1948;255:238-52. English abstract provided.

Jellum et al., Quantitative determination of biologically important thiols and disulfides by gas-liquid chromatography. Analyt Biochem. 1969;31:339-47. Abstract only.

Johansen et al., Spectrophotometric determination of the rates of hydrolysis of aldehyde-releasing pro-drugs in aqueous solution and plasma. Intl J Pharma. Dec. 1982;13(1):89-98. Abstract only.

Johnson et al., Metal carbonyls as pharmaceuticals? [Ru(CO)3CI(glycinate)], a CO-releasing molecule with an extensive aqueous solution chemistry. Dalton Trans. Apr. 21, 2007;(15):1500-8. Epub Mar. 8, 2007.

Johnson et al., Metal carbonyls: a new class of pharmaceuticals? Angew Chem Int Ed Engl. Aug. 18, 2003;42(32):3722-9.

Johnson et al., Role of endogenous carbon monoxide in central regulation of arterial pressure. Hypertension. Oct. 1997;30(4):962-7.

Józkowicz et al., Heme oxygenase and angiogenic activity of endothelial cells: stimulation by carbon monoxide and.inhibition by tin protoporphyrin-IX. Antioxid Redox Signal. Apr. 2003;5(2):155-62.

Kamimura et al., The protective effect of carbon monoxide on the ischemia-induced cell death. The J Biochem. Aug. 2002;74(8):926. Japanese abstract. English translation provided.

Kharitonov et al., Basis of guanylate cyclase activation by carbon monoxide. Proc Natl Aced Sci U S A. Mar. 28, 1995;92(7):2568-71.

Kharitonov et al., Kinetics and equilibria of soluble guanylate cyclase ligation by CO: effect of YC-1. Biochemistry. Aug. 17, 1999;38(33):10699-706.

Krueger et al., Potential of tumor necrosis factor inhibitors in psoriasis and psoriatic arthritis. Arch Dermatol. Feb. 2004;140(2):218-25. Review.

Kuiate 'et al., Composition of the essential oil from leaves and flowers of Dichrocephala integrifolia (L.) O. Kuntze Chev. From Cameroon. Flavour and Fragrance J. Nov./Dec. 1999;14(6):419-20. Abstract only.

Lambert et al., O,O'-Diphenyldithiophosphatotetracarbonylmanganese(I) and related compounds. Inorg Chem. 1966;5(7):1287-9.

Lawton et al., Myocardial oxygen consumption in the rabbit heart after ischemia: hyperpolarized arrest with pinacidil versus depolarized hyperkalemic arrest. Circulation. Nov. 4, 1997;96(9 Suppl):II-247-52.

Ledger, Carbon monoxide-releasing metal carbonyls: a new class of pharmaceuticals? Drug Disc Today. 2003;8:1096.

Lee et al., Heme oxygenase-1 mediates the anti-inflammatory effect of interleukin-10 in mice. Nat Med. Mar. 2002;8(3):240-6.

Levrand et al., Controlled release of volatile aldehydes and ketones by reversible hydrazone formation—classical profragrances are getting dynamic. Chem. Commun. 2006;28:2965-7.

Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90.

Lipmann et al., Organometallic Lewis Acids. LI. Reactivity of organometallic Lewis Acids (OC)4Re(OEt2)FBF3 and (OC)2(PPh3)2Ru(FBF3)2. Journal of Organometallic Chemistry. 1994;466(1-2):167-174. English abstract provided.

Loftsson et al., Cyclodextrins in topical drug formulations: theory and practice. Int J Pharm. Aug. 28, 2001;225(1-2):15-30. Review.

Lovell et al., Biologic agents for the treatment of juvenile rheumatoid arthritis: current status. Paediatr Drugs. 2004;6(3):137-46.

Mahmoud et al., Potential anticancer agents. XVI. Isolation of bicyclofarnesane sesquiterpenoids from Capsicodendron dinisii. J Nat Prod. May-Jun. 1980;43(3):365-71. Abstract only.

Maines, Heme oxygenase: function, multiplicity, regulatory mechanisms, and clinical applications. Faseb J. Jul. 1988;2(10):2557-68. Review.

Maines, The heme oxygenase system: a regulator of second messenger gases. Annu Rev Pharmacol Toxicol. 1997;37:517-54. Review.

Marks et al., Does carbon monoxide have a physiological function? Trends Pharmacol Sci. May 1991;12(5):185-8. Review.

Martins et al., Induction of carbon monoxide in the donor reduces graft immunogenicity and chronic graft deterioration. Transplant Proc. Jan.-Feb. 2005;37(1):379-81.

Matsuda et al., Mediators of non-adrenergic non-cholinergic inhibitory neurotransmission in porcine jejunum. Neurogastroenterol Motil. Oct. 2004;16(5):605-12.

Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.
McLaughlin et al., Potentiation of carbon monoxide-induced relaxation of rat aorta by YC-1 [3-(5'-hydroxymethyl-2'-furyl)-1-benzylindazole]. Can J Physiol Pharmacol. Apr. 2000;78(4):343-9.
McMillen et al., Hydrocarbon bond dissociation energies. Ann Rev Phys Chem. Oct. 1982;33:493-532.
Meder et al., Metallkomplexe mit biologisch wichtigen liganden, XLII [1] carbonylmetallkomplexe mit anionen von mehrfunktionellen alpha-aminosaeuren [Metal complexes with biologically important ligands], XLII [1] carbonyl metal complexes with anions of polyfunctional alpha-amino acids. Zeitschrift fur Naturforschung;1986:1247-54. German language reference. English abstract provided.
Megias et al., The carbon monoxide-releasing molecule tricarbonyldichlororuthenium(II) dimer protects human osteoarthritic chondrocytes and cartilage from the catabolic actions of interleukin-1beta. J Pharmacol Exp Ther. Apr. 2008;325(1):56-61. Epub Jan. 14, 2008.
Miguel et al., Manganese(I) complexes with (tricyclohexylphosphonio)dithiocarboxylate as chelate and unidentate ligand. X-Ray crystal structure of fac-[Mn(CO)3{S2CP(C6H11)3}2]ClO4oH20. J Chem Soc, Dalton Trans. 1987;12:2875-80.
Mikuls et al., Benefit-risk assessment of infliximab in the treatment of rheumatoid arthritis. Drug Saf. 2003;26(1):23-32. Review. Abstract only.
Miller et al., The pharmacological activities of the metabolites of N-[(trimethylamineboryl)-carbonyl]-L-phenylalanine methyl ester. Met Based Drugs. 1996;3(5):219-26.
Moncada et al., Nitric oxide: physiology, pathophysiology, and pharmacology. Pharmacol Rev. Jun. 1991;43(2):109-42.
Moncada et al., The discovery of nitric oxide and its role in vascular biology. Br J Pharmacol. Jan. 2006;147 Suppl 1:S193-201.
Moore et al., Brief inhalation of low-dose carbon monoxide protects rodents and swine from postoperative ileus. Crit Care Med. Jun. 2005;33(6):1317-26.
Morita et al., Carbon monoxide controls the proliferation of hypoxic vascular smooth muscle cells. J Biol Chem. Dec. 26, 1997;272(52):32804-9.
Morita et al., Smooth muscle cell-derived carbon monoxide is a regulator of vascular cGMP. Proc Natl Acad Sci U S A. Feb. 28, 1995;92(5):1475-9.
Morse et al., Suppression of inflammatory cytokine production by carbon monoxide involves the JNK pathway and AP-1. J Biol Chem. Sep. 26, 2003;278(39):36993-8. Epub Jul. 11, 2003.
Motterlini et al., Bioactivity and pharmacological actions of carbon monoxide-releasing molecules. Curr Pharm Des. 2003;9(30):2525-39.
Motterlini et al., Carbon monoxide-releasing molecules: characterization of biochemical and vascular activities. Circ Res. Feb. 8, 2002;90(2):E17-24.
Motterlini et al., Chapter 16: Studies on the development of carbon-monoxide-releasing molecules: potential applications for the treatment of cardiovascular dysfunction. Ed., Rui Wang. CRC Press, New York. 2002:249-72.
Motterlini et al., Characterization of vasoactive effects elicited by carbon monoxide-releasing molecules. Abstracts 8th Intl Symposium on Mechanisms of Vasodilation. J Vasc Res. May 31-Jun. 3, 2001;055.
Motterlini et al., CORM-A1: a new pharmacologically active carbon monoxide-releasing molecule. FASEB J. Feb. 2005;19(2):284-6. Epub Nov. 19, 2004.
Motterlini et al., Functional and metabolic effects of propionyl-L-carnitine in the isolated perfused hypertrophied rat heart. Mol Cell Biochem. Oct. 21, 1992;116(1-2):139-45.
Motterlini et al., Heme oxygenase-l-derived carbon monoxide contributes to the suppression of acute hypertensive responses in vivo. Circ Res. Sep. 7, 1998;83(5):568-77.
Motterlini et al., Therapeutic applications of carbon monoxide-releasing molecules. Expert Opin Investig Drugs. Nov. 2005;14(11):1305-18. Review.
Motterlini, Vasoactive properties of carbon monoxide-releasing molecules. Biomed Pharmacother. 2002;56(7):349-50.
Moya et al., Metal carbonyl complexes containing heterocyclic nitrogen ligands: Part IX. MnBr(CO)3(3,3?-R-2,2?-biquinoline) compounds. Polyhedron. Mar. 1, 2002; 21(4):439-44. Abstract only.
Mungrue et al., From molecules to mammals: what's NOS got to do with it? Acta Physiol Scand. Oct. 2003;179(2):123-35. Review. Abstract only.
Musameh et al., Improved myocardial function after cold storage with preservation solution supplemented with a carbon monoxide-releasing molecule (CORM-3). J Heart Lung Transplant. Nov. 2007;26(11):1192-8.
Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.
Nagai et al., Unusual CO bonding geometry in abnormal subunits of hemoglobin M Boston and hemoglobin M Saskatoon. Biochemistry. Jul. 2, 1991;30(26):6495-503.
Nakao et al., Carbon monoxide inhalation protects rat intestinal grafts from ischemia/reperfusion injury. Am J Pathol. Oct. 2003;163(4):1587-98.
Nakao et al., Protective effect of carbon monoxide in transplantation. J Cell Mol Med. Jul.-Sep. 2006;10(3):650-71. Review.
Ndisang et al., Modulation of the immunological response of guinea pig mast cells by carbon monoxide. Immunopharmacology. Jun. 1999;43(1):65-73.
Neto et al., Protection of transplant-induced renal ischemia-reperfusion injury with carbon monoxide. Am J Physiol Renal Physiol. Nov. 2004;287(5):F979-89. Epub Aug. 3, 2004.
Nitschke et al., Properties of (trifluoromethanesulfonato)pentacarbonylmanganese(I) and -rhenium(I). Reactions in superacid solvents. Inorg Chem. 1985;24(13):1972-8.
Nobre et al., Antimicrobial action of carbon monoxide-releasing compounds. Antimicrob Agents Chemother. Dec. 2007;51(12):4303-7. Epub Oct. 8, 2007.
Nudelman et al., Prodrugs of butyric acid. Novel derivatives possessing increased aqueous solubility and potential for treating cancer and blood diseases. Eur J Med Chem. Jan. 2001;36(1):63-74. Abstract only.
Nudelman et al., The role of intracellularly released formaldehyde and butyric acid in the anticancer activity of acyloxyalkyl esters. J. Med. Chem.. Jan. 22, 2005;48(4):1042-54. Abstract only.
Nydegger et al., New concepts in organ preservation. Transpl Immunol. May 2002;9(2-4):215-25.
O'Brien et al., Aldehyde sources, metabolism, molecular toxicity mechanisms, and possible effects on human health. Crit Rev Toxicol. Aug. 2005;35(7):609-62. Review.
Otterbein et al., Carbon monoxide has anti-inflammatory effects involving the mitogen-activated activated protein kinase pathway. Nat Med. Apr. 2000;6(4):422-8.
Otterbein et al., Carbon monoxide provides protection against hyperoxic lung injury. Am J Physiol. Apr. 1999;276(4 Pt 1):L688-94.
Otterbein et al., Carbon monoxide suppresses arteriosclerotic lesions associated with chronic graft rejection and with balloon injury. Nat Med. Feb. 2003;9(2):183-90. Epub Jan. 21, 2003.
Otterbein et al., Exogenous administration of heme oxygenase-1 by gene transfer provides protection against hyperoxia-induced lung injury. J Clin Invest. Apr. 1999;103(7):1047-54.
Otterbein et al., Heme oxygenase-1: unleashing the protective properties of heme. Trends Immunol. Aug. 2003;24(8):449-55. Review.
Otterbein, Carbon monoxide: innovative anti-inflammatory properties of an age-old gas molecule. Antioxid Redox Signal. Apr. 2002;4(2):309-19. Review.
Ozawa et al., Leydig cell-derived heme oxygenase-1 regulates apoptosis of premeiotic germ cells in response to stress. J Clin Invest. Feb. 2002;109(4):457-67.
Pae et al., Carbon monoxide produced by heme oxygenase-1 suppresses T cell proliferation via inhibition of IL-2 production. J Immunol. Apr. 15, 2004;172(8):4744-51.

Paintner et al., Synthesis and antimicrobial activity of tetrodecamycin partial structures. Bioorg Med Chem. Jul. 3, 2003;11(13):2823-33. Abstract only.

Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.

Patel et al., Preparation of (η5-cyclopentadienyl) and (η5-Methylcyclopentadienyl)Fe(CO)2Me cyclodextrin inclusion compounds and their subsequent ligand substitution reactions. Attempts at cyclodextrin mediated enantioselective ligand substitution. J Organometal Chem. 1997;547:103-112.

Peloso et al., Expanding the armamentarium for the spondyloarthropathies. Arthritis Res Ther. 2004;6 Suppl 2:S36-43. Epub Jun. 21, 2004.

Piantadosi, Biological chemistry of carbon monoxide. Antioxid Redox Signal. Apr. 2002;4(2):259-70. Review.

Pneumatikakis et al., Interactions of bis-[μ-chloro-chlorotricarbonylruthenium(II) and poly-[μ-dichloro-dicarbonylruthenium (II)] with nucleotides. Inorg Chemica Acta. 1988;151:243-8.

Quick et al., Pentacarbonytmanganese halides. In Inorganic Syntheses, vol. 19. Duward F. Shriver., Ed. Inorganic Syntheses, Inc. 1979:158-63.

Rattan et al., Mechanism of internal anal sphincter relaxation by CORM-1, authentic CO, and NANC nerve stimulation. Am J Physiol Gastrointest Liver Physiol. Sep. 2004;287(3):G605-11.

Rehder et al., 55Mn NMR characteristics of carbonylmanganese complexes with hetero-substituted dithioformato-, thioformamido- and thioformamide ligands [1]. Inorg Chim Acta. 1983;73:243-7. Abstract only.

Reimann et al., Reactions of metal carbonyls. Part III. Steric and stereochemical limitations of higher substitution of manganese carbonyl bromide. J Chem Soc Dalton Trans. 1973;841-6. Abstract only.

Rodella et al., Carbon monoxide and biliverdin prevent endothelial cell sloughing in rats with type I diabetes. Free Radic Biol Med. Jun. 15, 2006;40(12):2198-205. Epub Mar. 20, 2006.

Rutkowska-Zbik et al., Theoretical density functional theory studies on interactions of small biologically active molecules with isolated heme group. J Comput Chem. Mar. 2007;28(4):825-31.

Ryan et al., Renal vascular responses to CORM-A1 in the mouse. Pharmacol Res. Jul. 2006;54(1):24-9. Epub Mar. 9, 2006.

Ryter et al., Carbon monoxide in biology and medicine. Bioessays. Mar. 2004;26(3):270-80.

Ryter et al., Carbon monoxide: to boldly go where NO has gone before. Sci STKE. Apr. 20, 2004;2004(230):RE6. Review.

Ryter et al., Heme oxygenase-1/carbon monoxide: from basic science to therapeutic applications. Physiol Rev. Apr. 2006;86(2):583-650. Review.

Ryter et al., Heme oxygenase/carbon monoxide signaling pathways: regulation and functional significance. Mol Cell Biochem. May-Jun. 2002;234-235(1-2):249-63. Review.

Sacerdoti et al., Treatment with tin prevents the development of hypertension in spontaneously hypertensive rats. Science. Jan. 20, 1989;243(4889):388-90.

Sacks et al., Comparative bioavailability of elemental iron powders for repair of iron deficiency anemia in rats. Studies of efficacy and toxicity of carbonyl iron. Am J Clin Nutr. Apr. 1978;31(4):566-71.

Salazar-Salinas et al., Molecular biosensor based on a coordinated iron complex. J Chem Phys. Mar. 14, 2009;130(10):105101.

Sammut et al., Carbon monoxide is a major contributor to the regulation of vascular tone in aortas expressing high levels of haeme oxygenase-1. Br J Pharmacol. Dec. 1998;125(7):1437-44.

Sandborn, Strategies for targeting tumour necrosis factor in IBD.Best Pract Res Clin Gastroenterol. Feb. 2003;17(1):105-17. Review.

Sandouka et al., Carbon monoxide-releasing molecules (CO-RMs) modulate respiration in isolated mitochondria. Cell Mol Biol (Noisy-le-grand). Sep. 30, 2005;51(4):425-32.

Sandouka et al., Treatment with CO-RMs during cold storage improves renal function at reperfusion. Kidney Int. Jan. 2006;69(2):239-47.

Sarady et al., Carbon monoxide protection against endotoxic shock involves reciprocal effects on iNOS in the lung and liver. FASEB J. May 2004;18(7):854-6. Epub Mar. 4, 2004.

Sato et al., Carbon monoxide generated by heme oxygenase-1 suppresses the rejection of mouse-to-rat cardiac transplants. J Immunol. Mar. 15, 2001;166(6):4185-94.

Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.

Sawle et al., Homocysteine attenuates endothelial haem oxygenase-1 induction by nitric oxide (NO) and hypoxia. FEBS Lett. Nov. 23, 2001;508(3):403-6.

Schmidt et al., Manganese(I) and rhenium(I) pentacarbonyl(Trifluoromethanesulfatonato) complexes. In Inorganic Syntheses, Ed. Herbert D. Kaesz. Inorganic Syntheses, Inc. 1989:113-7.

Schubert, The action of carbon monoxide on iron and cobalt complexes of cysteine. Carbon Monixide on Iron and Cobalt Cysteine Complexes. 1933;55:4563-70.

Severin et al., Metal complexes of biologically important ligands. LXX. Synthesis, stereochemistry and reactions of ruthenium (II) and osmium (II) complexes with .alpha.-amino carboxylates. 1994; 127(4): 615-620. English abstract provided.

Shiohira et al., Protective effect of carbon monoxide donor compounds in endotoxin-induced acute renal failure. Am J Nephrol. 2007;27(5):441-6. Epub Jul. 12, 2007.

Silver et al., Mossbauer studies on protoprophyrin IX iron (II) solutions containing sulphur ligands and their carbonyl adducts. Inorg Chimica Acta. 1984;9:279-83.

Sjöstrand, Endogenous formation of carbon monoxide in man under normal and pathological conditions. Scan J Clin Lab Invest. 1949;1:201-14.

Skattebøl et al., Synthesis of (±)-Lineatin, an aggregation pheromone component of Trypodendron lineatum. Acta Chem Scand B. 1985;39:291-304.

Soares et al., Expression of heme oxygenase-1 can determine cardiac xenograft survival. Nat Med. Sep. 1998;4(9):1073-7.

Song et al., Carbon monoxide inhibits human airway smooth muscle cell proliferation via mitogen-activated protein kinase pathway. Am J Respir Cell Mol Biol. Nov. 2002;27(5):603-10.

Song et al., Carbon monoxide inhibits T lymphocyte proliferation via caspase-dependent pathway. J Immunol. Jan. 15, 2004;172(2):1220-6.

Spector, Review: Oxidative stress and disease. J Ocul Pharmacol Ther. Apr. 2000;16(2):193-201. Review. Abstract only.

Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.

Srisook et al., Role of NO in enhancing the expression of HO-1 in LPS-stimulated macrophages. Methods Enzymol. 2005;396:368-77.

Staal et al., The syntheses and coordination properties of M(CO)3X(DAB) (M=Mn, Re; X=CI, Br, I; DAB=1,4-diazabutadiene). J Organometal Chem. May 1, 1979:170(2):235-45. Abstract only.

Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.

Stanford et al., Carbon monoxide inhibits endothelin-1 release by human pulmonary artery smooth muscle cells. Eur J Pharmacol. Feb. 23, 2004;486(3):349-52.

Stanford et al., Heme oxygenase is expressed in human pulmonary artery smooth muscle where carbon monoxide has an anti-proliferative role. Eur J Pharmacol. Jul. 25, 2003;473(2-3):135-41.

Stec et al., Heme oxygenase-1 induction does not improve vascular relaxation in angiotensin II hypertensive mice. Am J Hypertens. Feb. 2008;21(2):189-93. Epub Jan. 3, 2008.

Stein et al., Administration of a CO-releasing molecule induces late preconditioning against myocardial infarction. J Mol Cell Cardiol. Jan. 2005;38(1):127-34. Epub Dec. 8, 2004.

Stone et al., Soluble guanylate cyclase from bovine lung: activation with nitric oxide and carbon monoxide and spectral characterization of the ferrous and ferric states. Biochemistry. May 10, 1994;33(18):5636-40.

Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

Suematsu et al., Carbon monoxide: an endogenous modulator of sinusoidal tone in the perfused rat liver. J Clin Invest. Nov. 1995;96(5):2431-7.

Sun et at, Attenuation of leukocytes sequestration by carbon monoxide-releasing molecules: liberated carbon monoxide in the liver of thermally injured mice. J Burn Care Res. Jan.-Feb. 2007;28(1):173-81.

Sun et al., CO-releasing molecules (CORM-2)-liberated CO attenuates leukocytes infiltration in the renal tissue of thermally injured mice. Int J Biol Sci. Jun. 16, 2008;4(3):176-83.

Sun et al., Preconditioning of carbon monoxide releasing molecule-derived CO attenuates LPS-induced activation of HUVEC. Int J Biol Sci. Aug. 22, 2008;4(5):270-8.

Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.

Suzuki et al., Activated platelets in ulcerative colitis enhance the production of reactive oxygen species by polymorphonuclear leukocytes. Scand J Gastroenterol. Dec. 2001;36(12):1301-6. Abstract only.

Szakács-Schmidt et al., Iron (II) thiolates as reversible carbon monoxide carriers. Inorg Chimica Acta. 1992;198-200:401-5.

Szallasi et al., Dialdehyde sesquiterpenes and other terpenoids as vanilloids. Eur J Pharmacol. Aug. 28, 1998;356(1):81-9. Abstract only.

Taillé et al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.

Takács et al., Synthesis and molecular structure of carbonyl derivatives of Iron (II) thiolates containing nitrogen-donor ligands. Inorg Chemica Acta. 1989;166:39-46.

Tamaki, Role of second messenger gases in ischemia and reperfusion injury. Low Temp Med. 2001;27(1):1-5. English abstract provided.

Tayem et al., Protection against cisplatin-induced nephrotoxicity by a carbon monoxide-releasing molecule. Am J Physiol Renal Physiol. Apr. 2006;290(4):F789-94. Epub Nov. 15, 2005.

Tenhunen et al., Microsomal heme oxygenase. Characterization of the enzyme. J Biol Chem. Dec. 10, 1969;244(23):6388-94.

Tilg et al., Antitumour necrosis factor therapy in Crohn's disease. Expert Opin Biol Ther. Oct. 2002;2(7):715-21. Review. Abstract only.

Tomita et al., Structure and reaction of bis(L-cysteinato)dicarbonyliron(II). Inorg Nucl Chem Lett. 1968;4:715-8.

Treichel et al., Synthesis and reactivity of bridging thiolato-manganese carbonyl complexes, Et4N[Mn2(μ-SR)3(CO)6]. J Organometall Chem. Sep. 10, 1985;292(3):385-93.

Tsuburai et al., The role of heme oxygenase in pulmonary circulation. Low Temp Med. 2001;27(1):25-35. English abstract provided.

Urban et al., Metal complexes of biologically important ligands, LXXXVII α-amino carboxylate complexes of palladium(II), iridium(III) and ruthenium(II) from chloro-bridged ortho-metallated metal compounds and [(OC)3Ru(CI)(μ-C1)]2. J Organomett Chem. 1996;517:191-200.

Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.

Van Staveren et al., Spectroscopic Properties, Electrochemistry, and Reactivity of MoO, MoI, and MoII Complexes with the [Mo(bpa)(CO)3] Unit [bpa=bis(2-picolyl)amine] and Their Application for the Labelling of Peptides. Eur J Inorg Chem. 2002;6:1518-29.

Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.

Vannacci et al., The effect of a carbon monoxide-releasing molecule on the immunological activation of guinea-pig mast cells and human basophils. Inflamm Res. 2004;53 Suppl 53:S09-10.

Varadi et al., Beneficial effects of carbon monoxide-releasing molecules on post-ischemic myocardial recovery. Life Sci. Apr. 3, 2007;80(17):1619-26. Epub Feb. 2, 2007.

Vera et al., Protective effect of carbon monoxide-releasing compounds in ischemia-induced acute renal failure. J Am Soc Nephrol. Apr. 2005;16(4):950-8. Epub Feb. 23, 2005.

Verma et al., Carbon monoxide: a putative neural messenger. Science. Jan. 15, 1993;259(5093):381-4.

Verona et al., Regioselectivity in the nucleophilic functionalization of xanthene complexes of Mn(CO)3. J Organelle Chem. Nov. 1, 1996;524(1-2)71-80.

Viswanathamurthi et al., Synthesis, characterization and biocidal studies of ruthenium (II) carbonyl complexes containing tetradentate Schiff bases. Transition Metal Chemistry. 1999; 24(6):638-641.

Volti et al., Carbon monoxide signaling in promoting angiogenesis in human microvessel endothelial cells. Antiox Redox Signal. May 2005;7(5-6):704-10.

Vreman et al., Determination of carbon monoxide (CO) in rodent tissue: effect of heme administration and environmental CO exposure. Anal Biochem. Jun. 15, 2005;341(2):280-9. Abstract only.

Vulapalli et al., Cardioselective overexpression of HO-1 prevents I/R-induced cardiac dysfunction and apoptosis. Am J Physiol Heart Circ Physiol. Aug. 2002;283(2):H688-94.

Waibel et al., Stable one-step technetium-99m labeling of His-tagged recombinant proteins with a novel Tc(I)-carbonyl complex. Nat Biotechnol. Sep. 1999;17(9):897-901.

Wang et al., A correlation of the visible and Soret spectra of dioxygen- and carbon monoxide-heme complexes and five-coordinate heme complexes with the spectra of oxy-, carboxy-, and deoxyhemoglobins. Biochemistry. Oct. 30, 1979;18(22):4960-77.

Wang et al., Carbon monoxide-induced vasorelaxation and the underlying mechanisms. Br J Pharmacol. Jul. 1997;121(5):927-34.

Wang et al., Preconditioning limits mitochondrial Ca(2+) during ischemia in rat hearts: role of K(ATP) channels. Am J Physiol Heart Circ Physiol. May 2001;280(5):H2321-8.

Wang et al., The chemical modification of KCa channels by carbon monoxide in vascular smooth muscle cells. J Biol Chem. Mar. 28, 1997;272(13):8222-6.

Weigel et al., Inhibition of DNA replication in *Escherichia coli* by cyanide and carbon monoxide. J Biol Chem. Nov. 10, 1975;250(21):8536-42.

Willis et al., Heme oxygenase: a novel target for the modulation of the inflammatory response. Nat Med. Jan. 1996;2(1):87-90.

Wu et al., Carbon monoxide: endogenous production, physiological functions, and pharmacological applications. Pharmacol Rev. Dec. 2005;57(4):585-630. Review.

Wu et al., Different mechanisms underlying the stimulation of K(Ca) channels by nitric oxide and carbon monoxide. J Clin Invest. Sep. 2002;110(5):691-700.

Xi et al., Carbon monoxide activates KCa channels in newborn arteriole smooth muscle cells by increasing apparent Ca2+ sensitivity of alpha-subunits. Am J Physiol Heart Circ Physiol. Feb. 2004;286(2):H610-8. Epub Oct. 16, 2003.

Xu et al., A facile method for synthesis of (R)-(-)- and (S)-(+)-homocitric acid lactones and related a-hydroxy dicarboxylic acids from d- or l-malic acid. Tetrahedron Lett. May 30, 2005;46(22):3815-18. Abstract only.

Yachie et al., Oxidative stress causes enhanced endothelial cell injury in human heme oxygenase-1 deficiency. J Clin Invest. Jan. 1999;103(1):129-35.

Yan et al., Cytotoxicity of rhenium(I) alkoxo and hydroxo carbonyl complexes in murine and human tumor cells. Pharmazie. Apr. 2000;55(4):307-13.

Yet et al., Cardiac-specific expression of heme oxygenase-1 protects against ischemia and reperfusion injury in transgenic mice. Circ Res. Jul. 20, 2001;89(2):168-73.

Yet et al., Induction of heme oxygenase-1 expression in vascular smooth muscle cells. A link to endotoxic shock. J Biol Chem. Feb. 14, 1997;272(7):4295-301.

Zhang et al., Carbon monoxide inhibition of apoptosis during ischemia-reperfusion lung injury is dependent on the p38 mitogen-activated protein kinase pathway and involves caspase 3. J Biol Chem. Jan. 10, 2003;278(2):1248-58. Epub Oct. 23, 2002.

Zimmerman et al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

* cited by examiner

METHODS FOR TREATING INFLAMMATORY DISEASE BY ADMINISTERING ALDEHYDES AND DERIVATIVES THEREOF

CROSS-REFERENCE TO RELATED APPLICATIONS

This application is a continuation-in-part of U.S. patent application Ser. No. 11/288,670, filed on Nov. 29, 2005, and U.S. Ser. No. 11/453,319, filed on Jun. 14, 2006, both of which claim priority to U.S. Pat. No. 7,011,854, filed on Feb. 3, 2003, which claims priority to U.S. Provisional Patent Application No. 60/353,233, filed on Feb. 4, 2002. This application also claims priority to U.S. Provisional Patent Application No. 60/873,155 filed Dec. 6, 2006. All of these priority applications are incorporated herein by reference.

BACKGROUND

1. Field

The field relates to organic aldehydes and derivatives thereof, and in particular to methods of administering pharmaceutical compositions containing such compounds to treat inflammatory diseases.

2. Description of the Related Art

Many acute and chronic inflammatory diseases are thought to be caused by pathological immune responses. Tissue injury caused by ischemia, reperfusion or physical trauma is aggravated by inflammatory reactions. The natural resolution of inflammation is often incomplete, leading to chronic pathological conditions associated with pain and functional impairment of the affected tissues. Although many drugs in present use reduce pain and inflammatory damage, there is still an urgent need for better treatments for a wide variety of inflammatory diseases.

Rheumatoid arthritis is a well known example of an inflammatory disease for which improved treatments are needed (Saravanan et al., *Expert Opin. Pharmacother.* 3:845-56 (2002); O'Dell, *N. Engl. J Med.* 350:2591-602 (2004)). Typically, rheumatoid arthritis patients are first treated with non-steroidal anti-inflammatory drugs (NSAIDs), such as aspirin, indomethacin, ibuprofen and many others (Steinmeyer, *J. Arthritis Res.* 2:379-85 (2000)). These drugs inhibit the first step of prostaglandin synthesis by competitively inhibiting the enzymes cyclooxygenase 1 and 2 (COX-1 and COX-2). In general, NSAIDs provide only symptomatic relief from the pain and inflammation associated with the disease, and do not arrest the progression of pathological injury to the joints. Moreover, the use of these drugs is limited by side effects, in particular gastrointestinal ulcers that are thought to be caused by the inhibition of COX-1. More recently developed selective COX-2 inhibitors have fewer gastrointestinal side effects, but increase the risk of myocardial infarction (Ardoin et al., *Curr. Opin. Rheumatol.* 18:221-226 (2006)).

In contrast to NSAIDs, glucocorticoids are potent suppressors of immune responses and inflammation. However, the continued use of glucocorticoids at supraphysiological doses is associated with many adverse effects, some of which are severe, such as hypertension, increased susceptibility to infections, osteoporosis, growth arrest and behavioural disturbances. Withdrawal from corticosteroid therapy can lead to disease flare-up and also acute adrenal insufficiency.

Several other drugs that are able to reduce the progression of rheumatoid arthritis, at least in some patients, are collectively referred to as disease modifying anti-rheumatic drugs (DMARDs). Examples include methotrexate, chloroquine, sulfasalazine, gold salts, D-penicillamine, azathioprine, leflunomide and cyclosporine. DMARDs are now often used earlier in the course of disease (Scott, *Arthritis Res. Ther.* 6:15-8 (2004)). While these drugs may arrest or reduce the progression of joint destruction, they have a variety of adverse effects, some of which may be severe, leading to the withdrawal of the drug from the treatment schedule.

Recently, a significant improvement in the treatment of rheumatoid arthritis has been achieved with a novel class of DMARDs often referred to as biologics (Olsen et al., *N. Engl. J. Med.* 350:2167-2179 (2004)). Biologics are therapeutically effective proteins that are engineered and expressed using recombinant DNA technologies. Some important biologics currently used for the treatment of rheumatoid arthritis are tumor necrosis factor (TNF) neutralizing antibodies and TNF receptor constructs. These new anti-rheumatic drugs have a quicker onset of action than the traditional DMARDs, and suppress the progression of joint erosions. However, this class of drugs must be parenterally administered and is quite costly. Moreover, extended use of TNF neutralizing biologics has revealed adverse effects, such as reactivation of tuberculosis, increased susceptibility to infections, and an increased risk for development of malignant diseases (Mikuls et al., *Drug Saf.* 26:23-32 (2003)).

Because of the shortcomings of the existing drugs used for treating rheumatoid arthritis and other inflammatory diseases, extensive efforts are being made by the pharmaceutical and biotechnology industries to develop novel treatment modalities that are safe and effective (Kumar et al., *Nat. Rev. Drug Discov.* 2:717-26 (2003); Adcock, *Drug Discovery Today: Therapeutic Strategies,* 1:321-9 (2004); Smith, *Drug Discovery Today* 10:1598-1606 (2005)). One molecule that has been identified as potentially useful in treating inflammatory disease is carbon monoxide. Carbon monoxide (CO) is an endogenous metabolite with pleiotropic effects that are integrated into adaptive responses of the body to various types of stress (Ryter et al., *Bioessays,* 26: 270-80 (2004)). CO inhibits TNF production in vitro and in vivo, and has shown impressive anti-inflammatory effects in animal models (Otterbein, *Antioxid. Redox. Signal.* 4:309-319 (2002); Ryter et al., *Bioessary* 26:270-280 (2004)). In addition to inhibiting TNF production, CO has other anti-inflammatory effects. It inhibits the production of other pro-inflammatory cytokines, such as IL-1, IL-6 and MIP-1 (Otterbein et al., *Nat. Med.* 6:422-428 (2000); Morse et al., *J. Biol. Chem.* 278:36993-36998 (2003)), enhances IL-10 production (Otterbein et al., *Nat. Med.* 6:422-428 (2000)), inhibits excessive NO production by inducible nitric oxide synthase (Sarady et al., *Faseb J.* 18:854-856 (2004)), inhibits mast cell activation (Ndisang et al., *Immunopharmacol.* 43:65-73 (1999)), and modulates immune responses (Song et al., *J. Immunol.* 172:1220-1226 (2004)).

Often, however, endogenous carbon monoxide (CO) does not provide its full potential of beneficial effects, because its production is delayed or reduced under pathological conditions. Thus, therapeutic effects may be achieved by administration of exogenous carbon monoxide. Exogenous CO may also induce the expression of hemoxygenase-1 (HO-1) (Sawle et al., *Br. J. Pharmacol.* 145(6):800-810 (2005); Lee et al., *Nat. Med.* 8:240-246 (2002)). HO-1 is known to have a wide variety of protective functions (Otterbein et al., *Trends Immunol.* 24:449-455 (2003)), most of which are mediated by its products CO and biliverdin/bilirubin. Thus, the beneficial effects of exogenous CO may be further augmented by the induction of endogenous CO and biliverdin/bilirubin production.

Indeed, treatment of animals by inhalation of carbon monoxide has revealed beneficial effects in a variety of disease models. However, systemic delivery of carbon monoxide via the lung is not practical outside of hospitals, and is limited by the requirement for doses that are near toxic levels. Limitations of carbon monoxide inhalation therapy may be overcome by the use of carbon monoxide releasing molecules, also known as CORMs (Motterlini et al., *Curr. Pharm. Des.* 9:2525-39 (2003)). Impressive therapeutic effects of CO used as a gas and CORMs have been achieved in animal models of inflammation (Sarady et al., *Faseb J.* 18:854-6 (2004); Zuckerbraun et al., *Am. J. Physiol. Gastrointest. Liver Physiol.* 289: G607-13 (2005); Sawle et al., *FEBSLett.* 508:403-6 (2001)), ischemia/reperfusion injury (Amersi et al., *Hepatology*, 35:815-23(2002); Nakao et al., *Am. J Pathol.* 163:1587-98 (2003); Zhang et al., *J. Biol. Chem.* 278:1248-58 (2003); Vera et al., *J. Am. Soc. Nephrol.* 16:950-8 (2005); Sandouka et al., *Kidney Int.* 69:239-47 (2006)), postoperative ileus (Moore et al., *Crit. Care Med.* 33:1317-26 (2005)), transplantation (Chauveau et al., *Am. J. Transplant.* 2:581-92 (2002); Clark et al., *Circ. Res.* 93:e2-8 (2003); Gunther et al., *Diabetes* 51:994-9 (2002); Akamatsu et al., *Faseb J.* 18:771-2 (2004); Martins et al., *Transplant. Proc.* 37:379-81(2005)), atherosclerosis (Otterbein et al., *Nat. Med.* 9:183-90 (2003)), restenosis (Otterbein et al., *Nat. Med.* 9:183-90 (2003)), myocardial infarction (Stein et al., *J. Mol. Cell. Cardiol.* 38:127-34 (2005); Guo et al., *Am. J. Physiol. Heart Circ. Physiol.* 286:H1649-53 (2004)) and pulmonary hypertension (Zuckerbraun et al., *J. Exp. Med.* 203:2109-19 (2006)).

While the potential advantage of CO delivery by CORMs over CO delivery by inhalation is generally recognized, the identification of CORMs which selectively deliver CO to therapeutic targets remains a challenge in the development of CORMs as drugs. Selective delivery of CO to diseased tissues may be achieved by using compounds that release CO in the presence of reactive oxygen species, which are generated at high levels under many pathological conditions. Reactive oxygen species (ROS) include, without limitation, oxygen ions, superoxide, peroxynitrite, free radicals and peroxides, both inorganic and organic. A variety of highly reactive ROS are generated from superoxide (Hogg, *Semin. Reprod. Endocrinol.* 16:241-8 (1998)). These molecules are generated at low levels in many tissues, and have important roles in various signal transduction pathways (Droge, *Physiol. Rev.,* 82:47-95 (2002)). However, excessive production of ROS occurs in many pathological conditions. While a variety of mechanisms have evolved to prevent damage by excessive amounts of ROS, conditions in which production of these highly reactive molecules exceeds the capacity to neutralize them are referred to as oxidative stress. "Oxidative stress" is a medical term for the damage to animal or plant cells caused by reactive oxygen species.

Oxidative stress is a hallmark of many diseases (Spector, *J. Ocul Pharmacol Ther.* 2:193-201(2000)). These include inflammatory diseases, such as rheumatoid arthritis (Bauerova et al., *Gen. Physiol. Biophys.* 18 Spec No: 15-20 (1999); Hadjigogos, *Panminerva Med.* 45:7-13 (2003); Hitchon et al., *Arthritis Res. Ther.* 6:265-78 (2004)), asthma (Andreadis et al., *Free Radic. Biol. Med.* 35:213-25 (2003); Henricks et al., *Pulm. Pharmacol. Ther.* 14:409-20 (2001)), ulcerative colitis (Suzuki et al., *Scand. J. Gastroenterol.* 36:1301-6 (2001)), and diseases associated with chronic inflammatory reactions, such atherosclerosis and neurodegenerative diseases (Beal, *Free Radic. Biol. Med.* 32:797-803 (2002)), and/or with ischemia/reperfusion injury, such as myocardial infarction (Frangogiannis et al., *Cardiovasc. Res.* 53:31-47(2002)), stroke, sleep apnea and transplantation. New CORM compositions that release CO in the presence of reactive oxygen species would be useful for treating inflammatory diseases such as these.

SUMMARY

Disclosed herein are methods of treating inflammatory disease in an animal by administering a pharmaceutical composition containing an organic aldehyde or its derivative. The aldehydes exhibit anti-inflammatory properties, at least in part by release of carbon monoxide (CO) in normal or inflamed tissues, or both. In some instances, an aldehyde is administered in the form of a derivative, e.g., in a protected form that provides, for example, improved in vivo stability, bioavailability, and/or delivery in vivo.

Accordingly, one aspect provides a method for treating inflammatory disease. The method includes administering to an animal in need thereof a pharmaceutical composition including an anti-inflammatory effective amount of an organic aldehyde compound or a derivative thereof in a pharmaceutically acceptable vehicle. The organic aldehyde releases CO in the animal, thereby providing an anti-inflammatory effect.

In certain embodiments, the organic aldehyde is a compound of formula I:

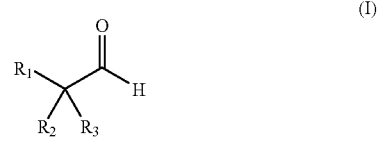

(I)

wherein $R_1$, $R_2$ and $R_3$ are each independently selected from alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or two or more of $R_1$, $R_2$ and $R_3$ are taken together to form a substituted or unsubstituted carbocyclic or heterocyclic ring structure.

In some embodiments, $R_1$, $R_2$ and $R_3$ are each independently selected from alkyl, substituted alkyl, cycloalkyl, substituted cycloalkyl, alkenyl, and substituted alkenyl. In some such embodiments, the compound of formula I is trimethylacetaldehyde, 2,2-dimethyl-4-pentenal, 4-ethyl-4-formylhexanenitrile, 3-hydroxy-2,2-dimethylpropanal, 2-formyl-2-methyl-propylmethanoate or 2-ethyl-2-methyl-propionaldehyde.

In other embodiments, $R_1$ and $R_2$ are each independently selected from alkyl, substituted alkyl, cycloalkyl, substituted cycloalkyl, alkenyl, and substituted alkenyl, and $R_3$ is selected from aryl, substituted aryl, heteroaryl, substituted heteroaryl, alkylaryl, and substituted alkylaryl. In some such embodiments, the compound of formula I is 2,2-dimethyl-3-(p-methylphenyl)propanal or 2-methyl-2-phenylpropionaldehyde.

In certain embodiments, a derivative of a compound of formula I is employed. In some embodiments, the derivative is an acetal, hemiacetal, aminocarbinol, aminal, imine, enaminone, imidate, amidine, iminium salt, sodium bissulfite adduct, hemimercaptal, dithioacetal, 1,3-dioxepane, 1,3-dioxane, 1,3-dioxalane, 1,3-dioxetane, α-hydroxy-1,3-dioxepane, α-hydroxy-1,3-dioxane, α-hydroxy-1,3-dioxalane, α-keto-1,3-dioxepane, α-keto-1,3-dioxane, α-keto-1,3-dioxalane, α-keto-1,3-dioxetane, macrocyclic ester/imine, macrocyclic ester/hemiacetal, oxazolidine, tetrahydro-1,3-oxazine, oxazolidinone, tetrahydro-oxazinone, 1,3,4-oxadiazine, thiazolidine, tetrahydro-1,3-thiazine, thiazolidinone, tetrahydro-1,3-thiazinone, imidazolidine, hexahydro-1,3-pyrimidine, imidazolidinone, tetrahydro-1,3-pyrimidinone, oxime, hydrazone, carbazone, thiocarbazone, semicarbazone, semithiocarbazone, acyloxyalkyl ester derivative, O-acyloxyalkyl derivative, N-acyloxyalkyl derivative, N-Mannich base derivative or N-hydroxymethyl derivative. In some such embodiments, the derivative is an oxazolidine, thiazolidine, imidazolidinone or oxazolidinone.

In some embodiments, the compound of formula I is linked to an amino acid or protein. In certain embodiments, the compound of formula I or derivative thereof is administered concomitantly with a second anti-inflammatory agent. In certain embodiments, the compound of formula I or derivative thereof is administered in the form of a pharmaceutically acceptable salt.

In some embodiments, the pharmaceutical composition is a tablet, dragee, capsule, pill, powder, troche or granule. In other embodiments, the pharmaceutical composition is a suspension, emulsion, solution, syrup or elixir. In still other embodiments, the pharmaceutical composition is formulated for parenteral administration.

In certain embodiments, the inflammatory disease is arthritis, for example, rheumatoid arthritis, juvenile idiopathic arthritis, osteoarthritis or psoriatic arthritis. In some embodiments, the inflammatory disease is Alzheimer's disease, Parkinson's disease, amyotrophic lateral sclerosis or multiple sclerosis. In certain embodiments, the inflammatory disease is an inflammatory lung disease. In some embodiments, the inflammatory disease is an inflammatory bowl disease. In certain embodiments, the inflammatory disease is an inflammatory skin disease. In some embodiments, the inflammatory disease is atherosclerosis, myocardial infarction, stroke or transplant rejection. In certain embodiments, the inflammatory disease is gram-positive or gram negative shock, sepsis, septic shock, hemorrhagic or anaphylactic shock or systemic inflammatory response syndrome.

BRIEF DESCRIPTION OF THE DRAWINGS

The following drawings are presented for the purpose of illustration only and are not intended to be limiting.

DETAILED DESCRIPTION

Figure 1A:
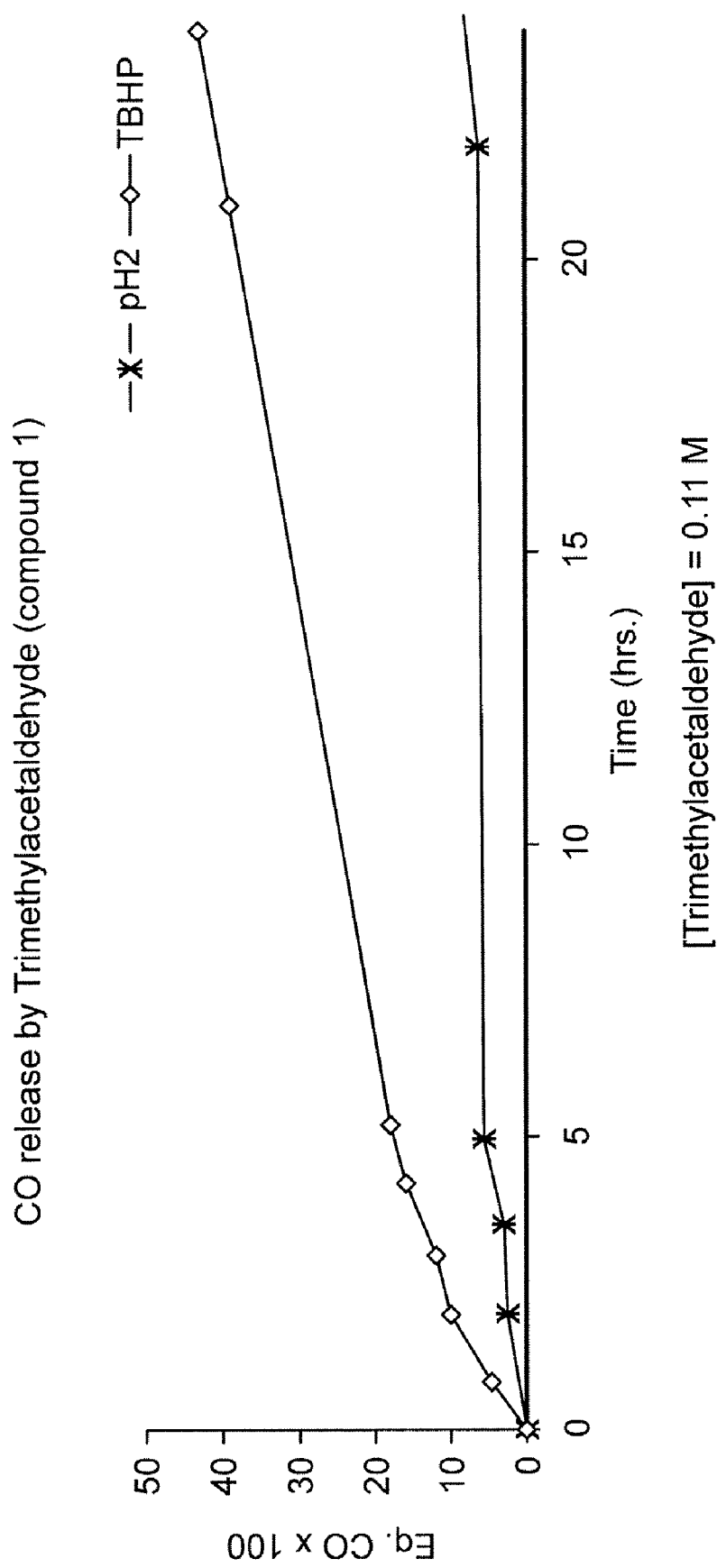
FIGS. 1A-D are plots showing the CO release behavior of trimethylacetaldehyde (compound 1) in TBHP and pH 2 solutions, and also the effects of concentrations of trimethylacetaldehyde and TBHP on the CO release.

All of the patent documents and literature references identified herein are incorporated by reference in their entirety.

Disclosed herein are methods for treating inflammatory disease in an animal by administering a pharmaceutical composition including an aldehyde compound or a derivative thereof. The therapeutic effects of these compounds are at least in part due to their ability to generate carbon monoxide (CO) under physiological or pathophysiological conditions. In at least some embodiments, CO is generated from the aldehydes or derivatives thereof by spontaneous release (i.e., release induced by the presence of reactive oxygen species, hydrolysis, pH variation, metabolic activation, or any other biological change that affects the chemical stability of the aldehyde, leading to decarbonylation) in normal or inflamed tissues, or both. In certain embodiments, the aldehydes or derivatives thereof generate CO exclusively or preferentially in the presence of reactive oxygen species (ROS), and thus are expected to have beneficial effects in diseases associated with oxidative stress.

Compounds for administration as disclosed herein include organic aldehydes of the general formula I:

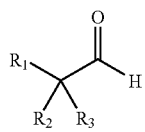

(I)

wherein $R_1$, $R_2$ and $R_3$ are each independently selected from H, alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or two or more of $R_1$, $R_2$ and $R_3$ are taken together to form a substituted or unsubstituted carbocyclic or heterocyclic ring structure.

The following definitions are used herein. "Alkyl" refers to straight or branched chain saturated hydrocarbyl groups having up to 20 carbon atoms, and "substituted alkyl" refers to alkyl groups bearing one or more substituents selected from amino, alkylamino, hydroxy, alkoxy, mercapto, alkylmercapto, aryl, aryloxy, alkoxycarbonyl, acyl, acyloxy, acylamino, F, Cl, Br, $NO_2$, cyano, sulfonyl, sufmyl and similar substituents known to those of skill in the art. "Cycloalkyl" refers to saturated hydrocarbyl groups containing one or more rings and having in the range of 3 to 12 carbon atoms, and "substituted cycloalkyl" refers to cycloalkyl groups further bearing one or more substituents as set forth above. "Heterocyclyl" refers to cyclic groups containing one or more rings including one or more heteroatoms (e.g., N, O or S) as part of the ring structure and having in the range of 3 to 12 ring atoms, and "substituted heterocyclyl" refers to heterocyclyl groups further bearing one or more substituents as set forth above. "Alkylheterocyclyl" refers to alkyl-substituted heterocyclyl groups, and "substituted alkylheterocyclyl" refers to alkylheterocyclyl groups further bearing one or more substituents as set forth above. "Alkenyl" refers to straight or branched chain hydrocarbyl groups having at least one carbon-carbon double bond, and having in the range of 2 to 20 carbon atoms, and "substituted alkenyl" refers to alkenyl groups further bearing one or more substituents as set forth above. "Aryl" refers to aromatic groups having in the range of 6 up to about 14 carbon atoms, and "substituted aryl" refers to aryl groups further bearing one or more substituents as set forth above. "Heteroaryl" refers to aromatic groups containing one or more heteroatoms (e.g., N, O or S) as part of the ring structure, and having in the range of 5 up to about 13 carbon atoms, and "substituted heteroaryl" refers to heteroaryl groups further bearing one or more substituents as set forth above. "Alkylaryl" refers to alkyl-substituted aryl groups, and "substituted alkylaryl" refers to alkylaryl groups further bearing one or more substituents as set forth above.

"Hydroxy" refers to the group OH. "Alkoxy" refers to a group —OR, wherein R is an alkyl group as defined above.

"Amino" refers to the group $NH_2$. "Alkylamino" refers to a group —NHR or —NRR', where R and R' are independently chosen from alkyl or cycloalkyl groups as defined above. "Mercapto" refers to the group SH. "Alkylmercapto" refers to the group S—R, where R represents an alkyl or cycloalkyl group as defined above. "Aryloxy" refers to a group —OAr, wherein Ar is an aryl group as defined above, and "substituted aryloxy" refers to aryloxy groups further bearing one or more substituents as set forth above. "Heteroaryloxy" refers to a group —OHt, wherein Ht is a heteroaryl group as defined above, and "substituted heteroaryloxy" refers to heteroaryloxy groups further bearing one or more substituents as set forth above. "Alkoxycarbonyl" refers to a group —C(O)—OR, wherein R is an alkyl group as defined above.

"Acyl" refers to a group —C(O)—R, where R is H, alkyl, substituted alkyl, cycloalkyl, substituted cycloalkyl, alkenyl, substituted alkenyl, aryl, substituted aryl, heteroaryl or substituted heteroaryl, as defined above. "Acyloxy" refers to a group —O—C(O)—R, where R is H, alkyl, substituted alkyl, cycloalkyl, substituted cycloalkyl, alkenyl, substituted alkenyl, aryl, substituted aryl, heteroaryl or substituted heteroaryl, as defined above. "Acylamino" refers to a group —NR'C(O)R, where R and R' are each independently chosen from H, alkyl, substituted alkyl, cycloalkyl, substituted cycloalkyl, alkenyl, substituted alkenyl, aryl, substituted aryl, heteroaryl or substituted heteroaryl, as defined above. "Alkylsulfonyl" refers to a group —S(O)$_2$R, where R represents an alkyl or cycloalkyl group as defined above. "Alkylsulfinyl" refers to a group —S(O)R, where R represents an alkyl or cycloalkyl group as defined above.

Non-limiting examples of aldehydes of the general formula I include the following: trimethylacetaldehyde (compound 1)

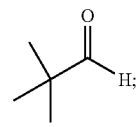

(1)

2,2-dimethyl-4-pentenal (compound 2)

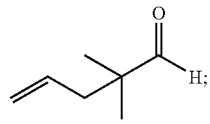

(2)

4-ethyl-4-fonnyl-hexanenitrile (compound 3)

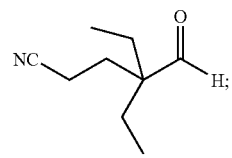

(3)

3-hydroxy-2,2-dimethylpropanal (compound 4)

(4)

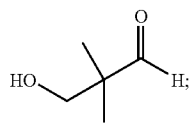

2-formyl-2-methyl-propylmethanoate (compound 5)

(5)

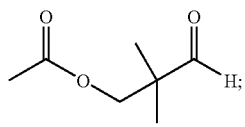

2,2-dimethyl-3-(p-methylphenyl)propanal (compound 6)

(6)

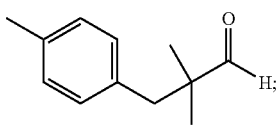

2-methyl-2-phenylpropionaldehyde (compound 7)

(7)

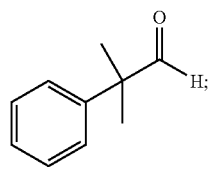

and 2-ethyl-2-methyl-propionaldehyde (compound 8)

(8)

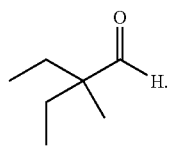

The most common reactions known for the decarbonylation of aldehydes require drastic conditions, such as strong acidic or basic conditions, high temperatures together with ultraviolet light, radical initiators and/or the presence of a metal catalyst (Jerry March, *Advanced Organic Chemistry, Reactions, Mechanisms and Structure*, John Wiley & Sons, 4$^{th}$ Ed., 1992). However, highly branched aldehydes have been observed to decarbonylate at room temperature when irradiated by ultraviolet light (Berman et al., *J. Am. Chem. Soc.*, 85:4010-4013 (1963); Conant et al., *J. Am. Chem. Soc.* 51:1246-1255 (1929)). The loss of carbon monoxide from tertiary aldehydes leads to tertiary radicals, which are more stable than primary or secondary radicals due to resonance stabilization by hyperconjugation. Hyperconjugation includes the stabilization that results from the interaction of electrons in a σ-bond (usually C—H or C—C) with an adjacent empty (or partially filled) p-orbital or π-orbital to give an extended molecular orbital that increases the stability of the system. Thus, decarbonylation is favored in tertiary aldehydes, as compared to primary and secondary aldehydes.

The inventors have found that the tertiary aldehydes disclosed herein advantageously release CO in the presence of certain reactive oxygen species at room temperature, and thus are expected to be capable of targeting and releasing therapeutic CO into inflamed tissues. In addition, many of the tertiary aldehydes disclosed herein do not release CO in water, which is also expected to be useful for purposes of targeting inflamed tissue. Furthermore, tertiary aldehydes such as those disclosed herein are expected to have potentially fewer side effects than primary or secondary aldehydes. This is because tertiary aldehydes, having a higher branching and a less electrophilic carbonyl group, are less reactive towards nucleophiles, and therefore less prone to interact with nucleophilic biomolecules (E. Schauenstein, H. Eserbauer & H. Zollner, *Aldehydes in Biological Systems, Their Natural Occurrence and Biological Activity*, Pion Limited, 1977, Ch. 1-2). Indeed, tertiary aldehydes reportedly are less likely than primary and secondary aldehydes to interfere with DNA or inactivate cytochrome P450 (Adam et al., *Free Radical Biol. Med.*, 26:566-79 (1999); Raner et al., *Biochem.* 36:4895-4902 (1997)).

While not to be bound by any particular theory, the following equation 1 shows a proposed mechanism for the decarbonylation of tertiary aldehydes (exemplified by trimethylacetaldehyde (compound 1)) by reactive oxygen species, generating carbon monoxide and a stabilized tertiary radical:

(1)

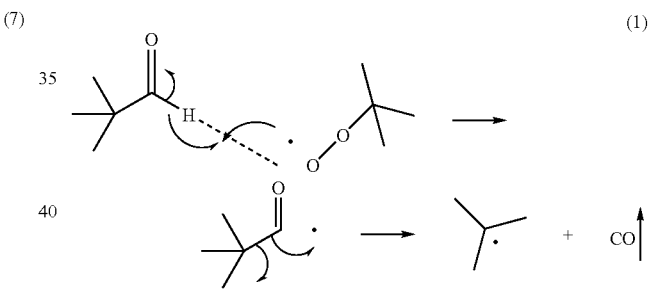

Accordingly, in certain embodiments, the aldehyde is a tertiary aldehyde. In such embodiments, the aldehyde is a compound of the above formula I in which $R_1$, $R_2$ and $R_3$ are each independently selected from alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or two or more of $R_1$, $R_2$ and $R_3$ are taken together to form a substituted or unsubstituted carbocyclic or heterocyclic ring structure.

In some embodiments, the aldehyde is an optionally substituted alkyl or alkenyl tertiary aldehyde. In particular, the aldehyde is a compound of formula I in which $R_1$, $R_2$ and $R_3$ are each independently selected from alkyl, substituted alkyl, cycloalkyl, substituted cycloalkyl, alkenyl, and substituted alkenyl. Non-limiting examples include the above-identified compound 1 (simple alkyl), compound 2 (simple alkenyl), compound 3 (cyano-substituted alkyl), compound 4 (hydroxyl-substituted alkyl), compound 5 (acyloxy-substituted alkyl) and compound 8 (simple alkyl).

In some embodiments, the aldehyde is an alkyl or alkenyl tertiary aldehyde with one aromatic or alkylaromatic substituent. Specifically, the aldehyde is a compound of formula I in which $R_1$ and $R_2$ are each independently selected from alkyl, substituted alkyl, cycloalkyl, substituted cycloalkyl, alkenyl, and substituted alkenyl, and $R_3$ is selected from aryl, substituted aryl, heteroaryl, substituted heteroaryl, alkylaryl, and substituted alkylaryl. Non-limiting examples include the above-identified compound 6 (alkylaryl), and compound 7 (aryl).

In some embodiments, the aldehyde is a trialkyl or triaryl substituted aldehyde. Specifically, the aldehyde is a compound of formula I in which $R_1$, $R_2$ and $R_3$ are alkyl, or in which $R_1$, $R_2$ and $R_3$ are aryl.

In some instances, for example, to improve the in vivo stability, bioavailability, or pharmacokinetic properties of a therapeutic aldehyde, the aldehyde is administered in the form of a derivative, or a protected form thereof. The derivative serves as a source of the free or unmodified aldehyde in vivo and/or releases CO in vivo itself. In certain embodiments, an aldehyde derivative is generated that acts as a prodrug, a pharmacologically inactive chemical entity that, when chemically transformed or metabolised in an animal, is converted into a pharmacologically active substance. The generation of the therapeutically effective molecule (i.e., the aldehyde) from the prodrug occurs prior to, during or after reaching the site of action within the body (Bundgaard et al., *Int. J. Pharm.* 13:89-98 (1983)). Release of the aldehyde from the prodrug generally occurs via chemical or enzymatic lability, or both, within the body system.

Examples of aldehyde prodrugs that are chemically labile include, without limitation, non-cyclic chain compounds that exist in equilibrium in physiological media, such as Mannich base derivatives, imines, oximes, amidines, hydrazones and semicarbazones (WO 2006/012215; Herrmann et al., *Chem. Commun.* 2965-2967 (2006); Deaton et al., *Bioorg. Med. Chem. Lett.* 16:978-983 (2006)), and ring chain tautomeric prodrugs such as 1,3-X,N-heterocycles (X=O, S, NR) (Valters et al., *Adv. Heterocycl. Chem* 64:251-321 (1995); Valters et al., *Adv. Heterocycl. Chem.* 66:1-71 (1996)) that are prepared from the reaction of difunctional compounds with aldehydes. From the ring chain equilibria of these derivatives, the open form undergoes hydrolysis to give the bioactive molecule. In both cases, the ratios of the species involved in the equilibria of these systems are strongly influenced by the steric and electronic characters of the substituents.

An alternative strategy is to generate prodrugs that are converted to the pharmacologically active compound by an enzymatic process (Bernard Testa & Joachim M. Mayer, *Hydrolysis in Drug and Prodrug Metabolism, Chemistry, Biochemistry and Enzymology* WILEY-VCH, 2003). There are several types of chemical groups such as, for example, esters, amides, sulphates and phosphates, that are readily cleaved by esterases, aminases, sulphatases and phosphatases, respectively. Pharmacologically active aldehydes are released by the action of esterases and amidases on a variety of compounds that include acyloxyalkyl esters, N-acyloxyalkyl derivatives, N-Mannich bases derivative, N-hydroxymethyl derivatives, and others. In some instances, to facilitate hydrolysis when the prodrug is a poor substrate for the aldehyde-generating enzyme, the carrier is modified with electron withdrawing or donating groups.

As recognized by those skilled in the art, organic aldehydes undergo a variety of reactions that render the aldehyde chemically protected. By way of non-limiting example, in various embodiments, organic aldehydes are protected by conversion to the corresponding acetal, hemiacetal, aminocarbinol, aminal, imine, enaminone, imidate, amidine, iminium salt, sodium bissulfite adduct, hemimercaptal, dithioacetal, 1,3-dioxepane, 1,3-dioxane, 1,3-dioxalane, 1,3-dioxetane, α-hydroxy-1,3-dioxepane, α-hydroxy-1,3-dioxane, α-hydroxy-1,3-dioxalane, α-keto-1,3-dioxepane, α-keto-1,3-dioxane, α-keto-1,3-dioxalane, ax-keto-1,3-dioxetane, macrocyclic ester/imine, macrocyclic ester/hemiacetal, oxazolidine, tetrahydro-1,3-oxazine, oxazolidinone, tetrahydro-oxazinone, 1,3,4-oxadiazine, thiazolidine, tetrahydro-1,3-thiazine, thiazolidinone, tetrahydro-1,3-thiazinone, imidazolidine, hexahydro-1,3-pyrimidine, imidazolidinone, tetrahydro-1,3-pyrimidinone, oxime, hydrazone, carbazone, thiocarbazone, semicarbazone, semithiocarbazone, acyloxyalkyl ester derivative, O-acyloxyalkyl derivative, N-acyloxyalkyl derivative, N-Mannich base derivative, or N-hydroxymethyl derivative. The exemplary schemes in equations 2-12 below also illustrate how many such prodrugs release the active aldehyde in vivo (e.g., via hydrolytic or enzymatic hydrolysis).

In certain embodiments, the protected organic aldehyde is an imine. Those skilled in the art recognize that such derivatives are obtained in a variety of ways, such as, for example, by the methods described by Deaton et al., *Bioorg. Med. Chem. Lett.* 16: 978-983 (2006), or WO2006/012215, by reaction of an organic aldehyde with an amine as in equation 2:

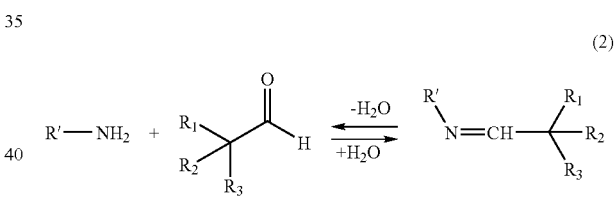

(2)

wherein each of $R_1$, $R_2$ and $R_3$ is independently selected from H, alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or two or more of $R_1$, $R_2$ and $R_3$ are taken together to form a substituted or unsubstituted carbocyclic or heterocyclic ring structure; and R' is selected from H, alkyl, substituted alkyl, cycloalkyl, substituted cycloalkyl, alkenyl, substituted alkenyl, aryl, substituted aryl, heteroaryl and substituted heteroaryl.

In other embodiments, the protected organic aldehyde is an iminium salt. Those skilled in the art recognize that such derivatives can be obtained in a variety of ways, such as, for example, by the methods described by Paukstelis et al., *J. Org. Chem.* 28:3021-3024 (1963), by reaction of an organic aldehyde with a secondary amine salt as in equation 3:

(3)

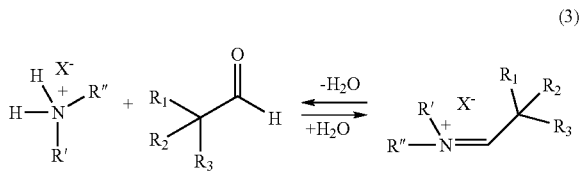

wherein each of $R_1$, $R_2$, $R_3$ and $R'$ is as defined above with respect to equation 2;

$R''$ is selected from H, alkyl, substituted alkyl, cycloalkyl, substituted cycloalkyl, alkenyl, substituted alkenyl, aryl, substituted aryl, heteroaryl and substituted heteroaryl.;

and X represents any suitable and pharmaceutically acceptable counter anion, such as chloride, bromide, phosphate, carbonate, sulfate, acetate or any other non-toxic, physiologically compatible anion.

In another embodiment, the protected organic aldehyde is a hydrazone. Those skilled in the art recognize that such derivatives are prepared in a number of ways such as, for example, by the methods disclosed in U.S. Pat. Nos. 6,518,269 and 4,983,755, by reaction of an organic aldehyde with a hydrazine as in equation 4:

(4)

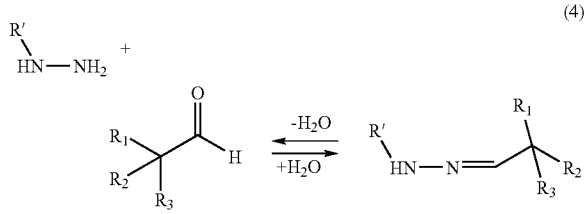

wherein each of $R_1$, $R_2$, $R_3$ and $R'$ is as defined above with respect to equation 2.

In yet another embodiment, the protected organic aldehyde is a carbazone. Those skilled in the art recognize that such derivatives can be obtained in a variety of ways such as, for example, using methods described by Herrmann et al., *Chem. Commun.* 2965-2967 (2006) by reaction of an organic aldehyde with a hydrazide (or acyl hydrazine) as in equation 5:

(5)

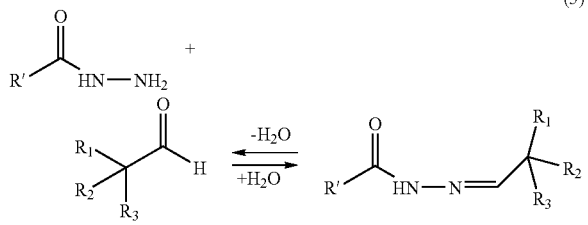

wherein each of $R_1$, $R_2$, $R_3$ and $R'$ is as defined above with respect to equation 2.

In another embodiment, the protected organic aldehyde is a semicarbazone or thiosemicarbazone. Those skilled in the art recognize that such derivatives can be obtained in a variety of ways, such as, for example, using the methods described by Deaton et al., *Bioorg. Med. Chem. Lett.* 16:978-983 (2006) or by the methods disclosed in U.S. Pat. No. 6,458,843, for example, by reaction of an organic aldehyde with a semicarbazine or thiosemicarbazine as in equation 6:

(6)

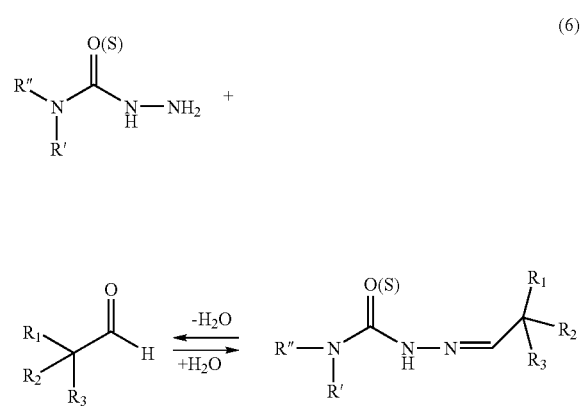

wherein each of $R_1$, $R_2$, $R_3$, $R'$, $R''$ is as defined above with respect to equations 2 and 3.

In still another embodiment, the protected organic aldehyde is an oxime. Those skilled in the art recognize that such derivatives can be obtained in a variety of ways, such as, for example, using the methods described by Reymond et al., *Org. Biomol. Chem.* 2:1471-1475 (2004) or U.S. Patent Application No. 2006/0058513, by reaction of an organic aldehyde with an oxoamine as in equation 7:

(7)

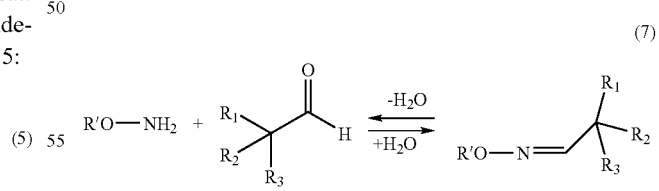

wherein each of $R_1$, $R_2$, $R_3$ and $R'$ is as defined above with respect to equation 2.

In another embodiment, the protected organic aldehyde is an acetal or hemiacetal. Those skilled in the art recognize that such derivatives can be prepared in a variety of ways, such as, for example, by reaction of an aldehyde with one or more alcohols as in equation 8:

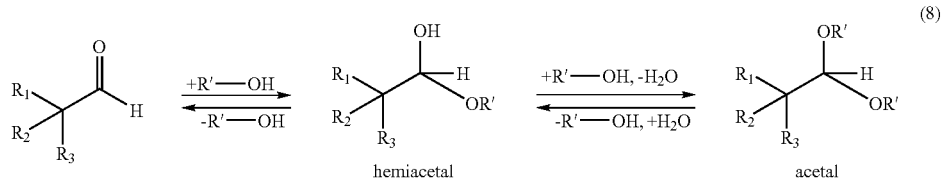

(8)

wherein each of $R_1$, $R_2$, $R_3$ and $R'$ is as defined above with respect to equation 2.

In still another embodiment, the protected organic aldehyde is an α-hydroxy-1,3-dioxepane (or α-hydroxy-1,3-dioxane or α-hydroxy-1,3-dioxalane). Those skilled in the art recognize that such derivatives can be obtained in a variety of ways, such as, for example, by the methods disclosed in WO03/082850, by reaction of a hydroxy substituted organic aldehyde with another aldehyde, as in equation 9:

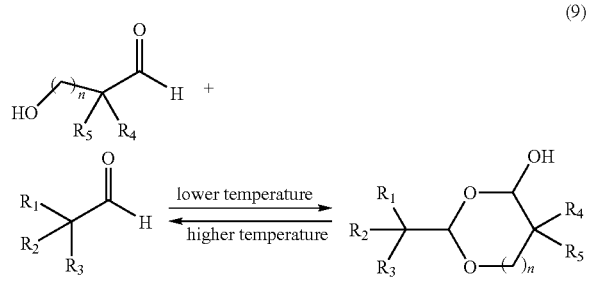

(9)

wherein each of $R_1$, $R_2$ and $R_3$ is as defined above with respect to equation 2;

each of $R_4$ and $R_5$ is independently selected from H, alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or $R_4$ and $R_5$ are taken together to form a substituted or unsubstituted carbocyclic or heterocyclic ring structure; and n is 1, 2 or 3.

The reaction shown in equation 9 is an energetically favorable cyclization (dimerization) that occurs spontaneously when the compounds are cooled together (1:1) to room temperature. When heated (e.g., to physiological temperatures), they separate again. Compound 4 is an example of a compound that forms a dimer upon cooling to room temperature.

In yet another embodiment, the protected organic aldehyde is an α-keto-1,3-dioxepane (or α-keto-1,3-dioxane, α-keto-1,3-dioxalane or α-keto-1,3-dioxetane). Those skilled in the art recognize that such derivatives can be obtained in a variety of ways, such as, for example, by the methods described by Xu et al., *Tet. Lett.*, 46:3815-3818 (2005) or Krall et al., *Tetrahedron* 61:137-143 (2005), by reaction of an organic aldehyde with a hydroxy acid, thereby forming a protected aldehyde, as in equation 10:

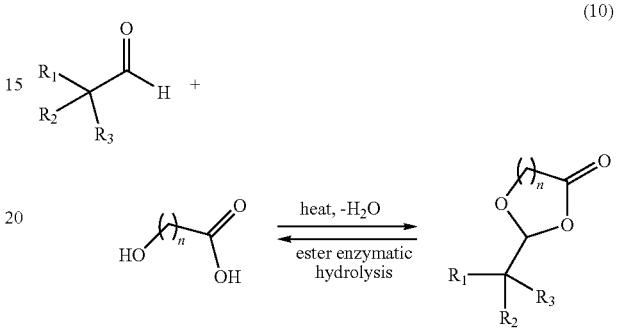

(10)

wherein each of $R_1$, $R_2$ and $R_3$ is as defined above with respect to equation 2; and n is 0, 1, 2, or 3.

In another embodiment, the protected organic aldehyde is a macrocyclic ester/imine. Those skilled in the art recognize that such derivatives can be obtained in a variety of ways, such as, for example, as described in U.S. Pat. No. 6,251,927, by reaction of a hydroxy substituted organic aldehyde with a compound of the formula $HOOC-(CH_2)_m-NH_2$, thereby forming a protected aldehyde, as in equation 11:

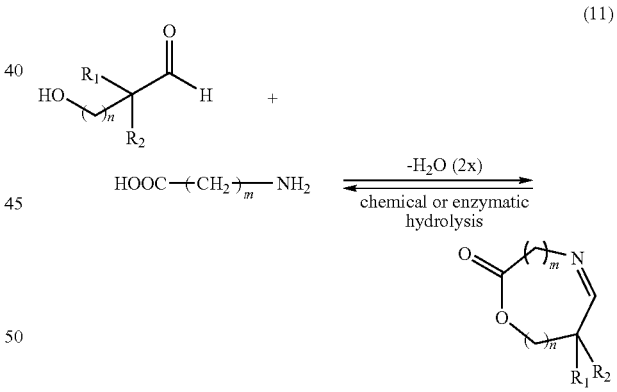

(11)

wherein $R_1$ and $R_2$ are as defined above with respect to equation 2; n is 0, 1, or 2; and m is 1 or 2.

Hydrolysis of the compound formed in equation 11 occurs by chemical hydrolysis through the imine, or enzymatic hydrolysis through the ester group.

In another embodiment, the protected organic aldehyde is a macrocyclic ester/hemiacetal. Those skilled in the art recognize that such derivatives can be obtained in a variety of ways, such as, for example, as described in U.S. Pat. No. 6,251,927 by reaction of a hydroxy substituted organic aldehyde with a hydroxy acid having the structure $HOOC-(CH_2)_m-OH$, thereby forming a protected aldehyde, as in equation 12:

(12)

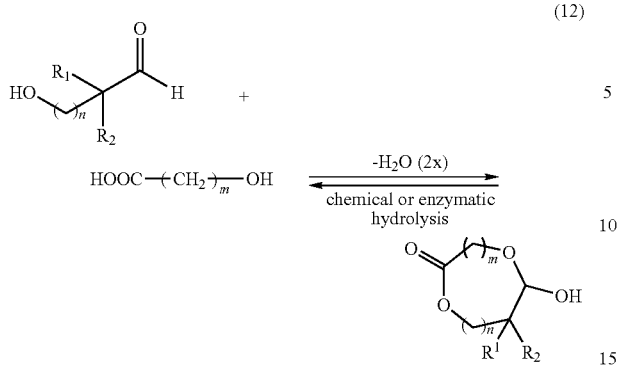

wherein $R_1$, $R_2$, m and n are as defined above with respect to equation 11.

Hydrolysis of the compound formed in equation 12 occurs by chemical hydrolysis through the ketal, or enzymatic hydrolysis through the ester group.

In still another embodiment, the protected organic aldehyde is a thiazolidine or a tetrahydro-1,3-thiazine. Those skilled in the art recognize that such derivatives can be obtained in a variety of ways, such as, for example, by employing the methods described by Jellum et al., *Anal. Biochem.* 31:339-347 (1969), Nagasawa et al., *J. Biochem. Mol. Tox.* 16:235-244 (2002), Roberts et al., *Chem. Res. Toxicol.* 11: 1274-82 (1998) or U.S. Pat. No. 5,385,922. Certain thiazolidines and tetrahydro-1,3-thiazines contemplated for use as described herein are represented by formula II:

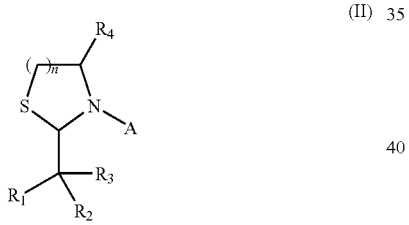

(II)

wherein each of $R_1$, $R_2$, $R_3$ and $R_4$ is independently selected from H, alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$, and cyano; or two or more of $R_1$, $R_2$ and $R_3$ are taken together to form a substituted or unsubstituted carbocyclic or heterocyclic ring structure;

A is selected from H, alkyl, substituted alkyl, cycloalkyl, substituted cycloalkyl, alkenyl, substituted alkenyl, aryl, substituted aryl, heteroaryl, substituted heteroaryl, alkylaryl, substituted alkylaryl, alkoxycarbonyl, acyl, acyloxy, acylamino, alkylsulfonyl and alkylsulfinyl; and n is 1 or 2.

In another embodiment, the protected organic aldehyde is an oxazolidine or a tetrahydro-1,3-oxazine. Those skilled in the art recognize that such derivatives can be obtained in a variety of ways, such as, for example, by employing the methods described by Bundgaard et al., *Int. J. Pharma. Chem.* 10:165-175 (1982), Selambarom et al., *Tetrahedron* 58:9559-9556 (2002) or U.S. Pat. No.7,018,978. Certain oxazolidines and tetrahydro-1,3-oxazines contemplated for use as described herein are represented by formula III:

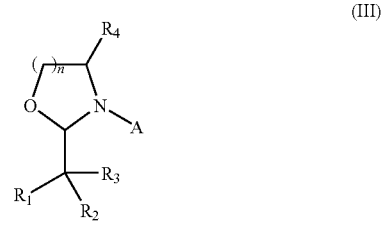

(III)

wherein each of $R_1$, $R_2$, $R_3$, $R_4$ and A and n is as described above with respect to formula II.

In still another embodiment, the protected organic aldehyde is an imidazolidine or a 1,3-hexahydro-pyrimidine. Those skilled in the art recognize that such derivatives can be obtained in a variety of ways, such as, for example, by employing the methods described by Lambert, *J. Org. Chem.* 52:68-71 (1987) or Fülöp, *J. Org. Chem.* 67:4734-4741 (2002). Certain imidazolidines and 1,3-hexahydro-pyrimidines contemplated for use as described herein are represented by formula IV:

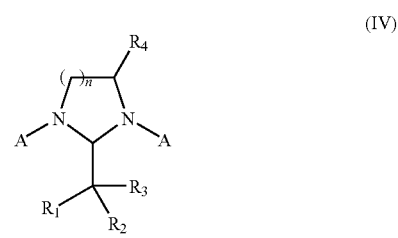

(IV)

wherein each of $R_1$, $R_2$, $R_3$, $R_4$, n and A (selected independently at each occurrence) is as described above with respect to formula II.

In yet another embodiment, the protected organic aldehyde is an imidazolidinone. Those skilled in the art recognize that such derivatives can be obtained in a variety of ways, such as, for example, by employing the methods described by Bundgaard et al., *Int. J. Pharma. Chem.* 23:163-173 (1985). Certain imidazolidinones contemplated for use as described herein are represented by formula V:

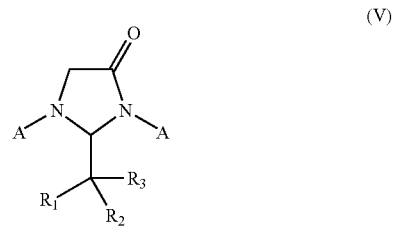

(V)

wherein each of $R_1$, $R_2$, $R_3$ and A (selected independently at each occurrence) is as described above with respect to formula II.

In another embodiment, the protected organic aldehyde is an acyloxyalkyl ester or O-acyloxyalkyl derivative. Those skilled in the art recognize that such derivatives can be obtained in a variety of ways, such as, for example, by employing the methods described by Nudelman et al., *Eur J. Med. J. Chem.* 36: 63-74 (2001), Nudelman et al., *J. Med. Chem.* 48:1042-1054 (2005), or Swedish Patent No. SE9301115. Certain acyloxyalkyl esters contemplated for use as described herein are represented by formula VI:

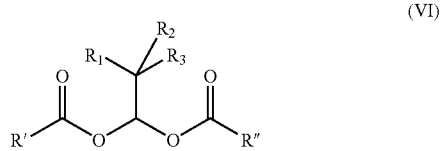

(VI)

wherein each of $R_1$, $R_2$, and $R_3$ is as defined above with respect to formula II, and each of R' and R" is selected independently from H, alkyl, substituted alkyl, cycloalkyl, substituted cycloalkyl, alkenyl, substituted alkenyl, aryl, substituted aryl, heteroaryl, and substituted heteroaryl. In certain embodiments, in addition to releasing the active aldehyde upon metabolic hydrolysis in vivo, an acyloxyalkyl ester derivative also releases butyric acid. Butyric acid prodrugs have been reported to provide increased aqueous solubility and permeability across cell membranes (Nudelman et al., *Eur J. Med. J. Chem.* 36: 63-74 (2001)).

In another embodiment, the protected organic aldehyde is an N-acyloxyalkyl derivative. Those skilled in the art recognize that such derivatives can be obtained in a variety of ways, such as, for example, by employing the methods described by Bundgaard et al., *Int. J. Pharm.* 22:454-456 (1984) and Bundgaard et al., *Int. J. Pharm.* 13:89-98 (1983). Certain N-acyloxyalkyl derivatives contemplated for use as described herein are represented by formula VII:

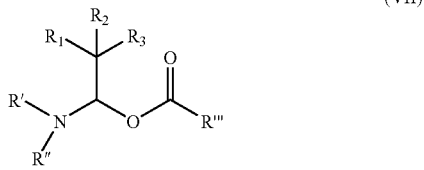

(VII)

wherein each of $R_1$, $R_2$, $R_3$, R' and R" is as described above with respect to formulas II and VI;

and R'" is selected from H, alkyl, substituted alkyl, cycloalkyl, substituted cycloalkyl, alkenyl, substituted alkenyl, aryl, substituted aryl, heteroaryl, and substituted heteroaryl.

In another embodiment, the protected organic aldehyde is the salt of an N-acyloxyalkyl derivative. Those skilled in the art recognize that such derivatives can be obtained in a variety of ways, such as, for example, by employing the methods described by Bodor et al., *J. Med. Chem.* 23:469-474 (1980) or U.S. Pat. No. 3,998,815. The salts of N-acyloxyalkyl derivatives contemplated for use as described herein are represented by formula VIII:

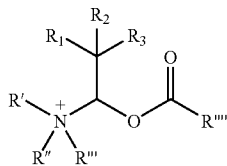

(VIII)

wherein each of $R_1$, $R_2$, $R_3$, R', R", and R'" is as defined above with respect to formula VII;

R"" is selected from H, alkyl, substituted alkyl, cycloalkyl, substituted cycloalkyl, alkenyl, substituted alkenyl, aryl, substituted aryl, heteroaryl, and substituted heteroaryl; and X represents a suitable and pharmaceutically acceptable counter anion, as described above with respect to equation 3.

In yet another embodiment, the protected organic aldehyde is a 5-oxazolidinone. Those skilled in the art recognize that such derivatives can be obtained in a variety of ways, such as, for example, by employing the methods described by Bundgaard et al., *Int. J. Pharma. Chem.* 46:159-167 (1988) or Ishai-Ben, *J. Am. Chem. Soc.* 79:5736-38 (1957). Certain 5-oxazolidinones contemplated for use as described herein are represented by formula IX:

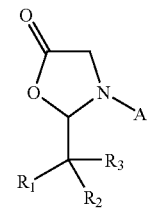

(IX)

wherein each of $R_1$, $R_2$, $R_3$ and A is as defined above with respect to formula II.

The organic aldehydes and their derivatives disclosed herein are administered to treat inflammatory disease in animals, such as mammals, including but not limited to human patients. "Inflammatory disease" as used herein refers to a disease or condition characterized by inflammation. Inflammation encompasses the first response of the immune system to infection or irritation, and is sometimes referred to as the innate cascade. Inflammation typically is characterized by one or more of the following symptoms: redness, heat, swelling, pain, and dysfunction of the organs involved. "Treatment" as used herein encompasses prevention of a disease or its progression, reduction of one or more symptoms (e.g., pain) associated with a disease or condition, and/or amelioration or curing of the underlying disease state or condition. An "anti-inflammatory effective amount" of an aldehyde or its derivative is an amount sufficient for treatment of an inflammatory disease.

Examples of inflammatory diseases treatable as described herein include without limitation transplant rejection; chronic inflammatory disorders of the joints, such as arthritis, rheumatoid arthritis, juvenile idiopathic arthritis, ankylosing spondylitis, psoriatic arthritis, osteoarthritis and bone diseases associated with increased bone resorption; inflammatory bowel diseases, such as ileitis, ulcerative colitis, Barrett's syndrome, and Crohn's disease; inflammatory lung disorders, such as asthma, adult respiratory distress syndrome (ARDS), chronic obstructive pulmonary disease (COPD) or chronic obstructive airway disease; inflammatory disorders of the eye, such as corneal dystrophy, trachoma, onchocerciasis, uveitis, sympathetic ophthalmitis and endophthalmitis; chronic inflammatory disorders of the gum, such as gingivitis and periodontitis; tuberculosis; leprosy; inflammatory diseases of the kidney, such as uremic complications, glomerulonephritis and nephrosis; inflammatory diseases of the liver, such as viral hepatitis and autoimmune hepatitis; inflammatory disorders of the skin, such as sclerodermatitis, psoriasis, erythema, eczema, or contact dermatitis; inflammatory diseases of the central nervous system, such as stroke, chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, such as diabetes mellitus, immune-complex vasculitis, systemic lupus erythematosus (SLE); inflammatory diseases of the heart, such as cardiomyopathy, ischemic heart disease, hypercholesterolemia, and atherosclerosis; as well as inflammation resulting from various diseases such as preeclampsia, chronic liver failure, brain and spinal cord trauma, and cancer. Inflammatory diseases treatable as described herein further include systemic inflammations of the body. Examples of systemic inflammation include but are not limited to gram-positive or gram negative shock, sepsis, septic shock, hemorrhagic or anaphylactic shock, and systemic inflammatory response syndrome. Further examples of inflammatory disease include circulatory shock, hemorrhagic shock and cardiogenic shock.

In one embodiment, the inflammatory disease is a chronic inflammatory disease, such as rheumatoid arthritis. In another embodiment, the inflammatory disease is a disease associated with a chronic inflammatory reaction, such as atherosclerosis or Alzheimer's disease; or with ischemia/reperfusion injury, such as myocardial infarction, stroke, sleep apnea or transplantation. In one embodiment, the inflammatory disease is an infectious disease, such as septic shock.

The organic aldehydes and their derivatives disclosed herein are formulated into pharmaceutical compositions for administration to treat inflammatory disease. In certain embodiments, the compositions include a pharmaceutically acceptable salt of the aldehyde or derivative, for example, a pharmaceutically acceptable salt of a compound having the general formula I above. Those skilled in the art understand the use of pharmaceutically acceptable salt forms of compounds in formulating pharmaceutical compositions. The compositions are administered in a variety of forms, adapted to the chosen route of administration. Suitable routes of administration include without limitation oral, rectal, transdermal, topical, and parenteral, e.g., intravenous (i.v.), subcutaneous, intramuscular, intrapleural, intraperitoneal, intrafocal and perifocal administration.

The pharmaceutical compositions typically contain an organic aldehyde or its derivative as disclosed herein, or a pharmaceutically acceptable salt thereof, as an active agent in a non-toxic, pharmaceutically acceptable vehicle. In certain embodiments, the composition is an admixture of the active agent and a carrier in solid, semisolid, or liquid form. In some embodiments, the active agent is provided in an encasing composition, for example, a capsule, a tablet coating, a bag, or some other container for the active agent. In certain embodiments, the vehicle includes one or more additional formulating agents, flavoring agents, coloring agents, or preservatives.

Suitable compositions for oral administration include, for example, tablets, dragees, capsules, pills, powders, troches, granules, suspensions, emulsions, solutions, syrups and elixirs. In certain embodiments, the pharmaceutical composition is a solid dosage form including a carrier that contains at least one inert diluent, such as, for example, sucrose, lactose or starch. In some instances, such carriers also include one or more additional formulating substances, e.g., lubricating agents such as magnesium stearate. In some embodiments, capsules, tablets, troches or pills are prepared with a carrier that also includes one or more buffering agents. In certain embodiments, vehicles such as tablets, pills, or granules are prepared with enteric coatings.

In certain embodiments, tablets are prepared including the active agent and one or more of the following: an inert diluent, such as, for example, calcium carbonate, calcium phosphate, sodium phosphate, or lactose; a granulation or distributing agent, such as corn starch or alginate; a binder, such as amylose, gelatin, or acacia gum; and a lubricant, such as aluminum stearate, magnesium stearate, talc, or silicone oil. In some embodiments, tablets are provided with a coating that effects a delayed dissolution and reabsorption of the active agent in the gastrointestinal tract and thus, for example, provides improved compatibility or a longer duration of effectiveness. In certain embodiments, gelatin capsules are prepared containing the active agent in a mixture with a solid diluent (e.g., calcium carbonate or kaolin), or an oily diluent (e.g., olive, peanut, or paraffin oil).

In certain embodiments, liquid dosage forms are prepared with inert diluents commonly used in the art, such as water. In some instances such compositions further include one or more additional components including adjuvants, such as dispersing and wetting agents, emulsifying and suspending agents, sweetening and flavoring agents, and/or preservatives. Suitable suspension agents include, for example, sodium carboxymethylcellulose, methylcellulose, hydroxypropylcellulose, sodium alginate, polyvinylpyrrolidone, tragacanth gum and acacia gum. Non-limiting examples of suitable dispersing and wetting agents include polyoxyethylene stearate, heptadecaethyleneoxycetanol, polyoxyethylene, sorbitol monooleate, polyoxyethylene sorbitan monooleate or lecithin. Suitable preservatives include, for example, methyl or propyl hydroxybenzoate. Non-limiting examples of suitable flavoring agents and sweeteners include sucrose, lactose, dextrose or sugar syrup.

In some embodiments, oily suspensions are prepared including, for example, peanut, olive, sesame, coconut, or paraffin oil, and optionally one or more thickeners, such as beeswax, hard paraffin or cetyl alcohol, sweeteners, flavoring agents and/or anti-oxidants. In certain embodiments, emulsions are prepared including, for example, olive, peanut, or paraffin oil in addition to one or more emulsifiers, such as acacia gum, tragacanth gum, phosphatides, sorbitan monooleate or polyoxyethylene sorbitan monooleate, and optionally one or more sweeteners and/or flavoring agents. In other embodiments, water dispersible powders or granules are prepared containing the active agent in a mixture with one or more dispersing, wetting, or suspension agents, e.g., the aforementioned materials and/or dimethyl sulfoxide, as well as optionally one or more sweeteners, flavoring agents and/or coloring agents.

In certain embodiments, the organic aldehydes are administered parenterally as sterile isotonic sodium chloride solutions or other solutions. In some instances, to promote uniform dissolution or suspension, a solubilizer is added, such as dimethyl sulfoxide. Pharmaceutically acceptable carriers for intravenous administration include, without limitation, solutions containing pharmaceutically acceptable salts or sugars. Pharmaceutically acceptable carriers for intramuscular or subcutaneous injection include, without limitation, salts, oils, or sugars. In some instances, carriers such as solvents, water, buffers, alkanols, cyclodextrins and aralkanols are used. Other optional auxiliary, non-toxic ingredients include, for example, polyethylene glycols or wetting agents. In certain embodiments, an injectable solution is formulated with a buffer such as, for example, sodium bicarbonate or tris(hydroxymethyl)aminomethane. In at least some instances, the formulation has a pH between about 4 and about 7, for example, between about 5.0 and about 5.5.

Pharmaceutically acceptable carriers for preparing compositions for topical administration include, without limitation, dimethyl sulfoxide, alcohol, and propylene glycol. In some instances, topical compositions are applied using patches or other liquid retaining material to hold the pharmaceutical composition in contact with the skin.

Suitable compositions for rectal administration include, without limitation, suppositories produced with one or more binders that melt at rectal temperature, for example, cocoa butter or polyethylene glycols.

In some embodiments, the organic aldehyde composition is formulated to provide sustained release or delayed release. In certain embodiments, carriers based on nanoparticles or nanoencapsulates are used, e.g., to protect the active agent and provide for its slow release in the organism or specific tissues.

In certain embodiments, the organic aldehydes and their derivatives disclosed herein are administered concomitantly with another active agent, such as another anti-inflammatory or immunosuppressive drug, including but not limited to aspirin and other nonsteroidal anti-inflammatory drugs (NSAIDs), steroids or methotrexate and other disease modifying anti-rheumatic drugs (DMARDs). In various embodiments, the multiple active agents are administered as part of a single dosage form, or in multiple dosage forms administered at the same time or at different times.

In some instances, the organic aldehyde is linked to a second therapeutic agent such as, for instance, an anti-inflammatory agent. In certain embodiments, the second agent is selected based on its known capacity to target the site/tissue in which a therapeutic effect is desired. For example, in some embodiments, an anti-inflammatory agent is selected for its known capacity to accumulate in an inflammatory lesion. Anti-inflammatory drugs that accumulate in inflamed tissues include, without limitation, aspirin, indomethacin, and other nonsteroidal anti-inflammatory drugs that are organic acids. In other embodiments, the organic aldehyde is targeted to a particular tissue or cell type by linking it to a protein carrier. Carrier proteins include but are not limited to antibodies specific for a cell surface protein or a component of the extracellular matrix. In certain embodiments, the aldehyde is linked to an amino acid such as, for example, cysteine. In still other embodiments, an aldehyde is derivatized to target the bones by introducing a phosphonic acid moiety.

Equation 13 illustrates a reaction scheme for introduction of a phosphonic acid moiety to 3-hydroxy-2,2-dimethylpropanal (compound 4). In the illustrated embodiment, the phosphonic acid is introduced using POCl$_3$/Et$_3$N followed by basic hydrolysis.

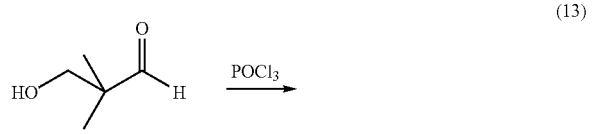

(13)

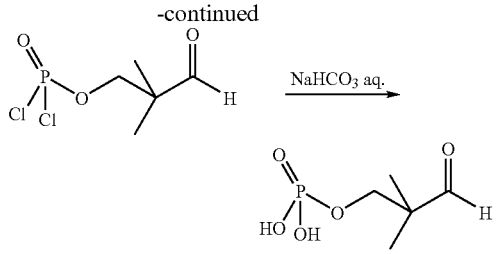

Equation 14 illustrates a reaction scheme for introduction of an amino acid, through the acid function, to 3-hydroxy-2,2-dimethylpropanal (compound 4). In the illustrated embodiment, the N-protected amino acid (e.g., N-Boc-glycine) with DCC (dicyclohexylcarbodiimide) activation reacts with the hydroxyl function.

(14)

The active agent content in the pharmaceutical compositions is ordinarily about 0.01% to about 95% by weight, for example, about 0.1% to about 85% by weight, about 1% to about 70% by weight, or about 5% to about 50% by weight, based on the final pharmaceutical formulation. In various embodiments, the desired daily dose is administered in a single dose, or as divided doses at appropriate intervals, for example, as two, three, four or more sub-doses per day. The sub-dose itself may be divided further into a number of discrete loosely spaced administrations. When administered in a unit dosage form, the pharmaceutical compositions typically contain between about 1 mg and about 10,000 mg, for example, between about 5 mg and about 7,500 mg, between about 10 mg and about 2,000 mg, between about 20 mg and about 1,000 mg, between about 20 mg and about 500 mg, or between about 20 mg and about 300 mg of active agent. In certain embodiments, an aldehyde or its derivative is administered in a daily dose ranging between about 1 mg and about 20,000 mg, for example, between about 5 mg and about 10,000 mg, between about 10 mg and about 5,000 mg, between about 20 mg and about 1,000 mg, between about 40 mg and about 500 mg, or between about 40 mg and about 300 mg of active agent.

The dosage level of active agent in the composition is chosen to provide an amount of active agent that affords the desired therapeutic effect in accordance with the desired method of administration. As those skilled in the art appreciate, the amount of the composition required for use in treatment varies not only with the particular compound selected, but also with the route of administration, the nature of the condition being treated, and the age and condition of the patient, and will be ultimately at the discretion of the attendant physician.

In certain embodiments, useful dosages of organic aldehyde compositions are determined by assessing their in vitro activity and in vivo activity in animal models. Methods for extrapolation of effective dosages in mice and other animals to humans are known to those skilled in the art. (See, e.g., U.S. Pat. No. 4,938,949 and National Institute of Environmental Health Sciences, U.S. Public Health Service, Guidance Document on Using In Vitro Data to Estimate In Vivo Starting Doses for Acute Toxicity.)

The therapeutic aldehydes disclosed herein generate CO after administration to the body. Although in at least some instances CO is generated preferentially at sites of inflammation, some of the CO generated will bind to hemoglobin in red blood cells. Thus, dose-finding studies can be guided by measurement of carboxyhemoglobin (COHb) levels in the blood. Methods for the measurement of COHb levels in the blood are known in the art. In normal healthy humans, COHb levels are about 0.5% in healthy nonsmokers and up to 9% in smokers. In one embodiment, the dose level of the compositions described herein is such that no significant rise in COHb levels is observed. However, in some applications, a transient rise in COHb levels up to about 10% may be tolerated. This level of COHb is not associated with any symptoms.

EXAMPLES

The following examples are illustrative only, and are not intended to be limiting. The following definitions are used herein. "RPMI" is an aqueous tissue culture medium developed by Moore et. al at Roswell Park Memorial Institute (commercially available from Sigma). The abbreviation rpmi is used for RPMI-1630 media supplemented with 10% fetal calf serum. "TBHP" refers to tert-butyl hydroperoxide, T-HYDRO® solution, 70% wt in water. "$H_2O_2$," refers to hydrogen peroxide solution, 35% in water. "pH 2" refers to an aqueous solution with pH between 2 and 2.5. "Eq." refers to the number of equivalents of carbon monoxide.

Example 1

CO Release from Trimethylacetaldehyde (Compound 1) in Different Media

A sample of commercially available (e.g., from Aldrich) trimethylacetaldehyde (compound 1) was placed in a 7.5 ml vial and then sealed with an appropriate stopper. In each experiment 2 ml of the appropriate solution, TBHP, $H_2O_2$, rpmi or pH 2 solution, was added and the vial placed at 37° C. with orbital stirring.

At the appropriate time, 250 μl of the gas mixture was removed from the vial, injected in the gas chromatograph (Trace GC with a TCD detector from Thermo Finnigan, connected to a Chrom-card 32 bit software), and the amount of CO was measured according to previously calibrated conditions.

As shown in FIG. 1, trimethylacetaldehyde released CO in TBHP solution, and very little in acidic aqueous solution. In both cases, the CO release was inhibited by the addition of a radical trap, 2,6-di-tert-butylphenol, thus confirming a radical decarbonylation mechanism. FIG. 1A shows CO release from trimethylacetaldehyde at a concentration of 0.11M. No CO was detected in the rpmi or hydrogen peroxide solutions.

Figure 1B:
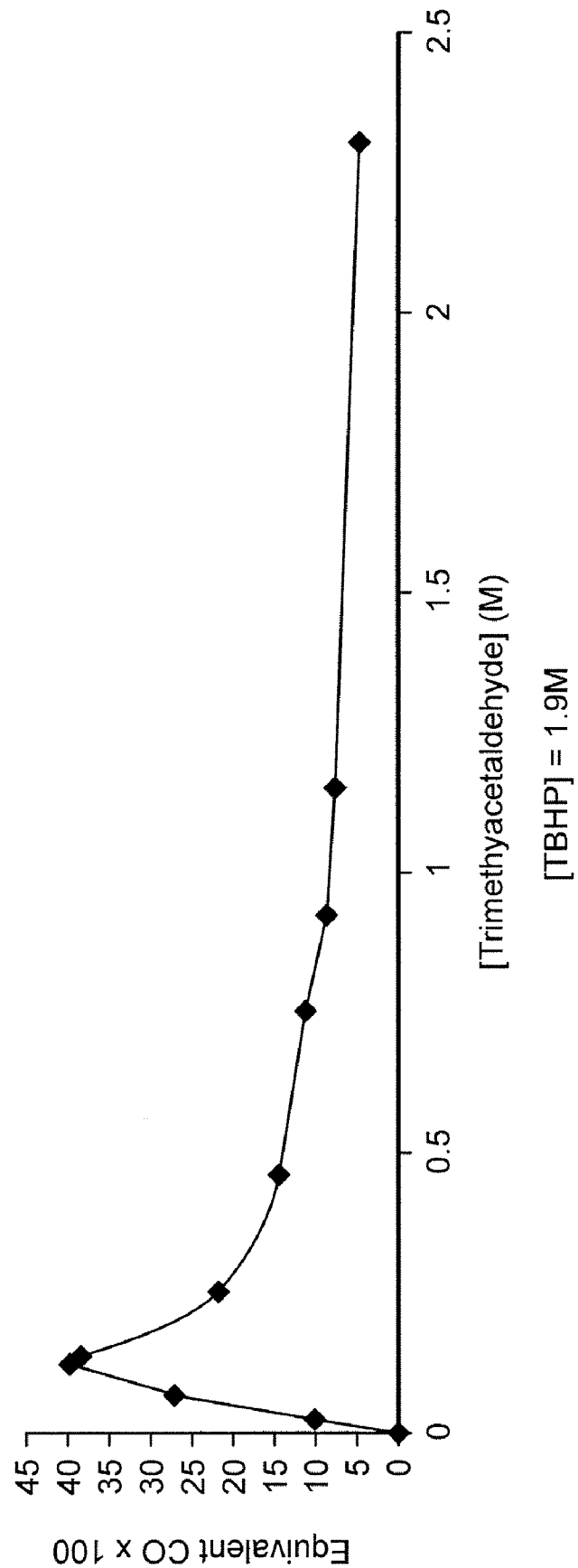
Figure 1C:
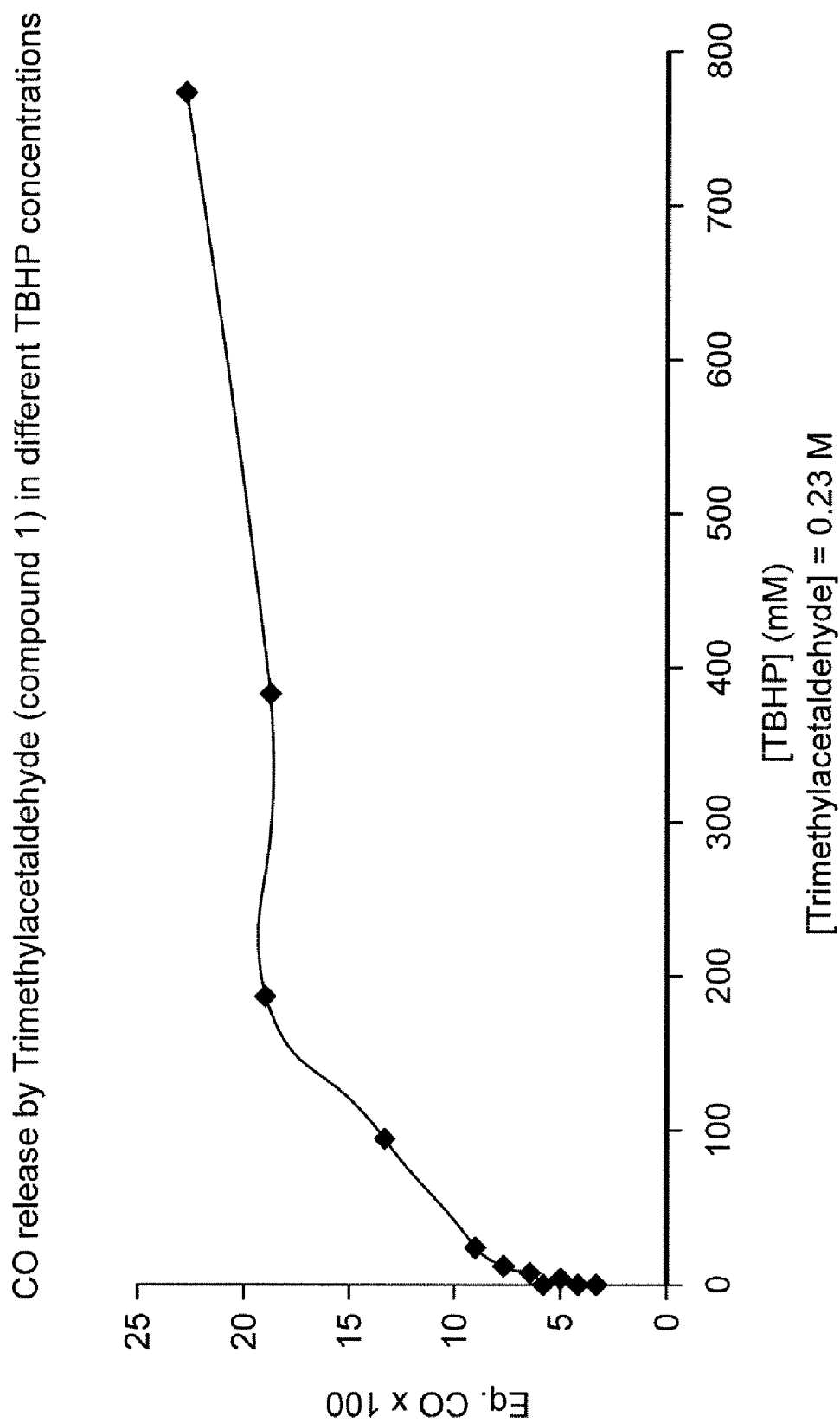
Figure 1D:
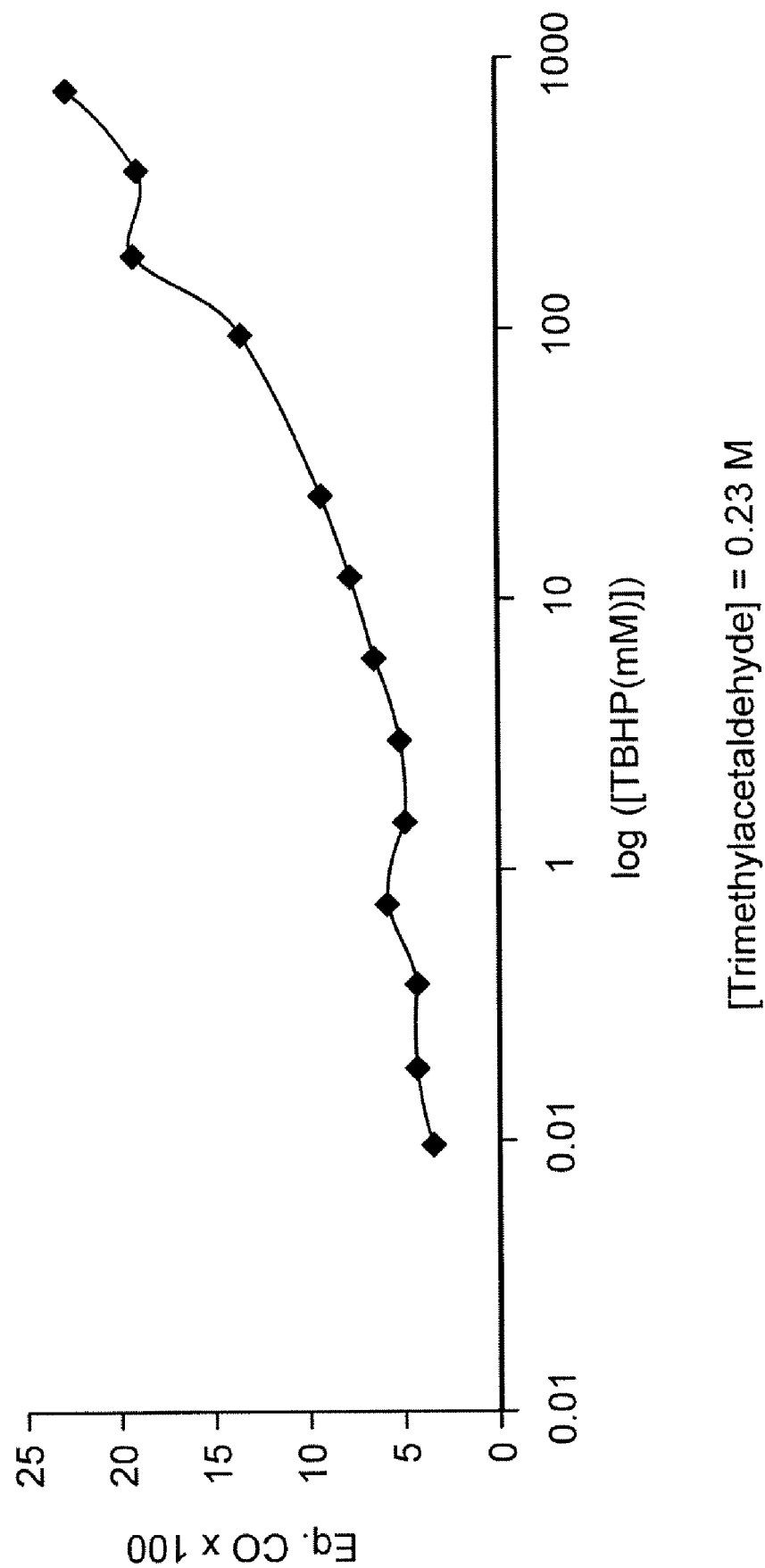

The amount of CO released in TBHP solution varied with the concentration of both trimethylacetaldehyde and TBHP. The CO released by trimethylacetaldehyde increased with the concentration of TBHP until approximately eight equivalents of TBHP was reached. For concentrations up to 32 eq. of TBHP the CO release was maintained. When the concentration of TBHP was reduced to values known to exist in inflamed tissues, such as 1 mM, CO release still was observed. There was also a pronounced effect related to the concentration of trimethylacetaldehyde: the maximum CO release was obtained for concentrations around 0.12M, and CO release decreased approximately to half at higher and lower concentrations of 0.25 M and 0.08 M, respectively. FIG. 1B shows CO release at varying trimethylacetaldehyde concentrations in 1.9 M TBHP. FIGS. 1C-D show CO release from trimethylacetaldehyde at a concentration of 0.23 M in varying concentrations of TBHP.

Example 2

CO Release from 2,2-dimethyl-4-pentenal (Compound 2) in Different Media

A sample of the commercially available (e.g., from Aldrich) 2,2-dimethyl-4-pentenal (compound 2), was placed in a 7.5 ml vial and sealed with an appropriate stopper, and the experiments were performed as described above in Example 1.

Figure 2:
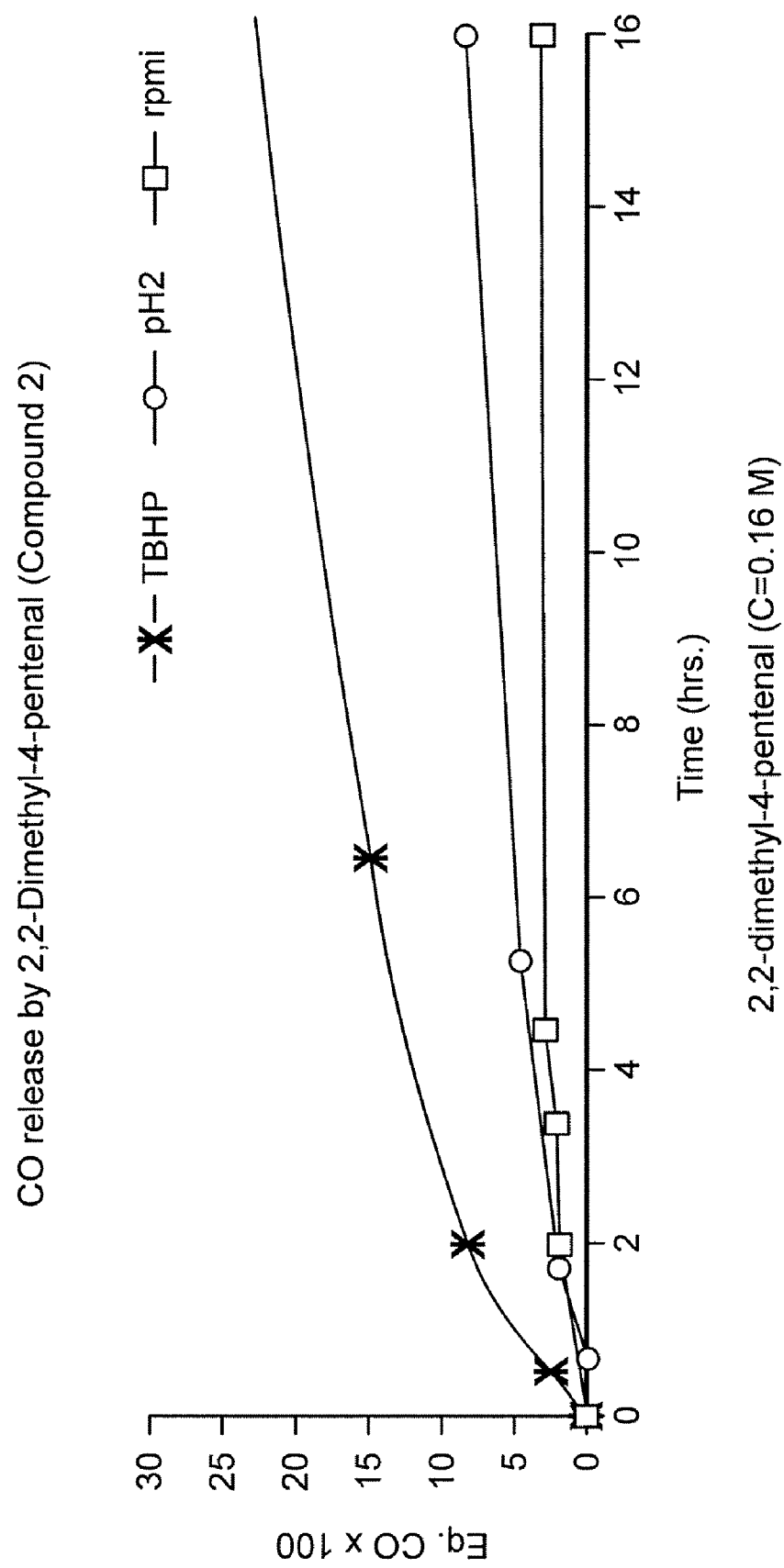
FIG. 2 is a plot showing the kinetics of CO release of 2,2-dimethyl-4-pentenal (compound 2) in TBHP, pH 2 and rpmi solutions.

As shown in FIG. 2, 2,2-dimethyl-4-pentenal (0.16 M) released CO in the TBHP solution, very little at pH 2, and even less in rpmi. No CO release was observed in $H_2O_2$ solution.

Example 3

CO Release From 4-ethyl-4-formyl-hexanenitrile (Compound 3) in Different Media

A sample of the commercially available (from Acros Organic) 4-ethyl-4-formyl-hexanenitrile (compound 3), was placed in a 7.5 ml vial and sealed with an appropriate stopper, and the experiments were performed as described above in Example 1.

Figure 3:
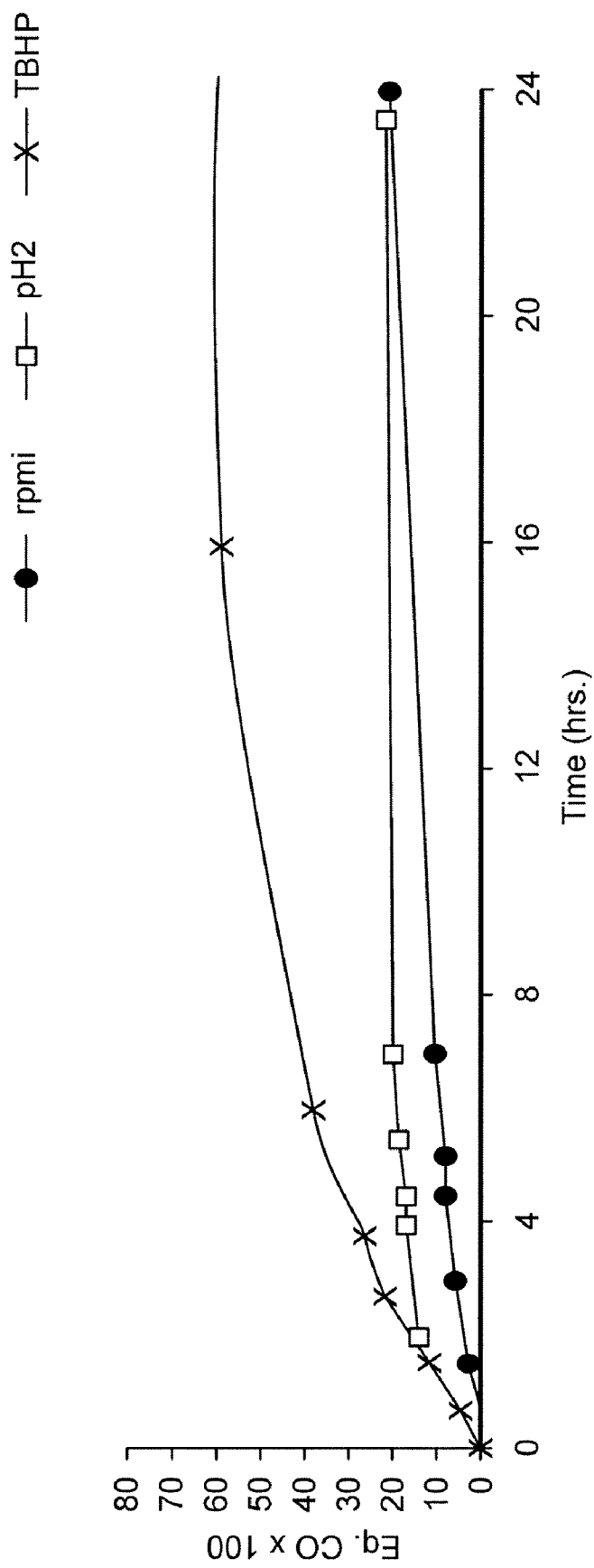
FIG. 3 is a plot showing the kinetics of CO release of 4-ethyl-4-formyl-hexanenitrile (compound 3) in TBHP, pH 2 and rpmi solutions.

As shown in FIG. 3, 4-ethyl-4-formyl-hexanenitrile (0.15 mM) released a very high amount of CO in TBHP, less at pH 2, and even less in rpmi. No CO release was observed in $H_2O_2$ solution.

Example 4

Preparation of 3-hydroxy-2,2-dimethylpropanal (Compound 4) and CO Release From 3-hydroxy-2,2-dimethylpropanal in Different Media The preparation of 3-hydroxy-2,2-dimethylpropanal (compound 4) was performed according to the methods described by Santoro et al., *J. Chem. Soc. Perkin Trans. I* 189-192 (1978).

To a mixture of 2-methylpropionaldehyde (690 mmol) and formaldehyde (37 wt % solution in water) (747 mmol, 1.1 eq.) at 0° C. was added potassium carbonate (290 mmol, 0.42 eq.) portionwise in order to keep the temperature below 20° C. After stirring for 2 hours at room temperature, the reaction mixture was extracted with diethyl ether, dried ($Na_2SO_4$) and evaporated under reduced pressure. The residue was distilled to afford 3-hydroxy-2,2-dimethylpropionaldehyde, b.p. 65° C. (15 mmHg). On cooling to room temperature, the corresponding dimer was formed as a white solid in 52% yield. IR ν (cm$^{-1}$) 3434, 3316, 3222, 3297, 2886, 1475, 1363, 1234, 1118, 1051, 977, 892, 790, 701. Elemental analysis Exp (Calc) C: 58.33 (58.82), H: 10.33 (9.80).

A sample of 3-hydroxy-2,2-dimethylpropanal (compound 4), was placed in a 7.5 ml vial and sealed with an appropriate stopper, and the experiments were performed as described above in Example 1.

Figure 4:
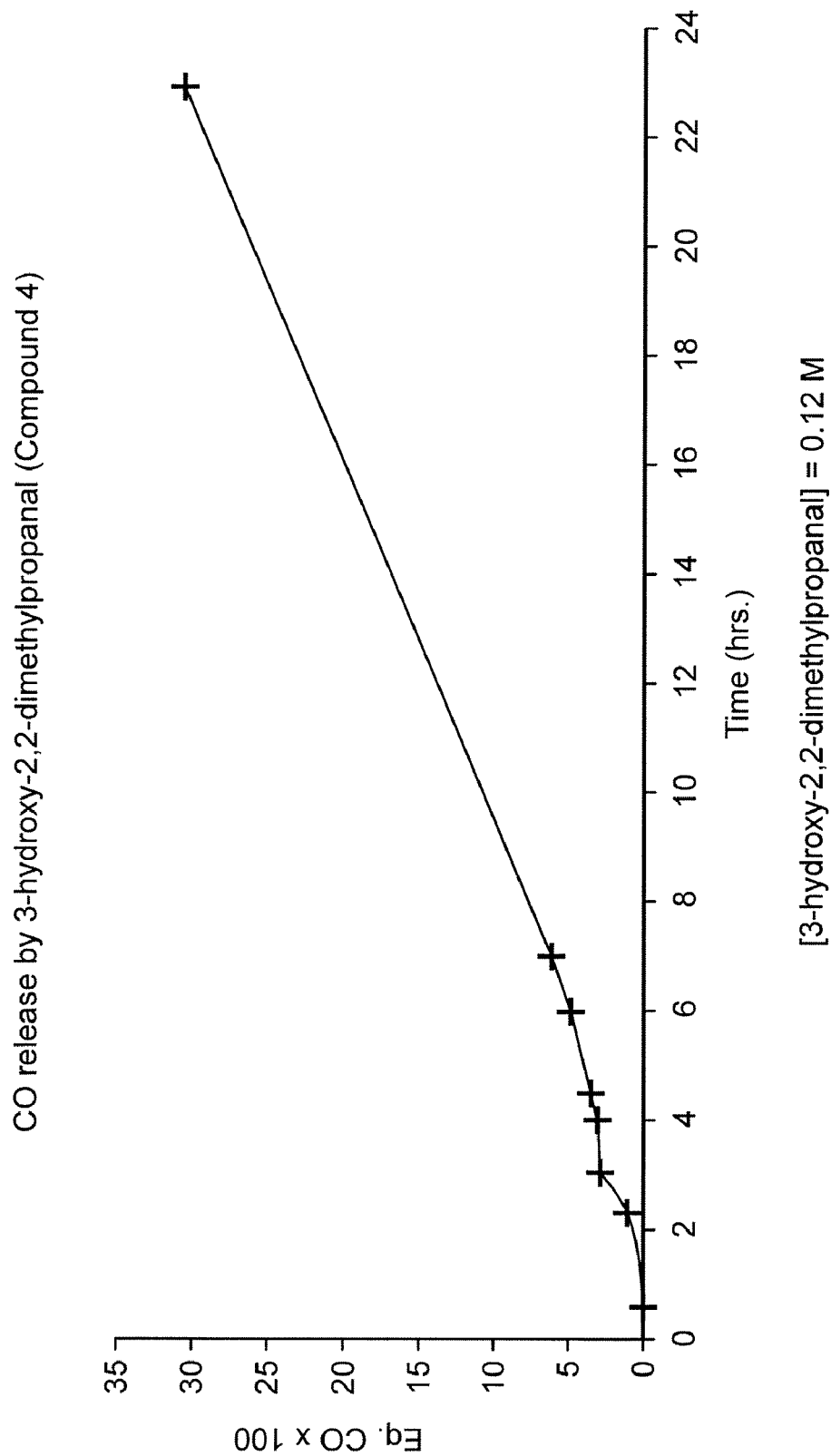
FIG. 4 is a plot showing the kinetics of CO release of 3-hydroxy-2,2-dimethylpropanal (compound 4) in TBHP solution.

3-hydroxy-2,2-dimethylpropanal (0.12 M) released CO only in TBHP solution. As shown in FIG. 4, initially the CO release was small, but within one day, it reached high levels. This was understood to occur because the dimer initially present in solution equilibrated to the monomer, which was able to generate CO.

Example 5

Preparation of 2-formyl-2-methyl-propylmethanoate (Compound 5) and CO Release From 2-formyl-2-methyl-propylmethanoate in Different Media The preparation of 2-formyl-2-methyl-propylmethanoate (compound 5) was performed according to the methods described by Effenberger et al., Tetrahedron: Assymetry, 6:271-282 (1995).

A solution of hydroxypivaldehyde freshly melted was dissolved in dichloromethane and toluene (⅕ of the total volume) with a final concentration of 0.3 M. The solution was placed in a 40° C. bath to make sure that only the monomer was in solution, and pyridine was added (1.5 eq.) followed by acetic anhydride (3 eq.). The mixture was stirred at 60° C. for 40 hours. Then the reaction mixture was filtered through a short pad of silica gel (5×3 cm) and eluted with dichloromethane to remove the salts. The filtrate was evaporated and the residue was fractionally distilled in vacuo. (bp 75° C./10 Torr). Yield 55%. IR $(cm^{-1})$ v $(cm^{-1})$ 2981, 1745, 1477, 1378, 1243, 1045, 682; $^1$H NMR (300 MHz) δ ppm 9.52 (s, 1H, CHO), 4.12 (s, 2H, CH$_2$), 2.05 (s, 3H, CH$_3$CO$_2$), 1.12 (s, 6H, CH$_3$).

A sample of 2-formyl-2-methyl-propylmethanoate (compound 5), was placed in a 7.5 ml vial and sealed with an appropriate stopper, and the experiments were performed as described above in Example 1.

Figure 5:
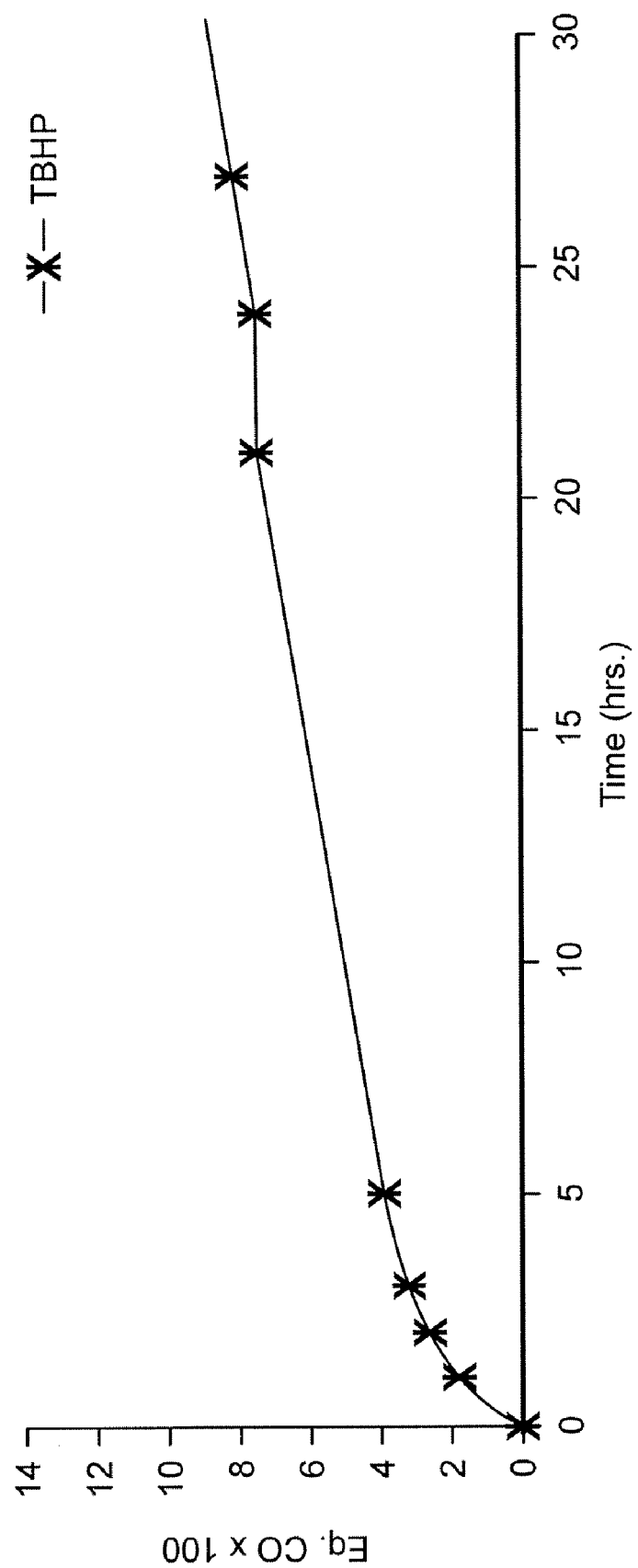
FIG. 5 is a plot showing the kinetics of CO release of 2-formyl-2-methyl-propylmethanoate (compound 5) in TBHP solution.

2-Formyl-2-methyl-propylmethanoate (0.17 M) released CO only in TBHP solution and, as shown in FIG. 5, when compared to the compounds tested in the other Examples, released the lowest amount of CO.

Example 6

Preparation of 2,2-dimethyl-3-(p-methylphenyl)propanal (Compound 6) and CO Release From 2,2-dimethyl-3-(p-methylphenyl)propanal in Different Media The preparation of 2,2-dimethyl-3-(p-methylphenyl)propanal (compound 6) was performed according to the methods described in European Patent No. 0076493.

A solution of potassium hydroxide (224 g, 4 mol) and 10 g of ALIQUAT 336 (tricapryl-methyl-ammonium chloride) was stirred in 125 ml of water and 200 ml of toluene and heated to boiling. With continuing boiling, a solution of benzyl chloride (402 g, 3.2 mol) and isobutyraldehyde (256 g, 3.6 mol) was added dropwise. After 14 hours of stirring at boiling temperature, the solution was cooled down to room temperature and diluted with 300 ml of water. The aqueous phase was extracted with diethyl ether. The combined organic phases were washed and concentrated. The crude product (yellow oil) gave after distillation over a fractionated column a colourless oil. Yield 69%. IR v $(cm^{-1})$=2977, 2933, 2727, 1729, 1515, 1463, 1201, 819;$^1$H-NMR: δ=9.51 (s, 1H, CHO), 6.92 (d, J=1.8, 2H, Ar), 6.89 (d, J=1.8, 2H Ar), 2.67 (s, 2H, CH$_2$), 2.24 (s, 3H, Ph-CH$_3$), 0.97 (s, 6H, 2×CH$_3$).

A sample of the 2,2-dimethyl-3-(p-methylphenyl)propanal (compound 6), was placed in a 7.5 ml vial, sealed with an appropriate stopper, and the experiments were performed as described above in Example 1.

Figure 6:
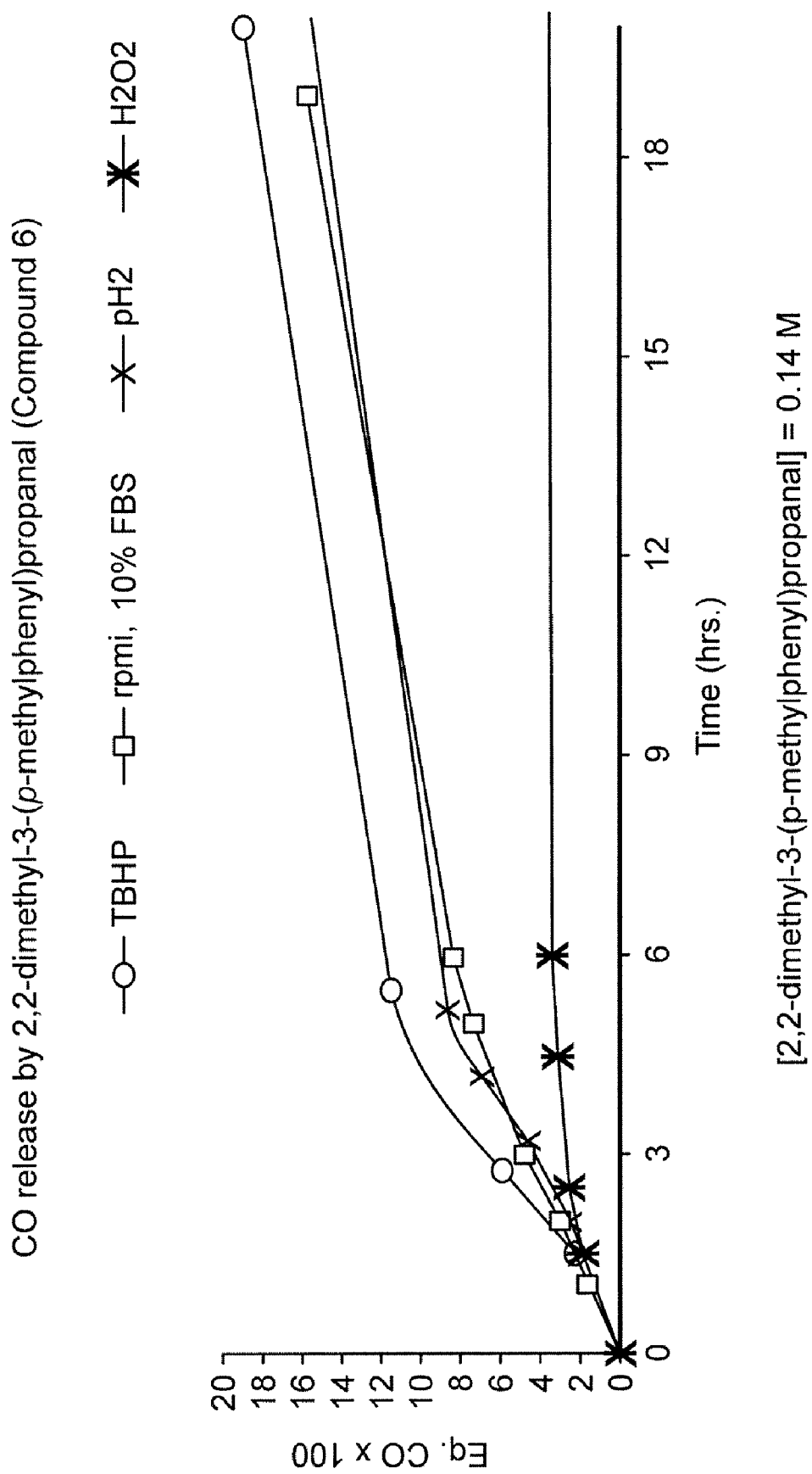
FIG. 6 is a plot showing the kinetics of CO release of 2,2-dimethyl-3-(p-methylphenyl)propanal (compound 6) in TBHP, $H_2O_2$, pH 2 and rpmi solutions.

As shown in FIG. 6, 2,2-dimethyl-3-(p-methylphenyl)propanal (0.14 M) released CO in all media tested except H$_2$O$_2$ solution.

Example 7

Preparation of 2-methyl-2-phenylpropionaldehyde (Compound 7) and CO Release From -methyl-2-phenylpropionaldehyde in Different Media The preparation of 2-methyl-2-phenylpropionaldehyde (compound 7) was performed according to the methods described by Goto et al., J. Inorg. Biochem. 69:241-247 (1988). To a THF (200 ml) suspension of sodium hydride (7.2 g, 193 mmol) (60% oil dispersion) cooled in an ice bath was added dropwise 2-phenylpropionaldehyde (24 ml, 179 mmol). After stirring for 10 minutes, iodomethane (12 ml, 193 mmol) in THF (10 ml) was added dropwise, and the solution turned progressively yellow. The mixture was stirred at room temperature overnight and kept away from light. The next day, water (20 ml) was added and the resultant THF/aqueous solution was extracted three times with diethyl ether (3×100 ml). The combined organic phases were dried over Na$_2$SO$_4$, filtered and the solvent evaporated. The remaining yellow liquid was purified by distillation under reduced pressure (20 mmHg, 82-85° C.) to give a colourless oil in 63% yield. IR v $(cm^-)$=3457, 2979, 2816, 2711, 1602, 1497, 1253, 1030, 838, 701; $^1$H-NMR: δ=9.51 (s, 1H, CHO), 7.20-7.40 (m, 5H, Ar), 1.47 (s, 6H, 2×CH$_3$).

A sample of 2-methyl-2-phenylpropionaldehyde (compound 7) was placed in a 7.5 ml vial, sealed with an appropriate stopper, and the experiments were performed as described above in Example 1.

Figure 7:
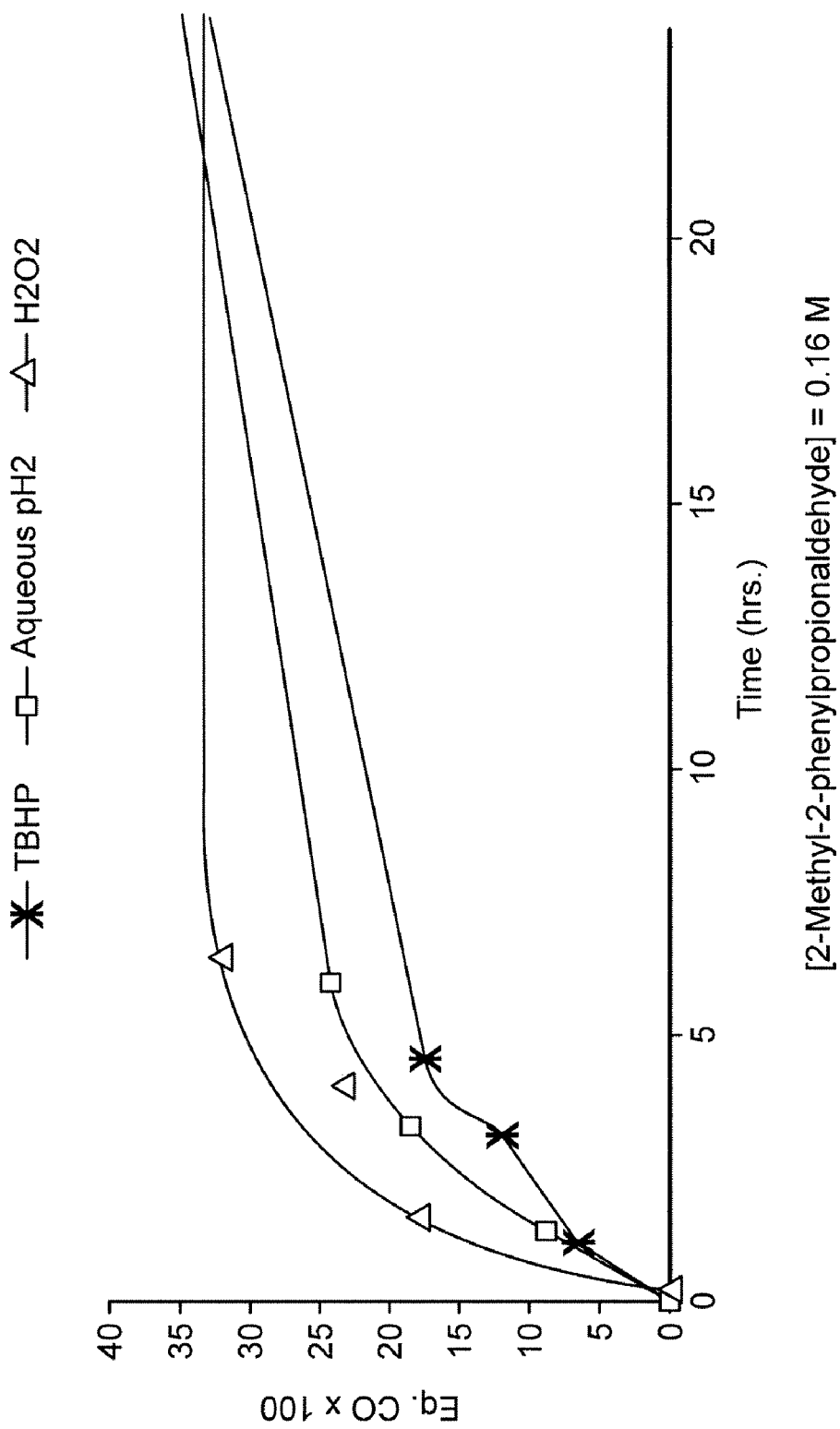
FIG. 7 is a plot showing the kinetics of CO release of 2-methyl-2-phenylpropionaldehyde (compound 7) in TBHP, $H_2O_2$ and pH 2 solutions.

As shown in FIG. 7, 2-methyl-2-phenylpropionaldehyde (0.16 M) released CO in all media tested except rpmi solution.

Figure 8:
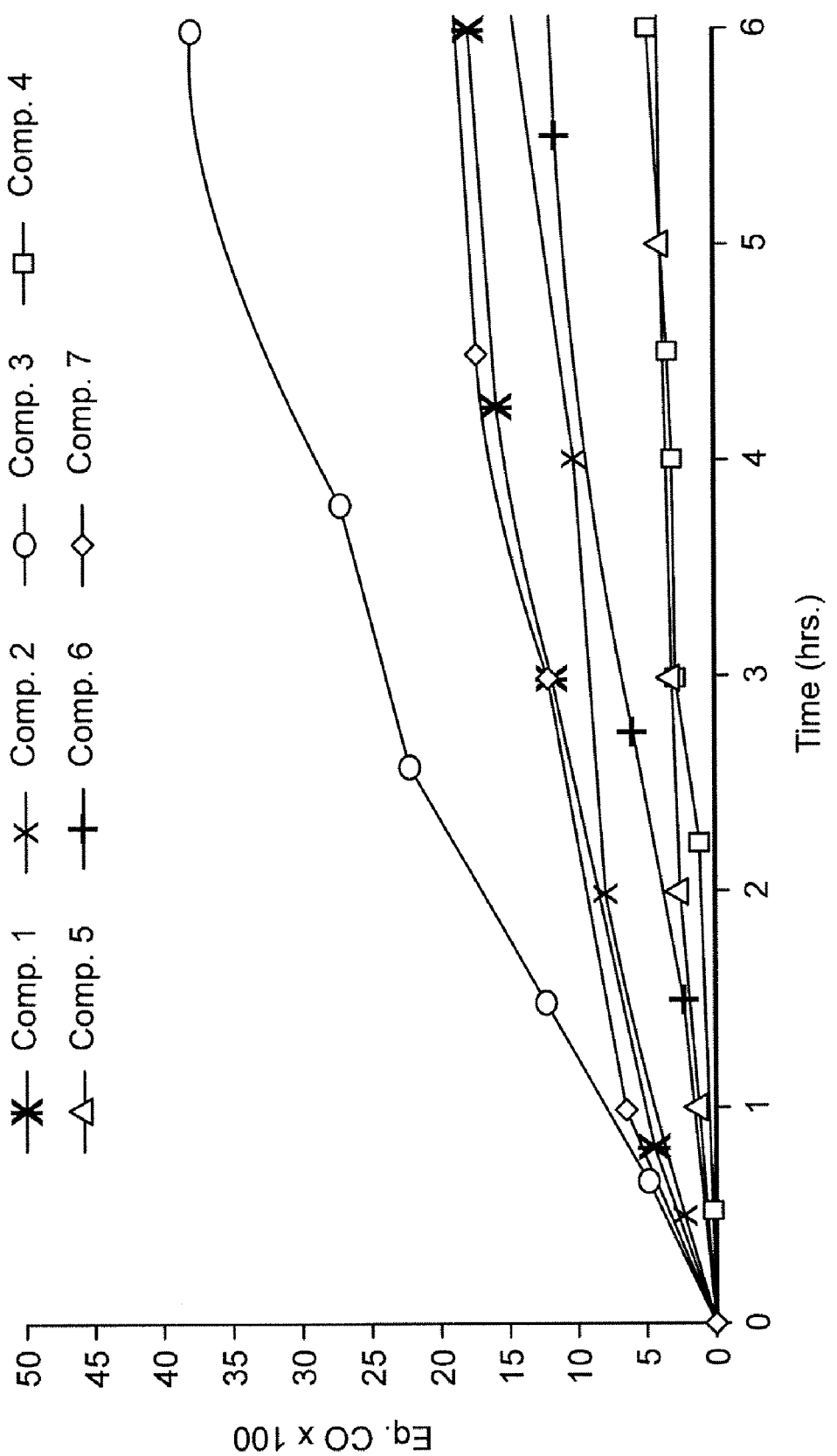
FIG. 8 is an overview plot showing the kinetics of CO release for compounds 1-7 in the first 6 hours in TBHP solutions.
Figure 9:
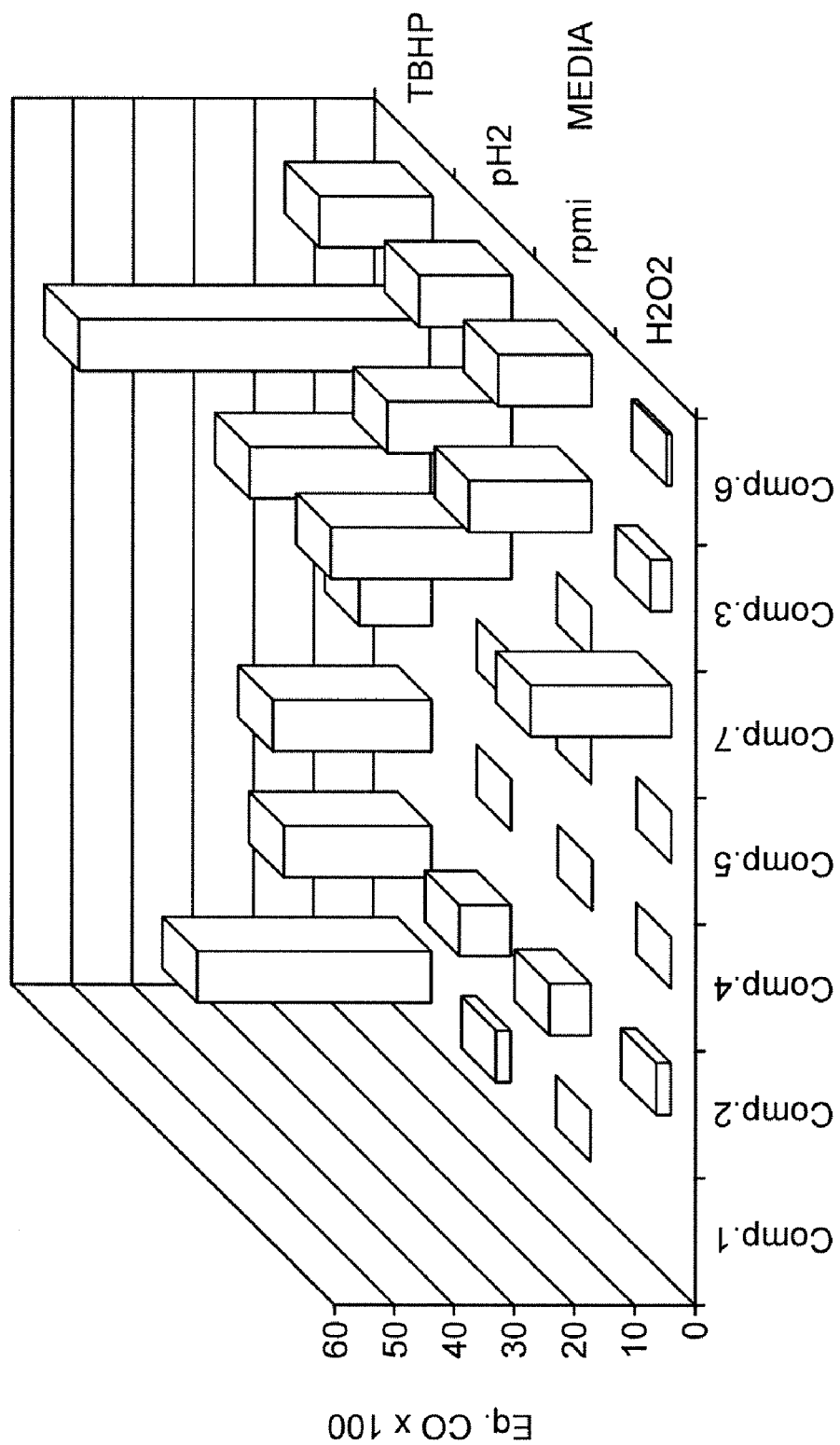
FIG. 9 presents an overview of the data on the kinetics of CO release for compounds 1-7 after 24 hours in different media.

FIGS. 8 and 9 summarize the kinetics of CO release for the aldehydes tested as described in Examples 1-7. As illustrated in FIG. 9, the aldehydes showed different CO release abilities. They all released CO in the presence of tert-butyl-hydroperoxide medium (TBHP) (FIG. 8). TBHP was always present in excess, above 16 equivalents. As explained above in Example 1, the excess TBHP did not affect CO release for concentrations above 8 equivalents. TBHP is a very efficient radical initiator that abstracts the hydrogen atom of the aldehydic function, and initiates the radical decarbonylation process (Berman et al., J. Am. Chem. Soc. 85:4010-4013 (1963)). The same did not occur in the hydrogen peroxide medium (H$_2$O$_2$), a less efficient radical initiator, where only compound 7 responded significantly to decarbonylation. Compound 7 was expected to be more reactive, because decarbonylation produces a more stable tertiary radical, stabilized by both resonance hyperconjugation and conjugation.

Compounds 3, 6 and 7 decarbonylated significantly in acidic aqueous solutions. It is known that some aromatic aldehydes can decarbonylate in acidic media through an ionic mechanism (Bukket, J. Am. Chem. Soc. 81:3924 (1959)), and the same could happen for compounds 3, 6 and 7. However, the addition of a radical trap, 2,6-di-tert-butylphenol, inhibited the decarbonylation process, thus suggesting a radical mechanism. The same is true for the decarbonylation in rpmi observed for compounds 2, 3 and 6.

Experiments on CO release in various media as described in Examples 1-7 are useful for predicting how aldehydes will behave in vivo. For example, testing the CO release in different media as illustrated allows for the identification of aldehydes that selectively release CO in the presence of reactive oxygen species (e.g., represented by $H_2O_2$ and TBHP, the latter being more reactive), but do not release CO in a general aqueous environment under normal physiological conditions (e.g., represented by rpmi (plasma) and pH 2 (stomach)). Reactive oxygen species are known to exist in inflamed tissues at concentrations of about 1 mM (B. Halliwell & J.M.C. Gutteridge, *Free Radicals in Biology and Medicine*, Oxford University Press, $3^{rd}$ Ed., 1999).

Example 8

Anti-Arthritic Activity of Compounds 1 and 2

Adjuvant arthritis was induced in outbred Sprague-Dawley rats by intradermal injection into the subplantar area of the right hind paw of 0.1 ml of a 10 mg/ml suspension of Mycobacterium butyricum, killed and dried in Freund's incomplete adjuvant. Treatment was initiated 10 days after disease induction at the time of disease onset. Groups of 7 rats received intraperitoneal injections of compound 1 and compound 2 in 1 ml PBS, each at a dose of 100 mg/kg/day for 20 days. A control group of 7 rats received no treatment. Progression of arthritis was monitored by daily measurements of right and left paw volumes by a water displacement method using a plethysmometer, by daily measurements of the ankle circumference with a flexible strip, and by determination of the arthritic index based on levels of erythema and oedema of the entire paws and digits, number of joints involved, spondylosis, lesions on the tail, movement capacity and infections. The maximum possible score was 11.

Figure 10:
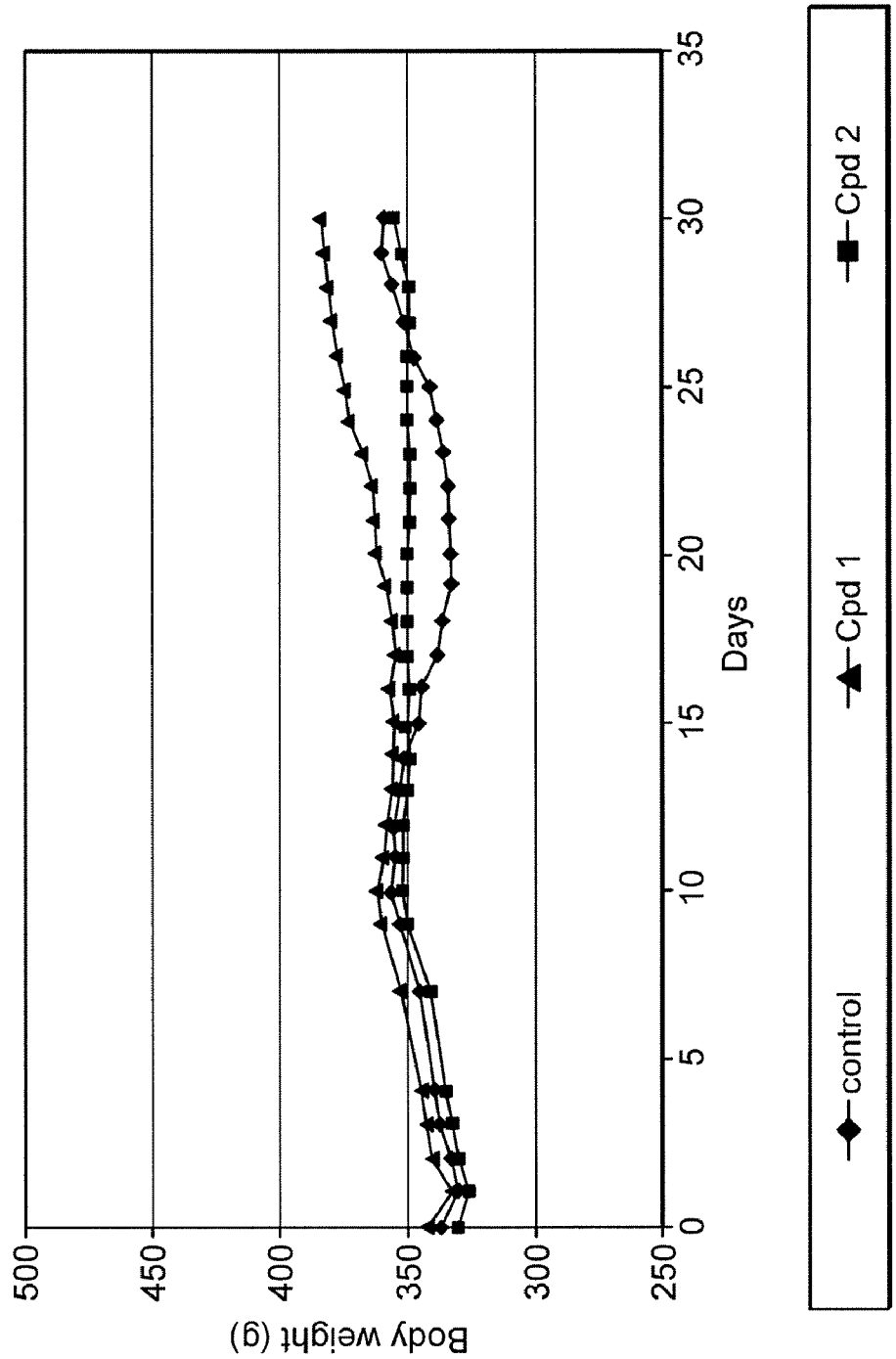
FIG. 10 is a plot showing the changes in body weight in untreated (control) and treated (compound 1 or compound 2) Sprague Dawley rats after the induction of adjuvant arthritis.
Figure 11A:
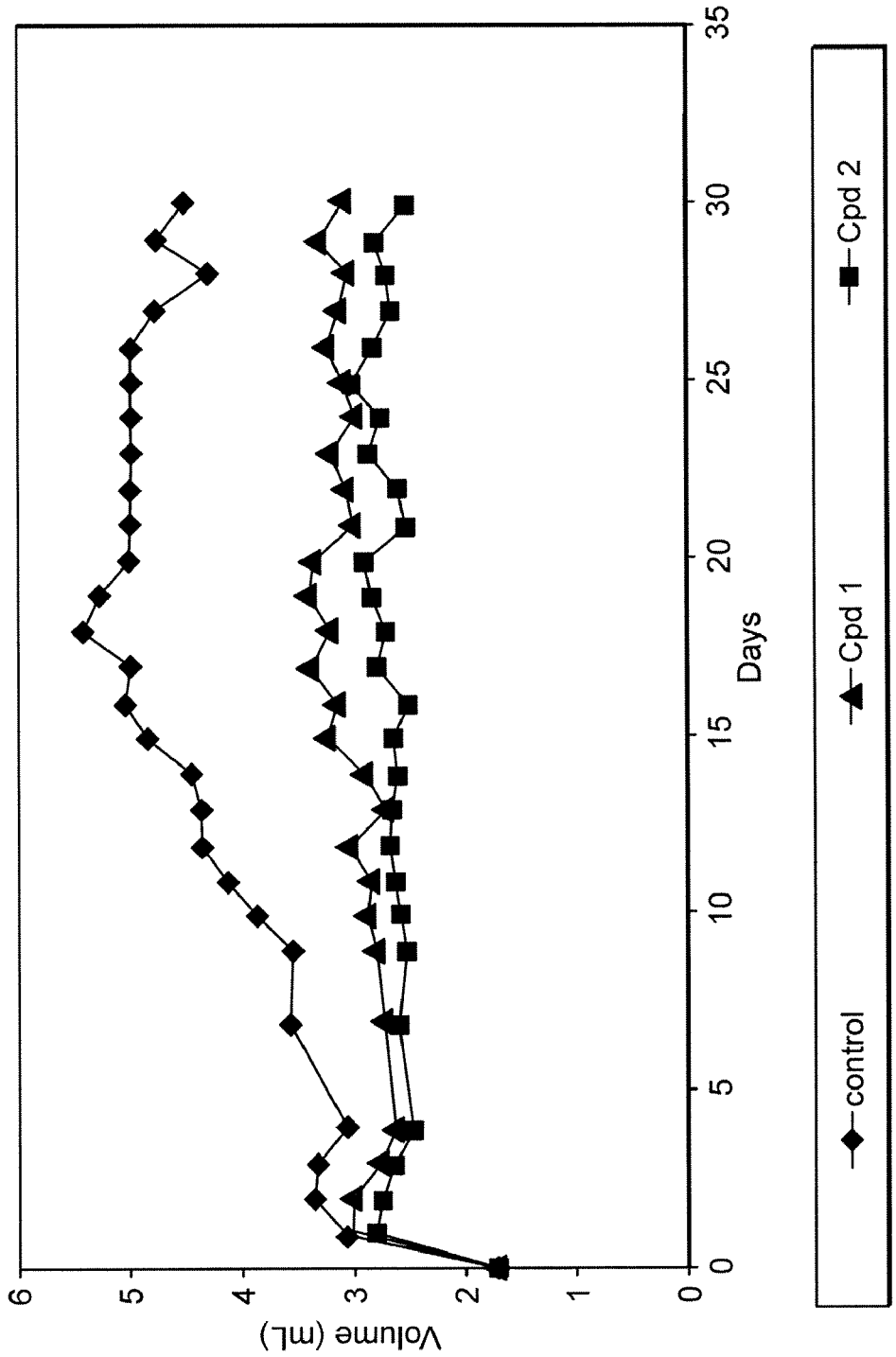
FIGS. 11A-D are plots showing the changes in the volume of the right paw (11A) and the left paw (11B), and of the circumference of the right paw (11C) and the left paw (11D) in untreated (control) and treated (compound 1 or compound 2) Sprague Dawley rats after the induction of adjuvant arthritis.
Figure 11B:
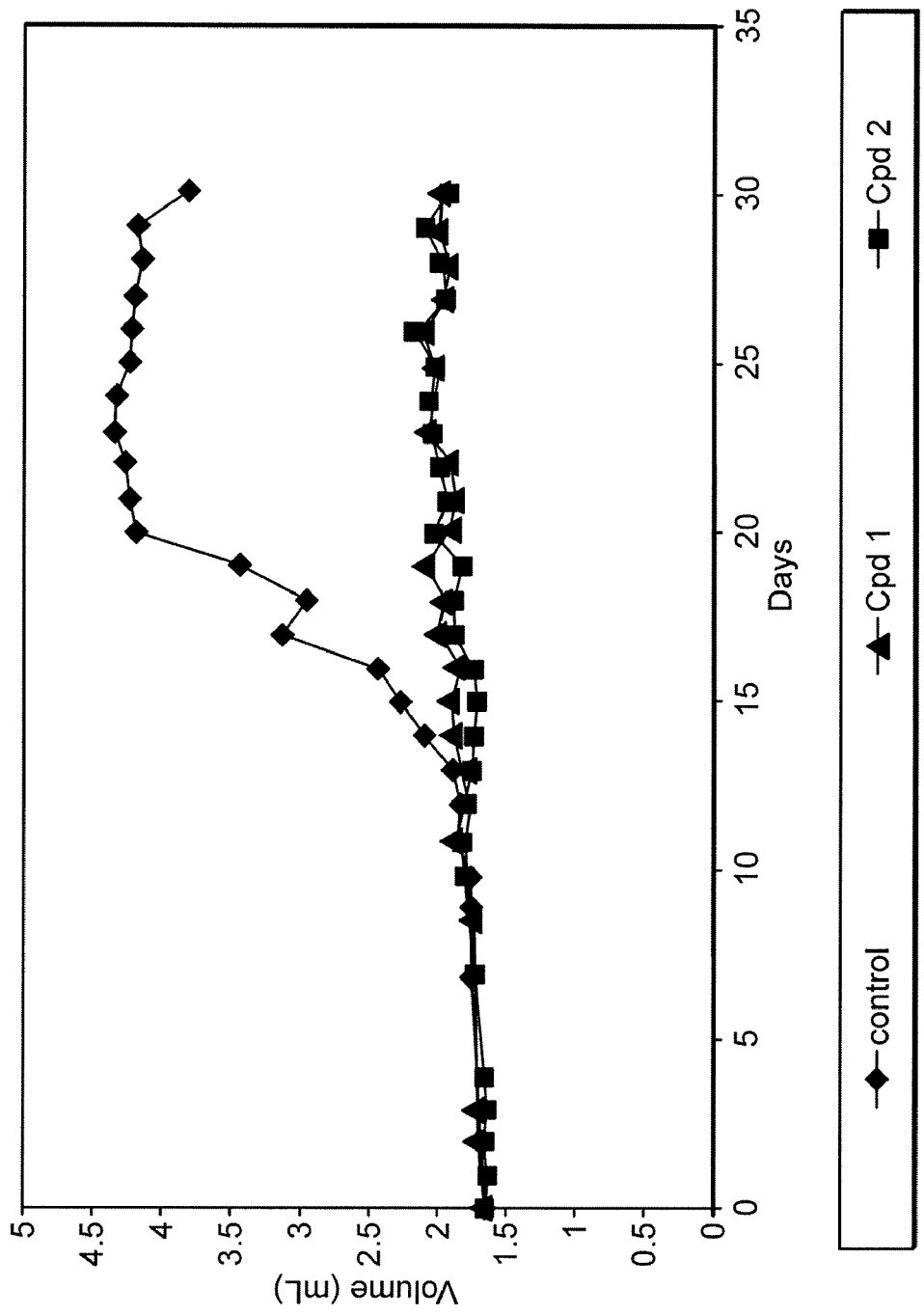
Figure 11C:
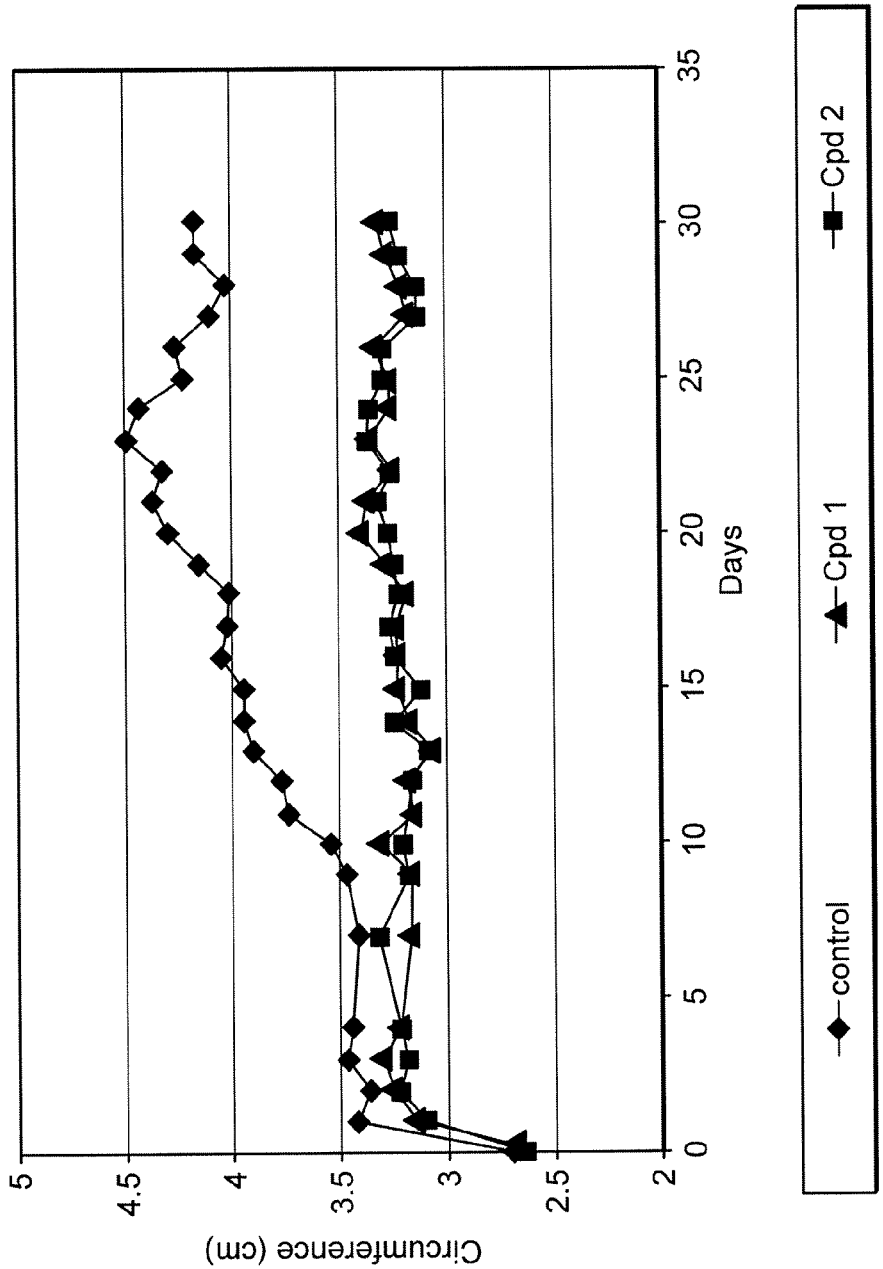
Figure 11D:
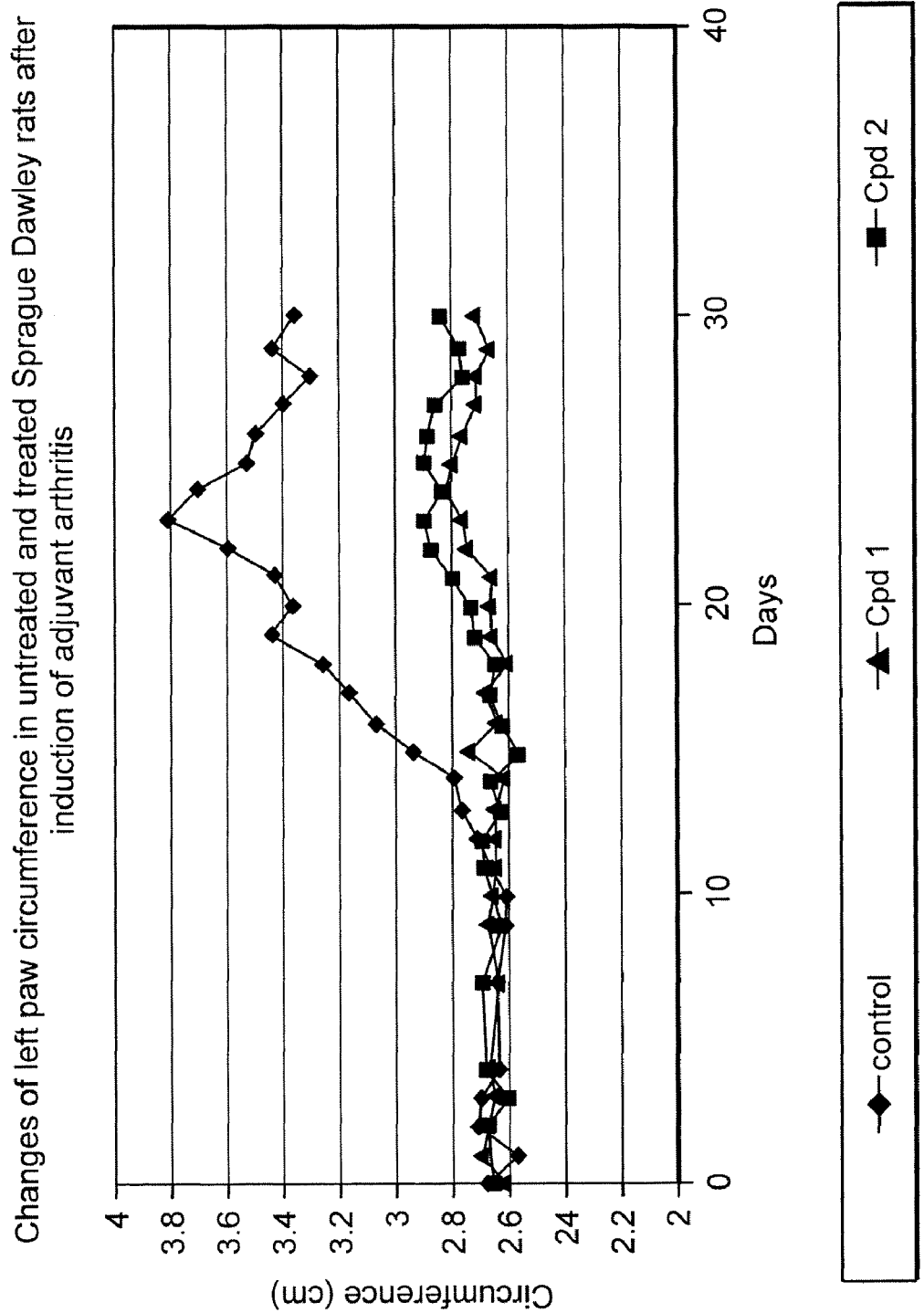
Figure 12:
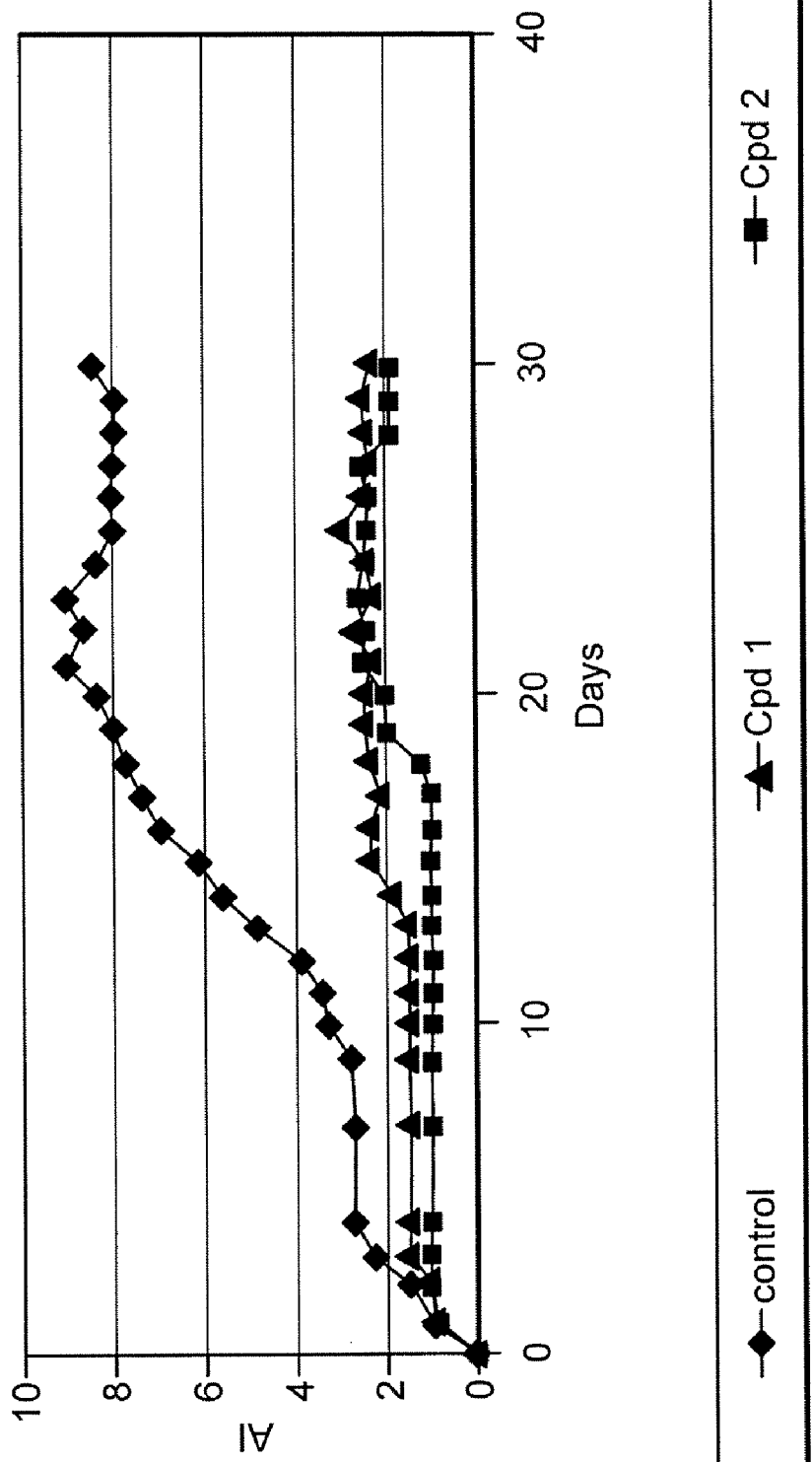
FIG. 12 is a plot showing changes in the arthritic index in untreated (control) and treated (compound 1 or compound 2) Sprague Dawley rats after the induction of adjuvant arthritis.

As shown in FIG. 10, untreated control rats lost body weight after the onset of the disease on day 10 after disease induction. No loss of body weight was observed in the rats treated with compounds 1 and 2. Both compounds also prevented the increase in paw volume and circumference that was observed in untreated control rats (FIGS. 11A (right paw volume), 11B (left paw volume), 11C (right paw circumference) and 11D (left paw circumference)). The arthritic index reached values above 8 in untreated rats, and remained below 3 in the treated animals (FIG. 12).

Example 9

Anti-Arthritic Activity of Compounds 1 and 7

Adjuvant arthritis was induced in Lewis rats by a single intradermal injection (0.1 ml) of heat killed Mycobacterium tuberculosis H37Ra (0.3 mg) in Freund's incomplete adjuvant into the right footpad. Treatments were initiated at day 10 after disease induction, and consisted of daily injections for 30 consecutive days. Groups of 11 rats were treated with compound 1 (100 mg/kg), compound 1 (25 mg/kg), compound 7 (100 m/kg), compound 7 (25 mg/kg), vehicle (carboxymethyl cellulose, 0.5% and Tween 80 (polyoxyethylene-20 sorbitan monooleate), 0.5%), dexamethasone (DEX, a glucocorticoid anti-inflammatory agent, 0.3 mg/kg), and one group remained untreated. The body weight was determined daily. The course of the disease was monitored by measurement of paw volume using plethysmometry on a weekly basis, and by macroscopic assessment of the levels of erythema and oedema of the entire paws and digits and number of joints involved. The arthritic index was calculated for each rat by adding the 4 scores of individual paws.

Figure 13:
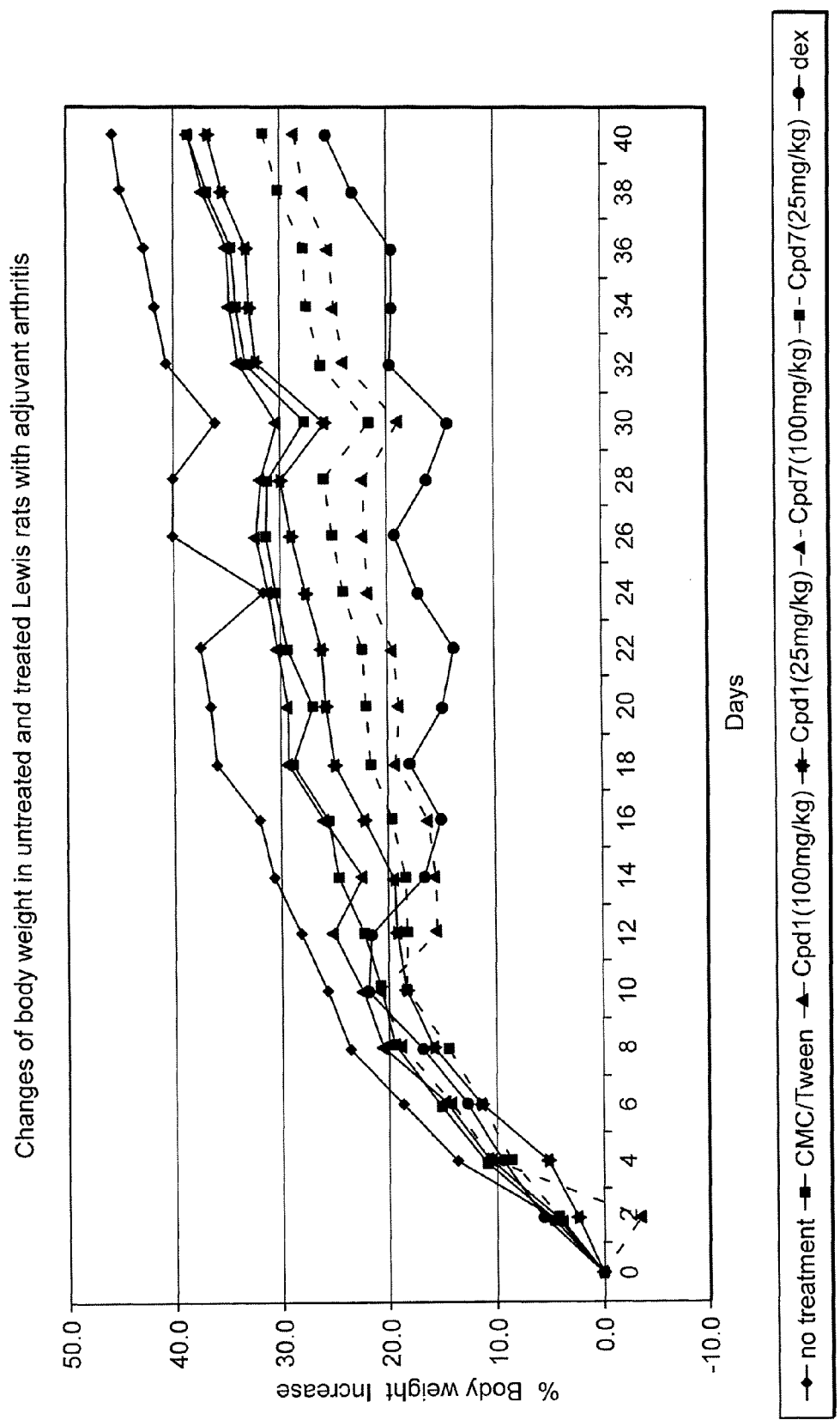
FIG. 13 is a plot showing changes of body weight in untreated and treated Lewis rats after induction of adjuvant arthritis. The treatment groups included compound 1 (100 mg/kg), compound 1 (25 mg/kg), compound 7 (100 mg/kg), compound 7 (25 mg/kg), dexamethasone, and vehicle (carboxymethylcellulose/Tween 80).

As shown in FIG. 13, the increase in body weight of untreated rats was 45.7% by day 40 of the study. The increase in body weight of rats treated with compound 7 (100 mg/kg), compound 7 (25 mg/kg), and dexamethasone was 31.6%, 28.6%, and 25.7%, respectively. The increase in body weight of rats treated with compound 1 (100 mg/kg) and compound 1 (25 mg/kg) was 40% and 38.7%, respectively. This increase in the latter groups was similar to that observed in vehicle treated rats (36.8%).

Figure 14:
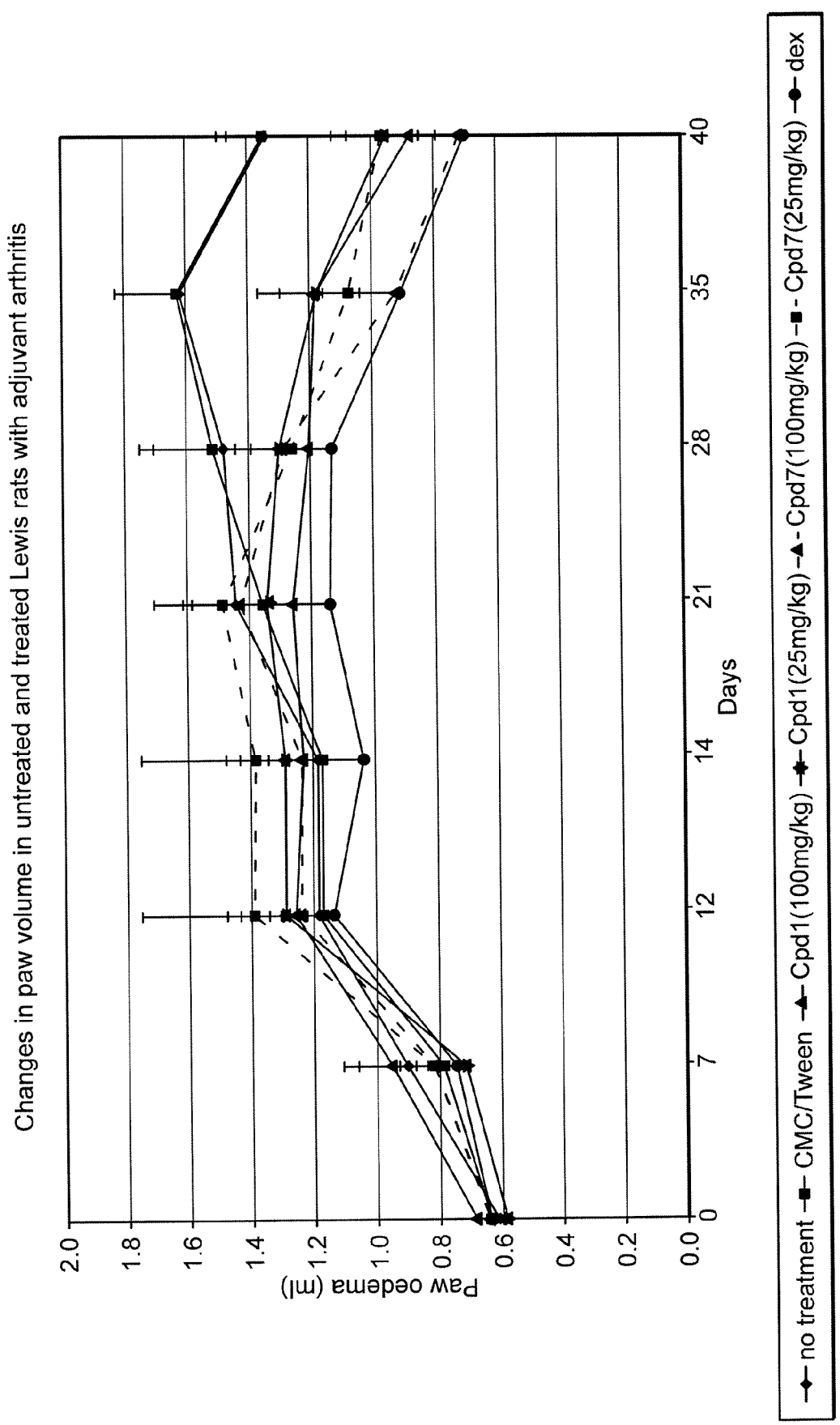
FIG. 14 is a plot showing changes in paw volume in untreated and treated Lewis rats after the induction of adjuvant arthritis. The treatment groups included compound 1 (100 mg/kg), compound 1 (25 mg/kg), compound 7 (100 mg/kg), compound 7 (25 mg/kg), dexamethasone, and vehicle (carboxymethylcellulose/Tween 80).
Figure 15:
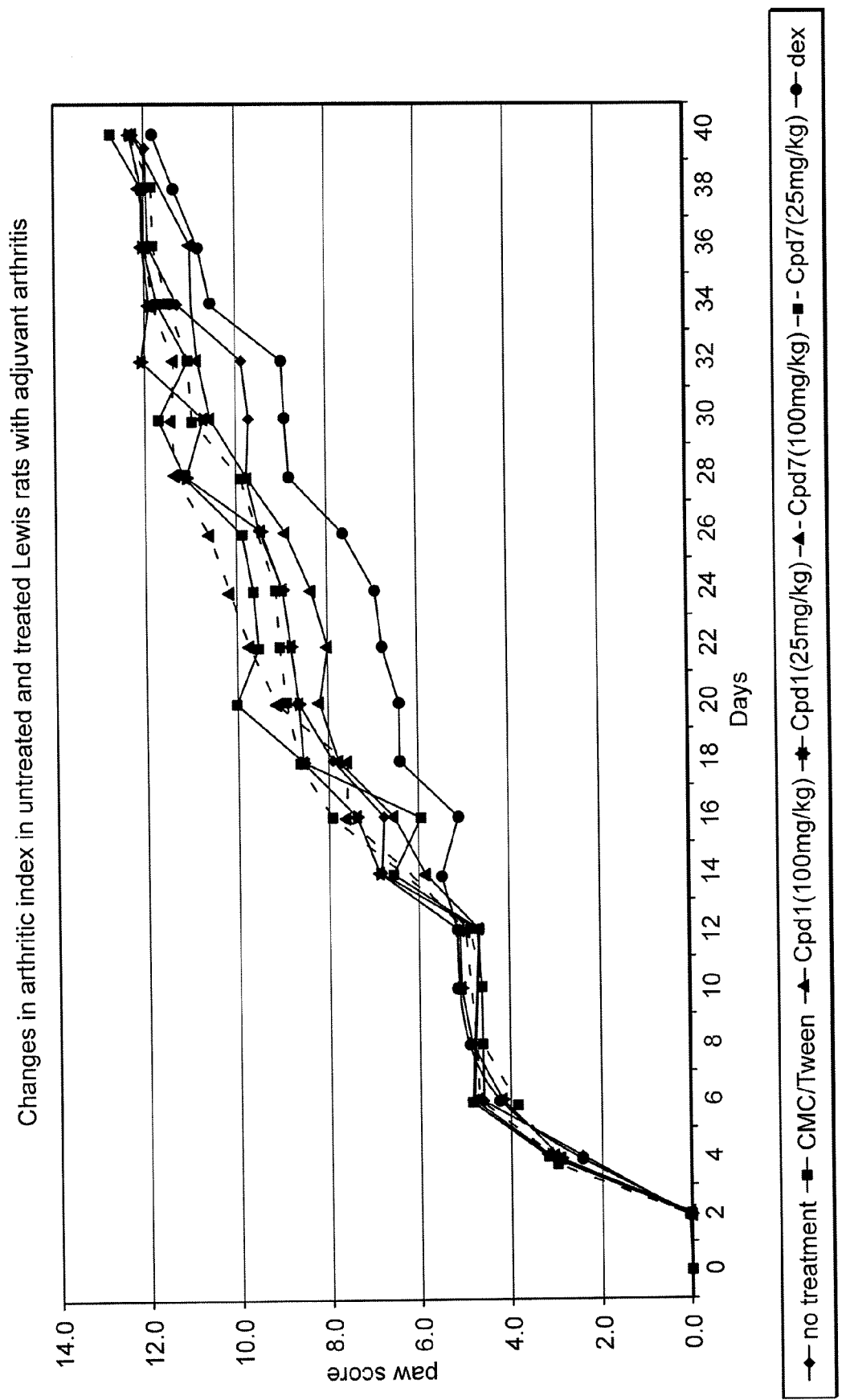
FIG. 15 is a plot showing changes in arthritic index in untreated and treated Lewis rats after the induction of adjuvant arthritis. The treatment groups included compound 1 (100 mg/kg), compound 1 (25 mg/kg), compound 7 (100 mg/kg), compound 7 (25 mg/kg), dexamethasone, and vehicle (carboxymethylcellulose/Tween 80).

Treatment with compounds 1 and 7 reduced the increase in paw volume as compared to treatment with vehicle or with untreated rats (FIG. 14). This effect was significant from day 28 on. The reduction in paw volume in rats treated with compound 7 (100 mg/kg) was comparable to that seen in rats treated with dexamethasone. The arthritic score was only slightly influenced, and not in a continuous fashion, by the treatment with compound 1 and compound 7 (FIG. 15). A significant inhibition of arthritic score relative to vehicle treated rats was observed on days 14, 18, 28, 30 and 36 for compound 1 (100 mg/kg), on days 16 and 30 for compound 1 (25 mg/kg), on day 14 for compound 7 (100 mg/kg) and on days 14 and 28 for compound 7 (25 mg/kg).

Example 10

Preparation of 2-tert-butyl-thiazolidine-4-carboxylic acid (Compound 9) and CO Release from 2-tert-butyl-thiazolidine-4-carboxylic acid in TBHP 2-tert-butylthiazolidine-4-carboxylic acid (compound 9)

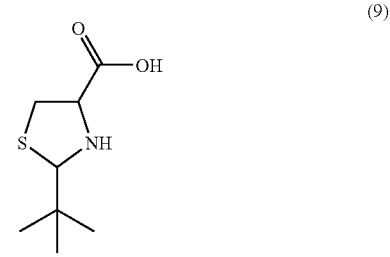

(9)

was synthesized and tested for CO release in TBHP. The compound was prepared as illustrated in equation 15:

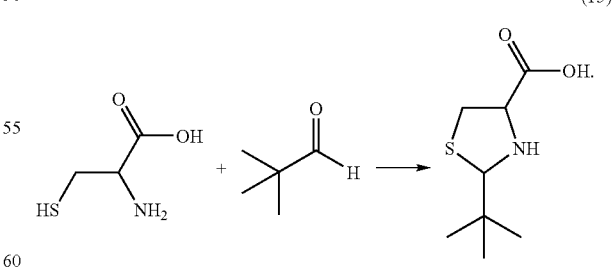

(15)

Specifically, the preparation of 2(RS)-tert-butyl-thiazolidine-4(R)-carboxylic acid was performed by a method related to that described by Nagasawa et al., *J. Biochem. Mol. Tox.* 16:235-244 (2002). L-cysteine (3.28 g) and trimethylacetaldehyde (3.56 ml, 1.2 eq) were mixed in 40 ml of methanol. The solution was stirred for 5 hours at room temperature, and the solvents evaporated to yield a white powder. Elemental analysis Exp (Calc) C: 50.89 (50.76); H: 7.96 (7.99); N 7.46 (7.40); S 17.33 (16.94); IR ν (cm⁻)=3455, 3065, 2966, 1644, 1481, 1360, 1305, 1202, 859, 619; $^1$H-NMR (D$_2$O) δ: 4.71(d, J=1.2 Hz, 0.4H, S—CH—NH), 4.64 (d, J=0.6 Hz, 0.6H, S—CH—NH), 4.58-4.57 (m, 0.4H, CH$_2$—CH×—NH), 4.3-4.29 (m, 0.6H, CH2—CH—NH), 3.30 (m, 2H, CH$_2$), 1.0 (s, 0.6×(9H), (CH$_3$)$_3$), and 0.98 (s, 0.4×(9H), (CH$_3$)$_3$).

A sample of 2-tert-butyl-thiazolidine-4-carboxylic acid (compound 9), was placed in a 7.5 ml vial and sealed with an appropriate stopper. 1.5 ml of rpmi and 0.5 ml of TBHP were added, and the vial was placed at 37° C. with orbital stirring. At the appropriate time, 250 μl of the gas mixture was analysed as described for Example 1.

Figure 16:
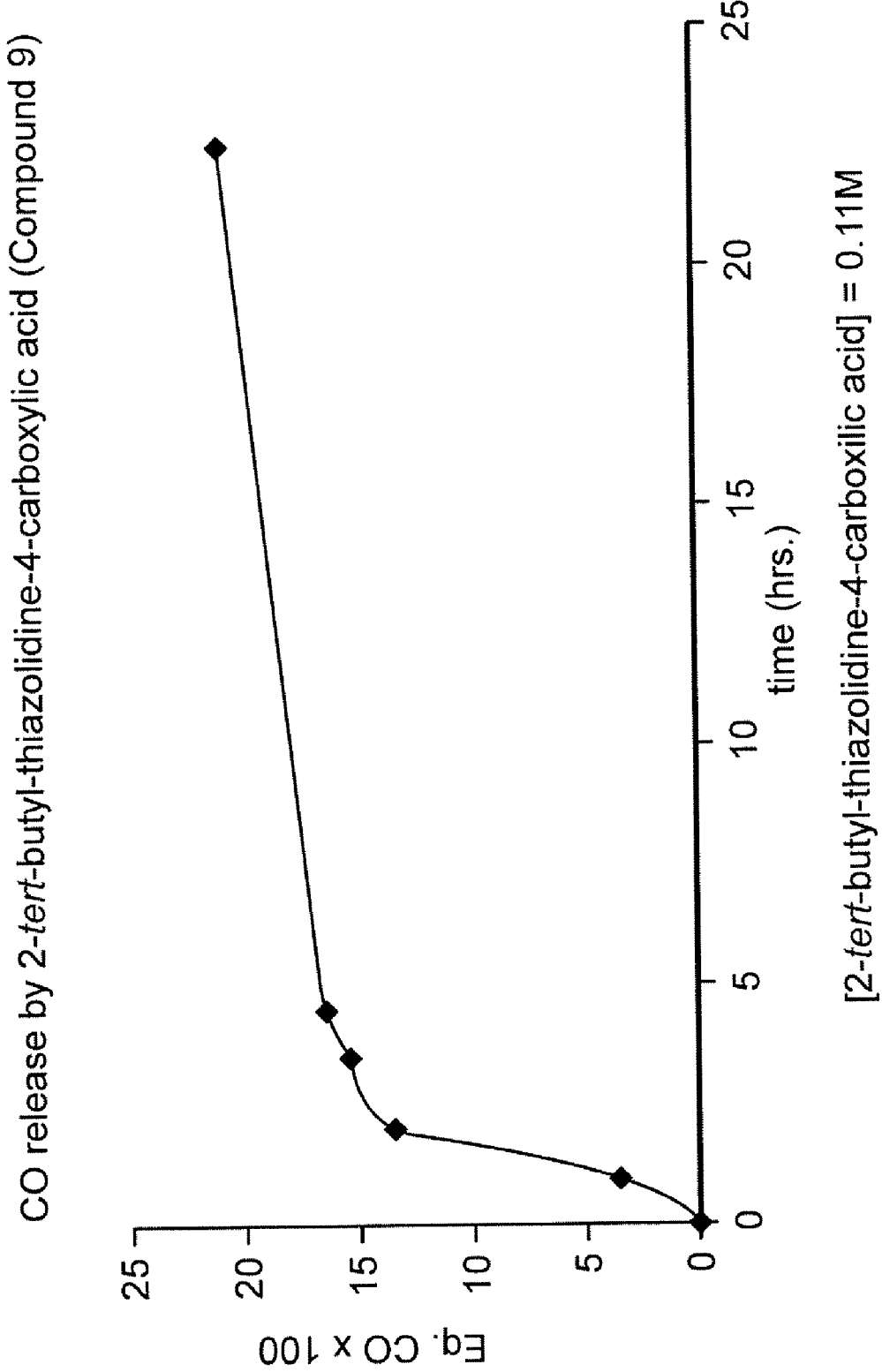
FIG. 16 is a plot showing the kinetics of CO release of 2-tert-butyl-thiazolidine-4-carboxylic acid (compound 9) in TBHP plus rpmi solution.

As shown in FIG. 16, 2-tert-butyl-thiazolidine-4-carboxylic acid (0.11 M) released CO under these conditions. The CO release was fast within the first 6 hours, reaching values around 16%, and then slowed down, reaching 20% within one day.

Example 11

Preparation of 2-tert-butyl-thiazolidine-4-carboxylic acid methyl ester (Compound 10) and CO Release From 2-tert-butyl-thiazolidine-4-carboxylic acid methyl ester in TBHP 2-tert-butyl-thiazolidine-4-carboxylic acid methyl ester (compound 10)

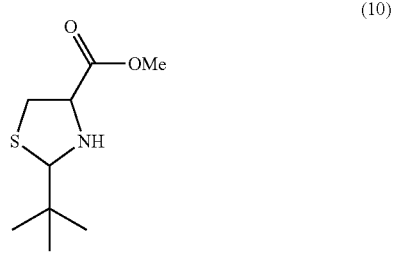

(10)

was synthesized and tested for CO release in TBHP. The compound was prepared as illustrated in equation 16:

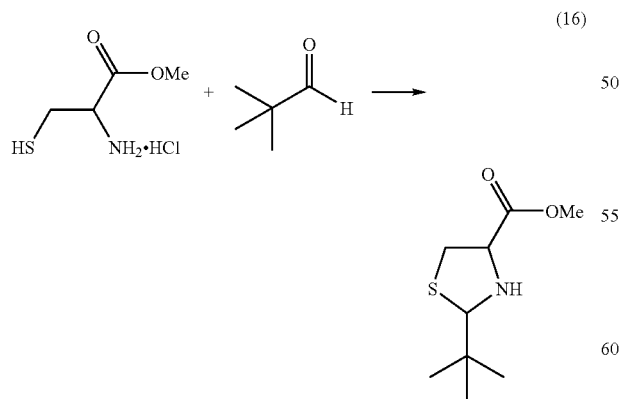

(16)

Specifically, the preparation of 2(RS)-tert-butyl-thiazolidine-4(R)-carboxylic acid methyl ester (compound 10) was performed according to the methods described in U.S. Pat. No. 6,251,927. L-cysteine methyl ester hydrochloride (1.61 g, 9.2 mmol), trimethylacetaldehyde (1 ml, 1.1 eq) and triethylamine (1 eq., 9.2 mmol, 1.28 ml) were mixed in 20 ml of water. The solution was stirred at room temperature for two days, and a transparent and oily material deposited at the bottom of the flask. Dichloromethane was added and the mixture extracted. The combined organic phases were dried with Na$_2$SO$_4$ and the solvent evaporated to yield a transparent oil. Elemental analysis Exp (Calc) C: 52.86 (53.17); H: 7.95 (8.43); N 6.84 (6.89); S 15.43 (15.77); IR ν (cm-1)=3330, 2967, 2875, 1481, 1366, 1204, 836, 719; $^1$H-NMR (D$_2$O) δ: 4.47(s, 0.3H, S—CH—NH), 4.40 (d, J=3.3 Hz, 0.7H, S—CH—NH), 4.10-4.08 (m, 0.3H, CH$_2$—CH—NH), 3.80-3.70 (m, 0.6H, CH$_2$—CH—NH), 3.73 (s, 3H, OCH$_3$), 3.23-2.24 (m, 2H, CH$_2$), 1.03 (s, 0.7×(9H), (CH$_3$)$_3$), and 0.93 (s, 0.3×(9H), (CH$_3$)$_3$).

A sample of the 2-tert-butyl-thiazolidine-4-carboxylic acid methyl ester (compound 10), was placed in a 7.5 ml vial and sealed with an appropriate stopper, and the CO release experiment was performed as described above in Example 10.

Figure 17:
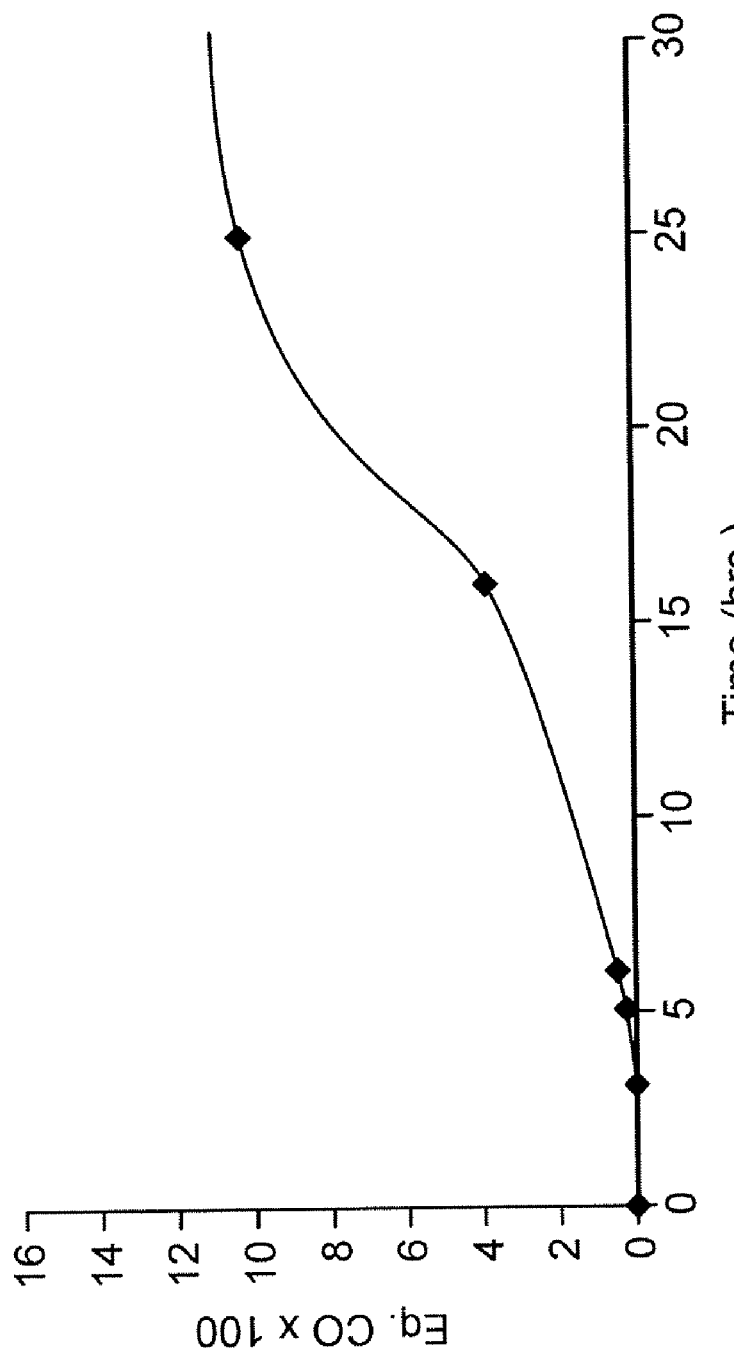
FIG. 17 is a plot showing the kinetics of CO release of 2-tert-butyl-thiazolidine-4-carboxylic acid methyl ester (compound 10) in TBHP plus rpmi solution.

As shown in FIG. 17, 2-tert-butyl-thiazolidine-4-carboxylic acid methyl ester (0.1 M) released CO under the test conditions, but the release was very slow, with only 0.3% of CO released after 6 hours. After one day, the maximum CO release was about 10%. These results were likely due to the lower water solubility of compound 10 as compared to compound 9.

Example 12

Preparation of 2-tert-butyl-thiazolidine (Compound 11) and CO Release from 2-tert-butyl-thiazolidine in TBHP 2-tert-butyl-thiazolidine (compound 11)

(11)

was synthesized and tested for CO release in TBHP. The compound was prepared as illustrated in equation 17:

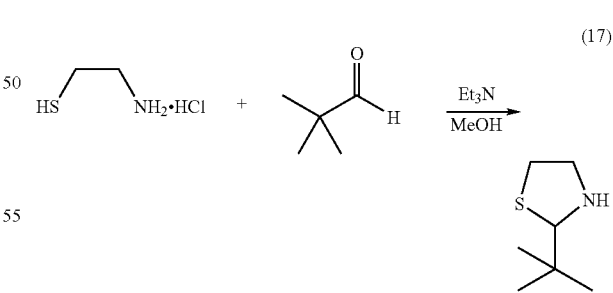

(17)

Specifically, the preparation of 2-(RS)-tert-butyl-thiazolidine was performed according to a method related to that described by Jellum et al., *Anal. Biochem.* 31:339-347 (1969). Cysteamine hydrochloride (2.01 g, 17.69 mmol) and trimethylacetaldehyde (2.35 ml, 1.2 eq.) were mixed in methanol (20 ml) at room temperature. Triethylamine (2.55 ml, 1.05 eq.) was added, and the mixture was stirred for 2 hours at room temperature. The solvent was then removed under vacuum, yielding a white gummy solid. Diethyl ether and aqueous NaHCO₃ saturated were added. The mixture was extracted, and the combined organic phases were dried (Na₂SO₄) and evaporated to yield a transparent oil. IR ν (cm⁻¹)=3321, 2971, 1673, 1482, 1371, 1050, 927, 839; ¹H-NMR (CDCl3) δ: 4.4 (s, 1H, CH), 3.64-3.53 (m, 0.65×2H, NH—CH₂), 2.96-2.80 (m, 2H, S—CH₂), 2.68-2.60 (m, 0.35× 2H, NH—CH₂), 1.03 (s, 0.65×9H, (CH₃)₃), 1.0 (s, 0.35×9H, (CH₃)₃).

A sample of the 2-tert-butyl-thiazolidine (compound 11), was placed in a 7.5 ml vial and sealed with an appropriate stopper, and the CO release experiment was performed as described above in Example 10.

Figure 18:
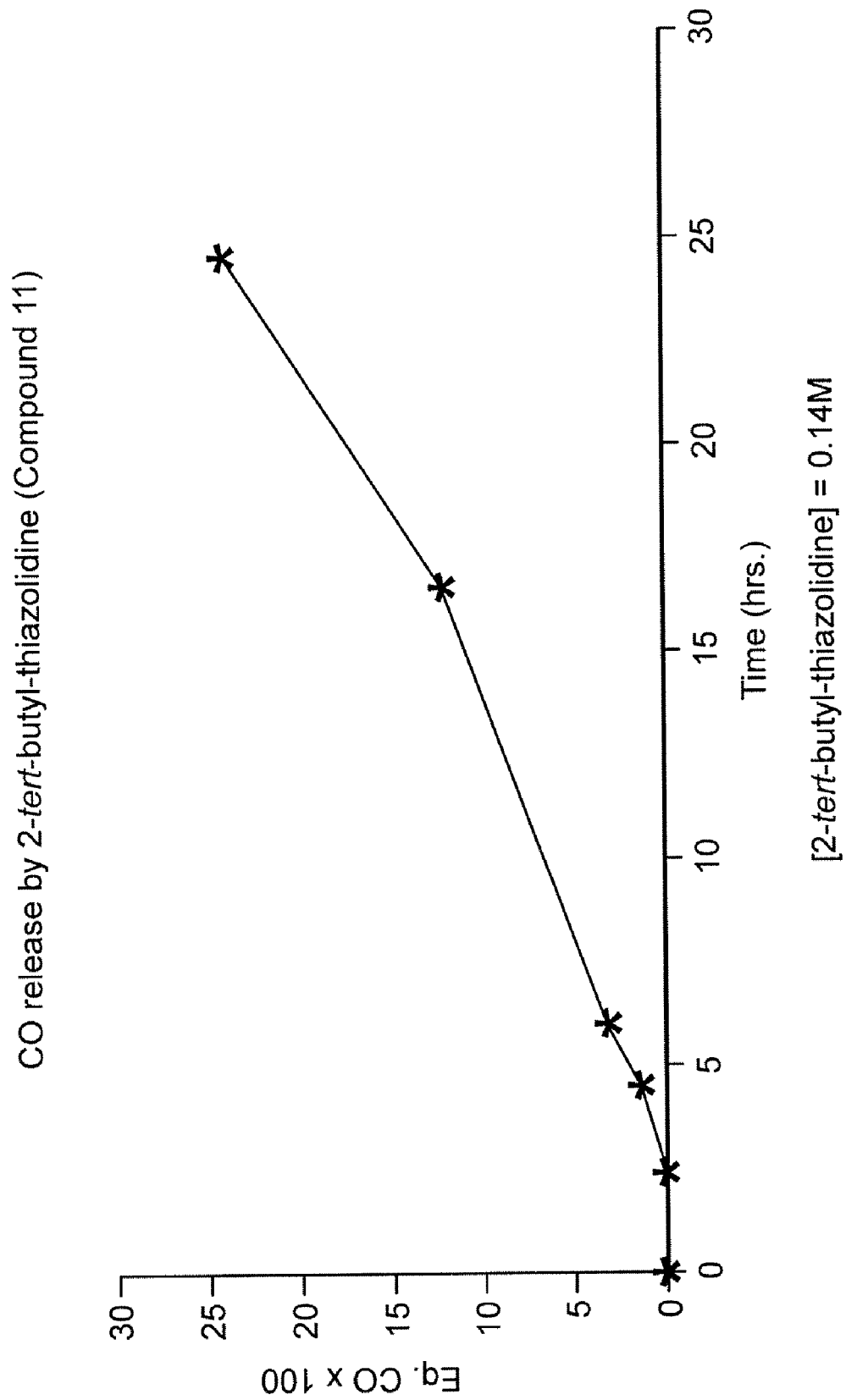
FIG. 18 is a plot showing the kinetics of CO release of 2-tert-butyl-thiazolidine (compound 11) in TBHP plus rpmi solution.

As shown in FIG. 18, 2-tert-butyl-thiazolidine (0.14 M) released CO under these conditions, initially very slowly, then reaching high values of about 25% after one day.

Example 13

Preparation of 2(RS)-tert-butyl-[1,3]thiazinane-4 (RS)-carboxylic acid (Compound 12) and CO Release from 2-tert-butyl-[1,3]thiazinane-4-carboxylic acid in TBHP 2-tert-butyl-[1,3]thiazinane-4-carboxylic acid (compound 12)

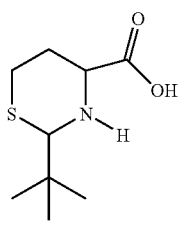
(12)

was synthesized and tested for CO release in TBHP. The compound was prepared as illustrated in equation 18:

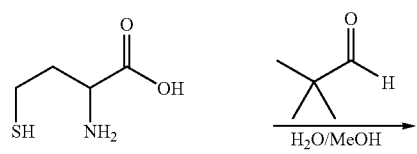
(18)

Specifically, the preparation of 2-tert-butyl-[1,3]thiazinane-4-carboxylic acid was performed according to the procedure used in the preparation of compound 9. DL-Homocysteine (1 g) was dissolved in 10 ml of MeOH and 2 ml of distilled water, and trimethylacetaldehyde (1.2 eq.) was added. The solution was stirred at room temperature for 16 hours, and the solvents evaporated, yielding a white powder. IR ν (cm⁻¹)=3461, 2936, 2858, 1725, 1455, 1263, 1190, 1023, 908, 828. ¹H-NMR (D₂O) δ: 4.28, (s, 0.4×1H, S—CH—NH),  4.17 (s, 0.6×1H, S—CH—NH), 4.02-4.03 (m, 0.4×H, CH₂—CH—NH), 3.7-3.4 (m, 0.6×1H, CH₂—CH—NH), 2.93-2.55 (m, 2H, S—CH₂), 2.49-1.76 (m, 2H, CH₂—CH—NH), 0.98 (s, 0.4×(9H), (CH₃)₃), and 0.96 (s, 0.6× (9H), (CH₃)₃).

A sample of 2-tert-butyl-[1,3]thiazinane-4-carboxylic acid (compound 12) at a concentration of 0.1 M was placed in a 7.5 ml vial and sealed with an appropriate stopper. The CO release experiment was performed as described above in Example 10.

Figure 19:
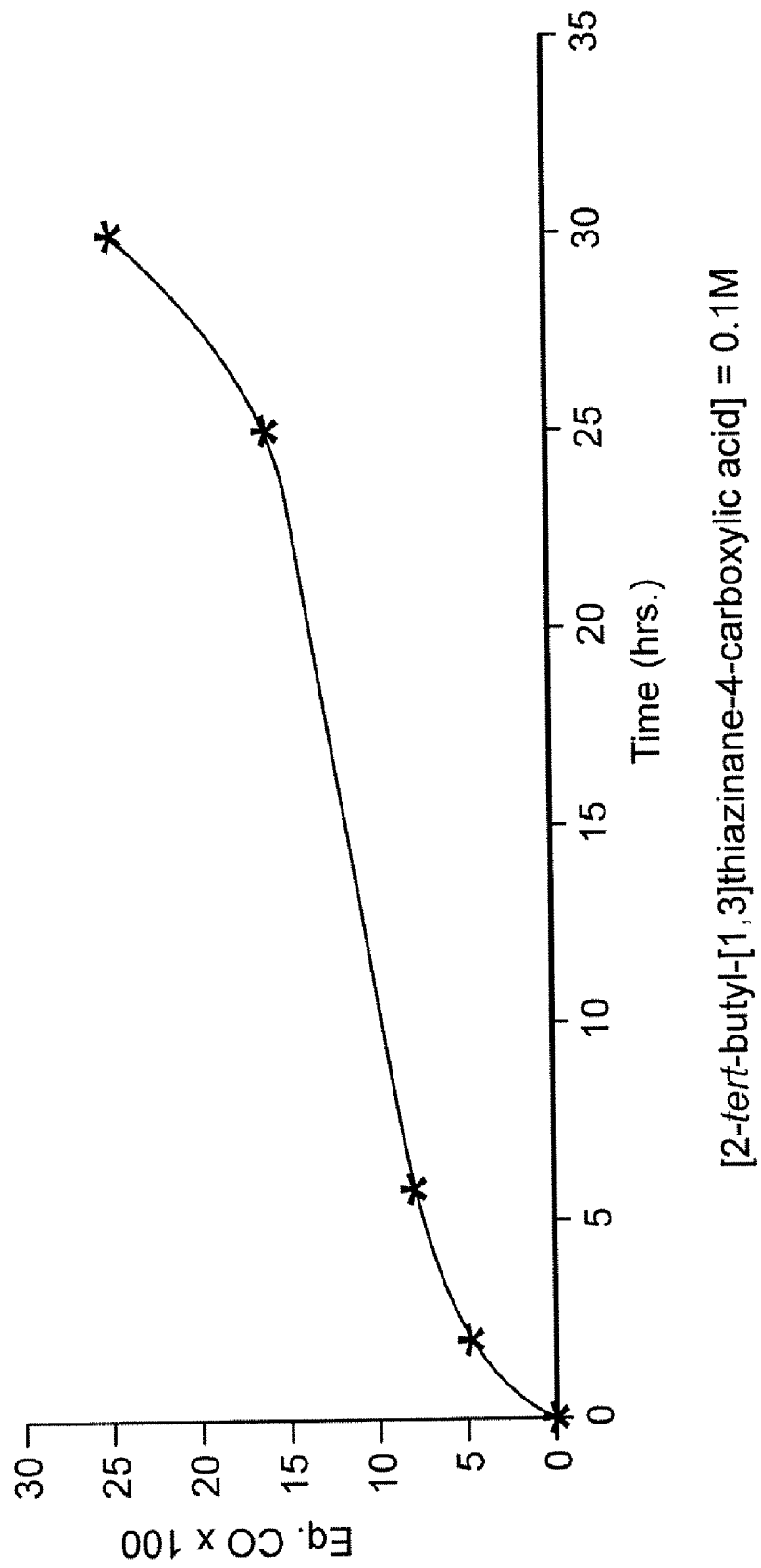
FIG. 19 is a plot showing the kinetics of CO release of 2-tert-butyl-[1,3]thiazinane-4-carboxylic acid (compound 12) in TBHP plus rpmi solution.

As shown in FIG. 19, 0.1 M 2-tert-butyl-[1,3]thiazinane-4-carboxylic acid exhibited CO release lower than its 5-membered ring analogue, reaching values of about 16% after one day. Compound 12 has good water solubility, so these results likely are due to reduced ring opening reactivity.

Table 1 summarizes the results of CO release experiments on various aldehyde prodrug compounds. The experiments were performed as described in Example 10. The results for compounds 9-12, generated as detailed in Examples 10-13, are included.

TABLE 1

| Compound | CO Release |
|---|---|
| 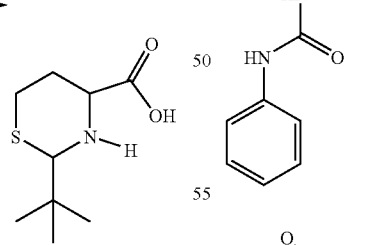 cis/trans mixture | Stable, but instaneous hydrolysis was observed when dissolved in water |
|  | No hydrolysis → No CO |
|  | No hydrolysis → No CO |
|  | 17% after 5 hours 21% after 23 hours |

TABLE 1-continued

| Compound | CO Release |
|---|---|
| (thiazolidine with CO2Me and t-Bu) | 0.3% after 6 hours<br>10.3% after 25 hours |
| (thiazolidine with t-Bu) | 3% after 6 hours<br>25% after 24 hours |
| (thiazinane with COOH and t-Bu) | 7.7% after 6 hours<br>15.8% after 25 hours |
| (oxazolidine with CO2Me and t-Bu) | 0% after 6 hours<br>4.2% after 24 hours |
| (N-methyl oxazolidine with t-Bu and phenyl) | No hydrolysis → No CO |
| (benzoxazine with t-Bu) | No hydrolysis → No CO |

Those skilled in the art will recognize, or be able to ascertain using no more than routine experimentation, many equivalents to the specific embodiments described herein. It is, therefore, to be understood that the foregoing embodiments are presented by way of example only, that the claimed invention may be practiced otherwise than as specifically illustrated, and that many modifications and variations will fall within the spirit and scope of that which is described and claimed.

What is claimed is:

1. A method for treating inflammatory disease in an animal in need thereof, comprising administering to the animal a pharmaceutical composition including an anti-inflammatory effective amount of a compound selected from the group consisting of trimethylacetaldehyde, 2,2-dimethyl-4-pentenal, 4-ethyl-4-formyl-hexanenitrile, 3-hydroxy-2,2-dimethylpropanal, 2-formyl-2-methyl-propylmethanoate, 2-ethyl-2-methyl-propionaldehyde, 2,2-dimethyl-3-(p-methylphenyl)propanal, or 2-methyl-2-phenylpropionaldehyde in a pharmaceutically acceptable vehicle, and wherein the inflammatory disease is arthritis, rheumatoid arthritis, juvenile idiopathic arthritis, osteoarthritis, psoriatic arthritis, or inflammatory bowel disease.

2. The method of claim 1, wherein the compound is administered concomitantly with a second anti-inflammatory agent.

3. The method of claim 1, wherein the pharmaceutical composition is a tablet, dragee, capsule, pill, powder, troche or granule.

4. The method of claim 1, wherein the pharmaceutical composition is a suspension, emulsion, solution, syrup or elixir.

5. The method of claim 1, wherein the pharmaceutical composition is formulated for parenteral administration.

6. The method of claim 1, wherein the inflammatory disease is arthritis.

7. The method of claim 6, wherein the inflammatory disease is rheumatoid arthritis.

8. The method of claim 6, wherein the inflammatory disease is juvenile idiopathic arthritis, osteoarthritis or psoriatic arthritis.

9. The method of claim 1, wherein the inflammatory disease is an inflammatory bowel disease.

10. The method of claim 1, wherein the compound is

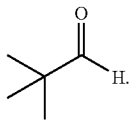

11. The method of claim 1, wherein the compound is

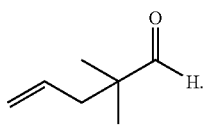

12. The method of claim 1, wherein the compound is

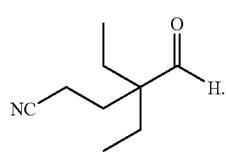

13. The method of claim 1, wherein the compound is
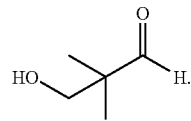
14. The method of claim 1, wherein the compound is
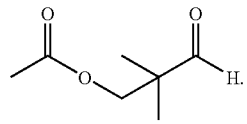
15. The method of claim 1, wherein the compound is
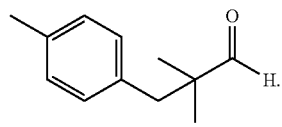
16. The method of claim 1, wherein the compound is
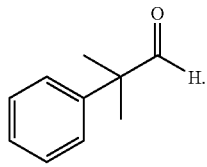
17. The method of claim 1, wherein the compound is
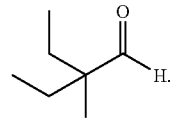
* * * * *